(12) United States Patent
Sedivy et al.

(10) Patent No.: US 12,350,264 B2
(45) Date of Patent: Jul. 8, 2025

(54) COMPOSITIONS AND METHODS FOR TREATING, PREVENTING OR REVERSING AGE-ASSOCIATED INFLAMMATION AND DISORDER

(71) Applicant: Brown University, Providence, RI (US)

(72) Inventors: John M. Sedivy, Barrington, RI (US); Gerwald Jogl, Pawtucket, RI (US); Alexandra D'Ordine, Lakeville, MA (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 18/537,765

(22) Filed: Dec. 12, 2023

(65) Prior Publication Data

US 2024/0207249 A1    Jun. 27, 2024

Related U.S. Application Data

(63) Continuation-in-part of application No. 17/778,369, filed as application No. PCT/US2020/061842 on Nov. 23, 2020.

(Continued)

(51) Int. Cl.

| | |
|---|---|
| A61K 31/554 | (2006.01) |
| A61K 31/136 | (2006.01) |
| A61K 31/145 | (2006.01) |
| A61K 31/166 | (2006.01) |
| A61K 31/167 | (2006.01) |
| A61K 31/17 | (2006.01) |
| A61K 31/19 | (2006.01) |
| A61K 31/192 | (2006.01) |
| A61K 31/194 | (2006.01) |
| A61K 31/195 | (2006.01) |
| A61K 31/196 | (2006.01) |
| A61K 31/366 | (2006.01) |
| A61K 31/381 | (2006.01) |
| A61K 31/4015 | (2006.01) |
| A61K 31/4035 | (2006.01) |
| A61K 31/4192 | (2006.01) |
| A61K 31/423 | (2006.01) |
| A61K 31/433 | (2006.01) |
| A61K 31/437 | (2006.01) |
| A61K 31/445 | (2006.01) |
| A61K 31/4704 | (2006.01) |
| A61K 31/4741 | (2006.01) |
| A61K 31/50 | (2006.01) |
| A61K 31/501 | (2006.01) |
| A61K 31/505 | (2006.01) |
| A61K 31/506 | (2006.01) |
| A61K 31/517 | (2006.01) |
| A61K 31/519 | (2006.01) |

(Continued)

(52) U.S. Cl.
CPC ........ *A61K 31/4741* (2013.01); *A61K 31/136* (2013.01); *A61K 31/145* (2013.01); *A61K 31/166* (2013.01); *A61K 31/167* (2013.01); *A61K 31/17* (2013.01); *A61K 31/19* (2013.01); *A61K 31/192* (2013.01); *A61K 31/194* (2013.01); *A61K 31/195* (2013.01); *A61K 31/196* (2013.01); *A61K 31/366* (2013.01); *A61K 31/381* (2013.01); *A61K 31/4015* (2013.01); *A61K 31/4035* (2013.01); *A61K 31/4192* (2013.01); *A61K 31/423* (2013.01); *A61K 31/433* (2013.01); *A61K 31/437* (2013.01); *A61K 31/445* (2013.01); *A61K 31/4704* (2013.01); *A61K 31/50* (2013.01); *A61K 31/501* (2013.01); *A61K 31/505* (2013.01); *A61K 31/506* (2013.01); *A61K 31/517* (2013.01); *A61K 31/519* (2013.01); *A61K 31/53* (2013.01); *A61K 31/554* (2013.01); *A61P 29/00* (2018.01)

(58) Field of Classification Search
None
See application file for complete search history.

(56) References Cited

U.S. PATENT DOCUMENTS

| | | |
|---|---|---|
| 5,859,037 A | 1/1999 | Whitcomb |
| 9,624,235 B2 | 4/2017 | Gold et al. |

(Continued)

FOREIGN PATENT DOCUMENTS

| | | |
|---|---|---|
| WO | 2008046014 A1 | 4/2008 |
| WO | 2017004436 A2 | 1/2017 |

(Continued)

OTHER PUBLICATIONS

CAS Registry No. 1197-18-8 ("Tranexamic Acid"). Retrieved from SciFinder Sep. 14, 2024. pp. 1-3. (Year: 2024).*

(Continued)

*Primary Examiner* — Leslie A. Royds Draper
(74) *Attorney, Agent, or Firm* — Adler Pollock & Sheehan P.C.

(57) ABSTRACT

Disclosed are methods for preventing, delaying or reversing age-associated inflammation, by administering to a patient in need thereof a therapeutically effective amount of at least one long interspersed nuclear element 1 (LINE-1, L1) endonuclease inhibitor (L1 EN inhibitor), either alone or in combination with at least one additional therapeutic agent. Effectiveness of the methods can be measured via biomarkers and/or by a decrease in symptoms compared to those symptoms before administration of the L1 EN inhibitor. Specific chemical structures of the L1 EN inhibitors are identified and shown herein.

4 Claims, 22 Drawing Sheets

Specification includes a Sequence Listing.

Related U.S. Application Data

(60) Provisional application No. 63/387,188, filed on Dec. 13, 2022, provisional application No. 63/077,888, filed on Sep. 14, 2020, provisional application No. 62/939,564, filed on Nov. 22, 2019.

(51) Int. Cl.
    *A61K 31/53* (2006.01)
    *A61P 29/00* (2006.01)

(56) References Cited

U.S. PATENT DOCUMENTS

| | | | |
|---|---|---|---|
| 10,100,307 | B2 | 10/2018 | Prochiantz et al. |
| 2007/0189967 | A1 | 8/2007 | Siclovan et al. |
| 2010/0029654 | A1* | 2/2010 | Pasinetti .............. A61K 31/47 514/307 |

FOREIGN PATENT DOCUMENTS

| | | |
|---|---|---|
| WO | 2018136920 A1 | 7/2018 |
| WO | 2020154656 A1 | 7/2020 |
| WO | 2021102423 A1 | 5/2021 |
| WO | 2022197689 A1 | 9/2022 |

OTHER PUBLICATIONS

Hiramoto et al. "Tranexamic Acid Improves Memory and Learning Abilities in Aging Mice". Journal of Experimental Pharmacology. 2020; 12:653-663. (Year: 2020).*

"Discussion Paper on the Clinical Investigation of Medicines for the Treatment of Alzheimer's Disease and Other Dementias", European Medicines Agency, Committee for Medicinal Products for Human Use (CHMP), Oct. 23, 2014, pp. 1-33.

"International Search Report and Written Opinion received for PCT Patent Application No. PCT/US2020/061842, mailed on Mar. 31, 2021", 14 pages.

Allen, et al., "Dock 6: Impact of New Features and Current Docking Performance", Journal of Computational Chemistry, vol. 36, 2015, pp. 1132-1156.

Banuelos-Sanchez, et al., "Synthesis and Characterization of Specific Reverse Transcriptase Inhibitors for Mammalian LINE-1 Retrotransposons", Cell Chemical Biology, vol. 26, Issue 8, Aug. 15, 2019, 30 pages.

Dai, et al., "Effect of Reverse Transcriptase Inhibitors on LINE-1 and Ty1 Reverse Transcriptase Activities and on LINE-1 Retrotransposition", BMC Biochemistry, vol. 12, No. 18, 2011, 11 pages.

De Cecco, et al., "Genomes of Replicatively Senescent Cells Undergo Global Epigenetic Changes Leading to Gene Silencing and Activation of Transposable Elements", Aging Cell, vol. 12, 2013, pp. 247-256.

De Cecco, et al., "L1 Drives IFN in Senescent Cells and Promotes Age-Associated Inflammation", Nature, vol. 566,, Feb. 2019, 33 pages.

De Cecco, et al., "Transposable Elements Become Active and Mobile in the Genomes of Aging Mammalian Somatic Tissues", Aging, vol. 5, No. 12, Dec. 2013, pp. 867-883.

Deleidi, et al., "Immune Aging, Dysmetabolism, and Inflammation in Neurological Diseases", Frontiers in Neuroscience, vol. 9, No. 172, Jun. 3, 2015, pp. 1-14.

Feng, et al., "Design and Activity of AP Endonuclease-1 Inhibitors", Journal of Chemical Biology, vol. 8, 2015, pp. 79-93.

Feng, et al., "Human L1 Retrotransposon Encodes a Conserved Endonuclease Required for Retrotransposition", Cell, vol. 87, Nov. 29, 1996, pp. 905-916.

Gold, et al., "Safety and Tolerability of Triumeq in Amyotrophic Lateral Sclerosis: The Lighthouse Trial", Amyotrophic Lateral Sclerosis and Frontotemporal Degeneration, 2019, pp. 1-10.

Liu, et al., "Loss of Nuclear TDP-43 is Associated with Decondensation of LINE Retrotransposons", Cell Reports 27, Apr. 30, 2019, 20 pages.

Lopez-Otin, et al., "The Hallmarks of Aging", Cell, vol. 153, Jun. 6, 2013, pp. 1194-1217.

Ostertag, et al., "Biology of Mammalian L1 Retrotransposons", Annual Review of Genetics, vol. 35, 2001, pp. 501-538.

Srinivasan, et al., "Identification and Characterization of Human Apurinic/Apyrimidinic Endonuclease-1 Inhibitors", Biochemistry, vol. 51, No. 31, 2012, pp. 6246-6259.

Trott, et al., "AutoDock Vina: Improving the Speed and Accuracy of Docking with a New Scoring Function, Efficient Optimization, and Multithreading", Journal of Computational Chemistry, vol. 31, No. 2, 2010, pp. 455-461.

Tyagi, et al., "Inhibition of Human Endogenous Retrovirus-K by Antiretroviral Drugs", Retrovirology, vol. 14, No. 21, 2017, 13 pages.

Weichenrieder, et al., "Crystal Structure of the Targeting Endonuclease of the Human LINE-1 Retrotransposon", Structure, vol. 12, No. 6, 2004, pp. 975-986.

Xie, et al., "Characterization of L1 Retrotransposition with High-Throughput Dual-Luciferase Assays", Nucleic Acids Research, vol. 39, No. 3, e16, 2011, 11 pages.

Zhang, et al., "Enriching Screening Libraries with Bioactive Fragment Space", Bioorganic & Medicinal Chemistry Letters, vol. 26, No. 15, 2016, 12 pages.

D'Ordine, et al., "Identification and characterization of small molecule inhibitors of the LINE-1 retrotransposon endonuclease", bioRxiv preprint doi: https://doi.org/10.1101/2022.12.29.522256, Dec. 29, 2022, 16 pages.

Miller, et al., "Structural dissection of sequence recognition and catalytic mechanism of human LINE-1 endonuclease", Nucleic Acids Research, vol. 49, No. 19, Sep. 23, 2021, pp. 11350-11366.

"CAS Registry No. 93479-97-1", Retrieved from SciFinder on Feb. 13, 2024, pp. 1-2.

"International Search Report and Written Opinion received for PCT Patent Application No. PCT/US2023/083704, mailed on May 10, 2024", 12 pages.

\* cited by examiner

ROLE OF CELLULAR SENESCENCE IN AGE-ASSOCIATED INFLAMMATION

CELLULAR SENESCENCE

⇓

UPREGULATION OF RTEs
(in particular LINE-1)

⇓

ACCUMULATION OF CYTOPLASMIC L1 cDNA

⇓

INDUCTION OF IFN-I
(via cGAS/STING etc.)

⇓

Crosstalk to Immune System, Reinforcement of SASP

⇓

Promotion of Age-Associated, "Sterile" Inflammation

FIG. 1

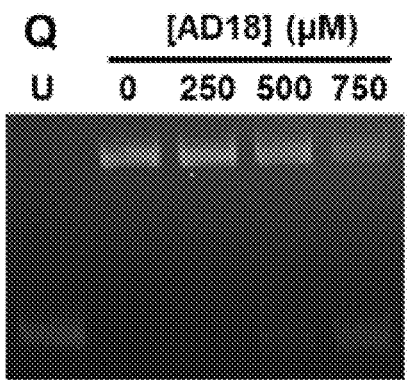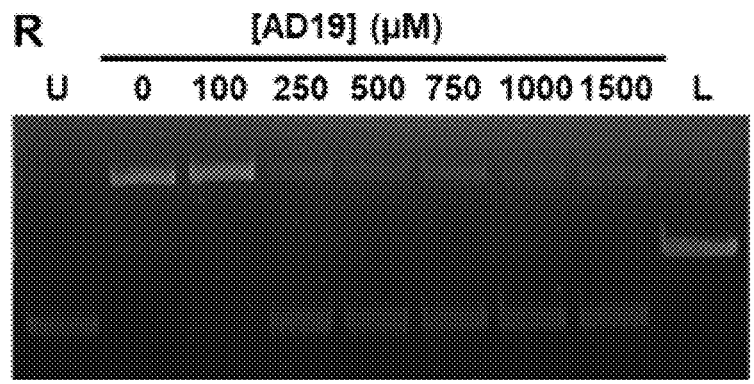
FIG. 2Q    FIG. 2R
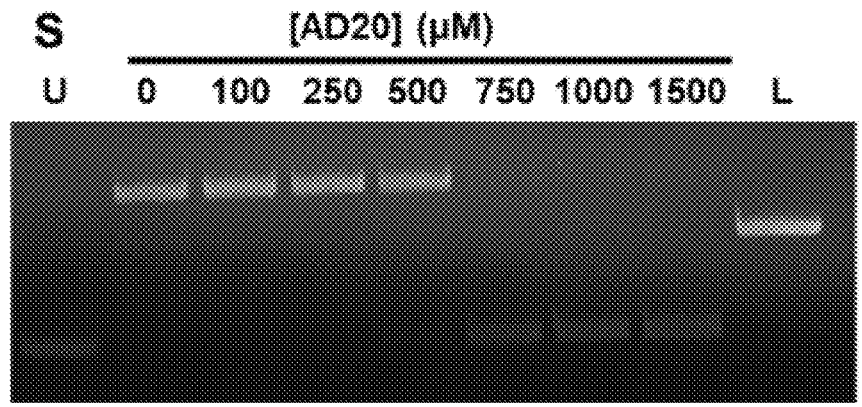
FIG. 2S
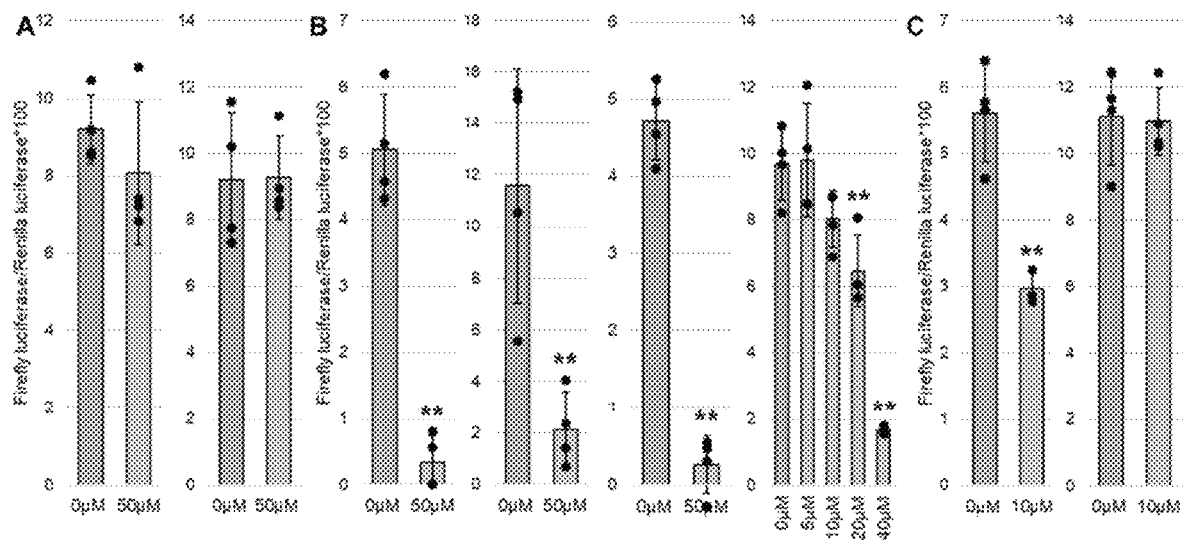
FIG. 3A    FIG. 3B    FIG. 3C

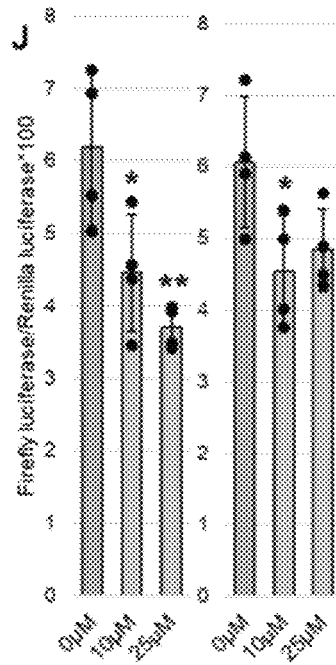
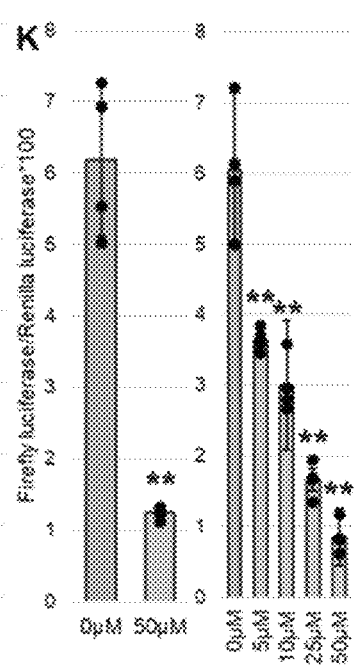
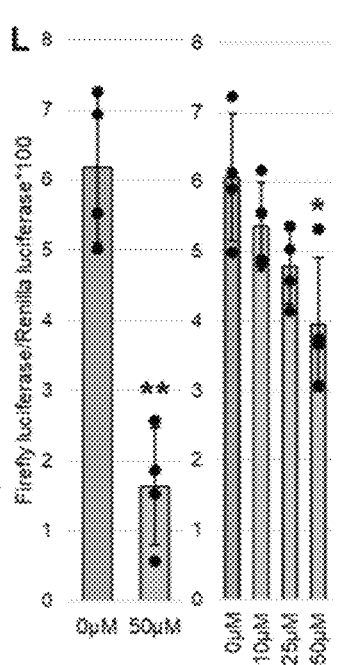
FIG. 3J  FIG. 3K  FIG. 3L
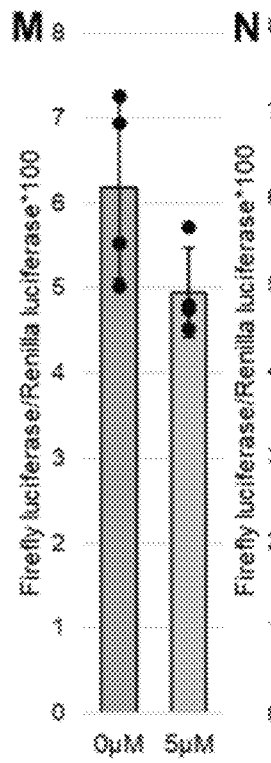
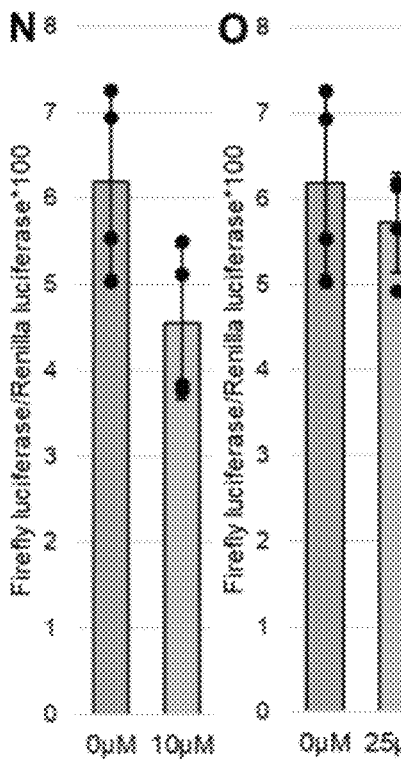
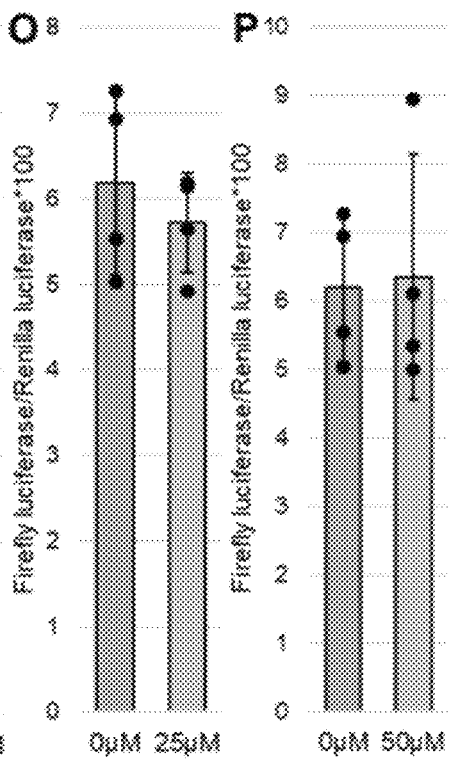
FIG. 3M  FIG. 3N  FIG. 3O  FIG. 3P

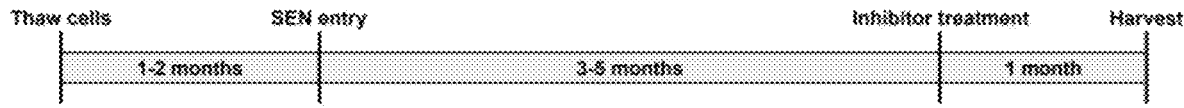
FIG. 10A
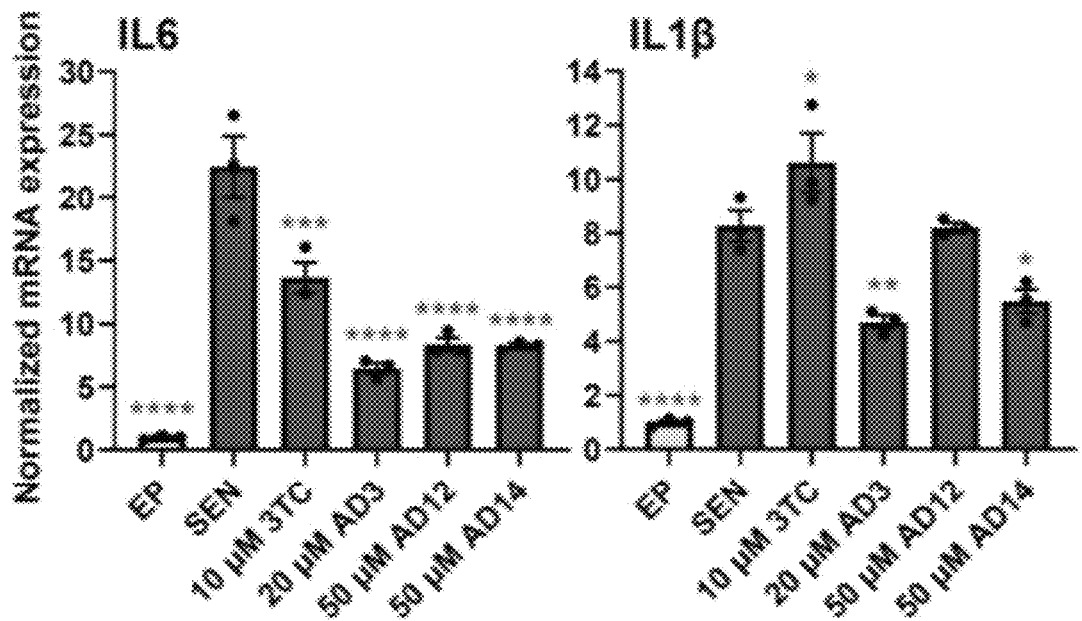
FIG. 10B  FIG. 10C
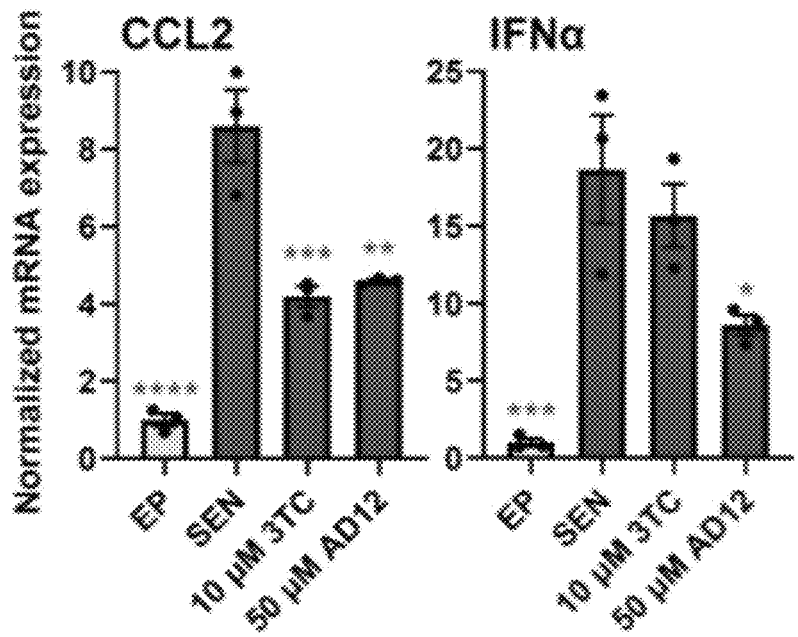
FIG. 10D  FIG. 10E

SEQUENCE LISTING

```
Sequence total quantity: 3
SEQ ID NO: 1            moltype = DNA   length = 43
FEATURE                 Location/Qualifiers
source                  1..43
                        mol_type = other DNA
                        organism = synthetic construct
SEQUENCE: 1
cgacttttag attgacacgc catgctgatc aatctaaaag tcg                    43

SEQ ID NO: 2            moltype =    length =
SEQUENCE: 2
000

SEQ ID NO: 3            moltype =    length =
SEQUENCE: 3
000
```

COMPOSITIONS AND METHODS FOR TREATING, PREVENTING OR REVERSING AGE-ASSOCIATED INFLAMMATION AND DISORDER

CROSS-REFERENCE TO RELATED APPLICATIONS

This application is a Continuation-in-part of U.S. application Ser. No. 17/778,369, filed May 19, 2022, which is a national phase application of PCT/US2020/061842, filed Nov. 23, 2020, which claims benefit of provisional applications 63/077,888, filed Sep. 14, 2020, and 62/939,564, filed Nov. 22, 2019; all of which are incorporated by reference herein in their entireties. This application claims benefit from U.S. Provisional Patent Application No. 63/387,188, filed Dec. 13, 2022, which is incorporated by reference herein in its entirety.

STATEMENT REGARDING FEDERALLY SPONSORED RESEARCH OR DEVELOPMENT

This invention was developed with the following funding: T32 grant: NIH GM007601; P01 grant: NIH AG051449; and R01 grant: NIH AG016694. The government has certain rights in the invention.

FIELD OF THE INVENTION

The invention is in the field of medicinal chemistry. In particular, the invention relates to a method for treating, preventing and reversing age-associated inflammation by administering a long interspersed nuclear element 1 (LINE-1) endonuclease inhibitor to a patient in need thereof. The age-associated inflammation may be in a patient having Alzheimer's disease, amyotrophic lateral sclerosis (ALS), Parkinson's disease, Huntington's disease, vision loss, hearing loss, peripheral degenerative diseases, or cardiovascular dysfunction, frontotemporal dementia (FTD), multiple sclerosis (MS), Aicardi Goutiere's syndrome, progressive supra nuclear palsy (PSP), osteoarthritis, skin aging, atherosclerosis, chemotherapy-induced adverse effects, hematopoietic stem cell function, osteoporosis, physical function, and/or pulmonary fibrosis, or in a patient in need of wound healing or tissue regeneration.

BRIEF DESCRIPTION OF THE SEQUENCE LISTING

This submission is accompanied by a "Sequence Listing XML" containing SEQ ID NOs: 1-3 and created on Dec. 8, 2023, 3 KB, submitted with the filename: "405505-621CP1US.xml". SEQ ID NO: 2 (5'-TTTT*A-3') and SEQ ID NO: 3 (F-CGACTTT) each contain less than 10 nucleotides and are thus mandatorily marked as intentionally skipped sequences under WIPO Sequence software version 2.3.0. The Sequence Listing XML was generated using WIPO Sequence software version 2.3.0, in accordance with 37 CFR §§ 1.831 through 1.835, and is herewith submitted as an XML file, via the USPTO patent electronic filing system, 37 CFR § 1.835(a)(1). The Sequence Listing XML is incorporated by reference herein in its entirety.

BACKGROUND OF THE INVENTION

The proportion of people living to be 60 years or older is increasing worldwide. Between 2012 and 2050, the number (and proportion) of people aged 60 years and over is expected to increase from 809 million to 2 billion (or 11% to 22% of the population).[i] Among the leading causes of death in the elderly are several chronic conditions including heart disease, cancer, diabetes, Alzheimer's disease, and infection. Importantly, many of these age-related diseases and aging itself are closely associated with low-level chronic inflammation.[ii,iii] Systemic chronic inflammation can accelerate aging.[iv] Indeed, many Inflammatory markers are significant predictors of mortality in older humans.[v]

Despite this common link between aging, inflammation, and chronic diseases, limited progress has been made to understand the mechanisms that control age-related inflammation, and the causal relationship of these regulators to chronic degenerative diseases is not completely understood. A better understanding of the role of these regulators in age-related inflammation should lead to new strategies for extending the health of the older population.

As such, there is a need in the art for better treatment and prevention of age-related inflammation and age-related disorders.

BRIEF SUMMARY OF THE INVENTION

The present invention provides a better understanding of the mechanisms underlying age-related inflammation and its role in the aging, as well as compositions and methods for preventing and reducing age-associated inflammation and disorders.

One of the hallmarks of aging is accumulation of senescent cells that contribute to sterile inflammation, which underlies many age-associated diseases. Senescent cells no longer proliferate and undergo changes in the global chromatin landscape. They also have increased DNA damage and produce proinflammatory factors known as the senescence associated secretory phenotype (SASP). Related to all of these deleterious characteristics is the expression of the long interspersed nuclear element-1 (LINE-1 or L1) retrotransposable element. While L1 repeats are normally repressed in heterochromatic regions of the genome, they become derepressed with age due to these changes in chromatin organization. This allows for L1 to copy itself into new genomic loci through the process of retrotransposition using the two catalytic activities encoded by its sequence, the reverse transcriptase (RT) and endonuclease (EN) domains. L1 also creates proinflammatory cytoplasmic DNA sequences as intermediates of retrotransposition. As a result, L1 activity is associated with diseases of aging such as osteoarthritis, cancer, and neurodegeneration.

Recent evidence from our laboratory demonstrated that inhibition of the L1 RT domain by nucleoside reverse transcriptase inhibitors (NRTIs), originally designed against the HIV RT, reduces the SASP in senescent cells in culture and in aging tissues. However, design of selective inhibitors for the L1 RT domain is currently not feasible due to the absence of structural information or knowledge about protein domain boundaries to enable recombinant protein purification. On the other hand, the structure of the L1 EN domain has been solved, allowing for structure-based inhibitor screening and design. The L1 EN is required for retrotransposition like the L1 RT, as L1 EN active site point mutations reduce retrotransposition similarly to those in the L1 RT. The L1 EN initiates L1 retrotransposition by nicking genomic DNA, which also results in double-strand breaks (DSBs) that can occur independent of L1 RT activity; it is estimated that the L1 EN can create 10-fold more DSBs than productive retrotransposition events. Additionally, inhibitors of the structurally homologous abasic site DNA repair endonuclease APE-1 have been characterized and provided initial candidate compounds. Based on these compounds, we have developed inhibitors of the L1 EN that have shown efficacy in a biochemical assay and retrotransposition assay in cells. The inhibitors developed herein are the first inhibitors of the L1 EN domain to be discovered and the first of any retrotransposon-encoded endonuclease.

Accordingly, the present invention provides inhibitors of the L1 EN that are useful for treating, preventing and/or reversing age-associated inflammation. A therapeutically effective amount of at least one L1 EN inhibitor is administered to a patient in need thereof.

The age-associated inflammation is associated with an upregulation of L1, an accumulation of cytoplasmic L1 cDNA, an activation of an IFN-I response, and/or a reinforcement of a SASP pro-inflammatory state. The L1 EN inhibitor is administered in an amount sufficient to prevent or reverse at least one of the upregulation of L1, the accumulation of cytoplasmic L1 cDNA, the activation of the IFN-I response, and/or the SASP pro-inflammatory state.

The age-associated inflammation that can be prevented, treated, or reversed with the methods of the present invention is in a patient having a disease or disorder including, but not limited to: Alzheimer's disease, amyotrophic lateral sclerosis (ALS), Parkinson's disease, Huntington's disease, vision loss, hearing loss, peripheral degenerative diseases, or cardiovascular dysfunction, frontotemporal dementia (FTD), multiple sclerosis (MS), Aicardi Goutiere's syndrome, progressive supra nuclear palsy (PSP), osteoarthritis, skin aging, atherosclerosis, chemotherapy-induced adverse effects, hematopoietic stem cell function, osteoporosis, physical function, and/or pulmonary fibrosis, or in a patient in need of wound healing or tissue regeneration. In one embodiment, the age-associated inflammation is in a patient having Alzheimer's disease. In an alternate embodiment, the age-associated inflammation is in a patient having ALS.

Also provided is a method for delaying or reversing the progression of the underlying pathology of disease disorder caused by age-associated inflammation, comprising administering to a patient in need thereof a therapeutically effective amount of at least one L1 EN inhibitor. In some embodiments, the patient has Alzheimer's disease or ALS and experiences a decrease in one or more symptoms of Alzheimer's disease or ALS compared to before the first administration of the L1 EN inhibitor to the patient. In some embodiments, the one or more symptoms of Alzheimer's disease comprise memory loss, misplacing items, forgetting the names of places or objects, repeating questions, being less flexible, confusion, disorientation, obsessive behavior, compulsive behavior, delusions, aphasia, disturbed sleep, mood swings, depression, anxiety, frustration, agitation, difficulty in performing spatial tasks, agnosia, difficulty with ambulation, weight loss, loss of speech, loss of short term memory or loss of long term memory.

In some embodiments, the one or more L1 EN inhibitors are selected from AD2, AD3, AD4, AD5, AD6, AD7, AD8, AD9, AD10, AD11, AD12, AD13, AD14, AD16, AD17, AD18, AD19, AD20, AD22, AD23, AD28, AD29, AD32, AD34, AD36, AD37, AD38, AD39, AD40, AD41, AD42, AD43, AD44, AD45, AD46, AD47, AD48, AD49, AD50, AD51, AD52, AD53, AD54, and AD55. In some embodiments, the one or more L1 EN inhibitors are selected from AD22, AD23, AD28, AD29, AD32, AD34, AD36, AD37, AD38, AD39, AD40, AD41, AD42, AD43, AD44, AD45, AD46, AD47, AD48, AD49, AD50, AD51, AD52, AD53, AD54, and AD55. In some embodiments, the one or more L1 EN inhibitors are selected from AD22, AD23, AD28, AD29, AD32, AD34, and AD36. In some embodiments, the one or more L1 EN inhibitors are selected from AD37, AD38, AD39, AD40, AD41, AD42, AD43, AD44, AD45, AD46, AD47, AD48, AD49, AD50, AD51, AD52, AD53, AD54, and AD55.

In some embodiments, the decrease in the one or more symptoms of Alzheimer's disease is evaluated according to the DSM-5.[vi] In some embodiments, the decrease of symptoms is determined using the cognitive subscale of the Alzheimer's Disease Assessment Scale (ADAS-cog). In some embodiments, the decrease of symptoms is determined using the Clinician's Interview-Based Impression of Change (CIBIC-plus). In some embodiments, the decrease of symptoms is determined using the Activities of Daily Living (ADL) scale. In some embodiments, the decrease of symptoms is for 1-36 months.

In some embodiments, any change in the underlying pathology is identified by detection of a biomarker before and after the L1 EN inhibitor administration. In some embodiments, the biomarker is β-amyloid or Tau protein. In some embodiments, the biomarker is detected by PET imaging. In some embodiments, the underlying pathology is identified by measurement of β-amyloid or Tau protein in the cerebrospinal fluid. In some embodiments, the underlying pathology is identified by measurement of brain volume before and after the L1 EN inhibitor administration. In some embodiments, the underlying pathology is reversed or delayed for at 1-36 months.

In some embodiments, the patient has Alzheimer's disease, and the method further comprises administering at least one second therapeutic agent useful for the treatment of the symptoms of Alzheimer's disease. In some embodiments, the at least one second therapeutic agent is selected from: donepezil, galantamine, memantine, and/or rivastigmine. In some embodiments, the at least one second therapeutic agent is an antibody that binds to β-amyloid or Tau protein. In some embodiments, the antibody binds to β-amyloid and is bapineuzumab. In some embodiments, the antibody binds to Tau protein and is ABBV-8E12. In some embodiments, the at least one second therapeutic agent is a vaccine against β-amyloid or Tau protein. In some embodiments, the at least one second therapeutic agent is an agent that reduces or alters the brain content of β-amyloid or Tau. In some embodiments, the second therapeutic agent reduces or alters the brain content of β-amyloid and is a β-secretase 1 (BACE) inhibitor. In some embodiments, the BACE inhibitor is selected from: CTS-21166, lanabecestat (AZD3293), LY2886721, and verubecestat (MK-8931). In some embodiments, the second agent reduces or alters the brain content of Tau and is nicotinamide, or MPT0G211.

In some embodiments, the patient has ALS, and the method further comprises administering at least one second therapeutic agent useful for the treatment of the symptoms of ALS. In some embodiments, the at least one second agent useful for the treatment of ALS is edaravone and/or riluzole. In other embodiments, the at least one second agent is an integrase inhibitor. In some embodiments, the integrase inhibitor is selected from: aurintricarboxylic acid, derivatives of aurintricarboxylic acid, BMS-538158, caffeic acid phenethyl ester, derivatives of caffeic acid phenethyl ester, curcumin, derivatives of curcumin, chicoric acid, derivatives of chicoric acid, 3,5-dicaffeoylquinic acid, derivatives of 3,5-dicaffeoylquinic acid, GSK364735C, L-870812, and L-25 870810, MK-0518, quercetin, derivatives of quercetin, raltegravir, S-1360, tyrphostin, derivatives of tyrphostin, and/or zintevir (AR-177).

In some embodiments, the patient is evaluated for one or more symptoms or disease pathology for 1-36 months after the first administration to the patient of the one or more L1 EN inhibitor.

In some embodiments, the one or more L1 EN inhibitor inhibits L1 reverse transcriptase activity in a cell of the patient.

Also provided is a method for preventing the onset of Alzheimer's disease in a patient suspected of having mild cognitive impairment or preclinical Alzheimer's disease, comprising administering a therapeutically effective amount of at least one L1 EN inhibitor to a patient in need thereof.

Other implementations are also described and recited herein.

BRIEF DESCRIPTION OF THE DRAWINGS

For the purpose of illustration, certain embodiments of the present invention are shown in the drawings described below. It should be understood, however, that the invention is not limited to the precise arrangements, data, and conditions shown. In the drawings:

FIG. 1 is a flow chart outlining the molecular pathway of cellular senescence leading to age-associated, "sterile" inflammation.

FIG. 3A-3P panels: FIG. 3A) AD2, FIG. 3B) AD3, FIG. 3C) AD6, FIG. 3D) AD7, FIG. 3E) AD9, FIG. 3F) AD10, FIG. 3G) AD11, FIG. 3H) AD12, FIG. 3I) AD13, FIG. 3J) AD14, FIG. 3K) AD15, FIG. 3L) AD16, FIG. 3M) AD17, FIG. 3N) AD18, FIG. 3O) AD19, FIG. 3P) AD20. Error bars=standard deviation, *p≤0.05, **p≤0.01.

FIG. 4A shows a schematic of the fluorescent oligonucleotide nicking assay with SEQ ID NO: 1, F-CGACTTTTAGATTGACACGCCATGCTGAT-CAATCTAAAAGTCG-Q, or

F-(SEQ ID NO: 1)-Q.

Figure 4A:
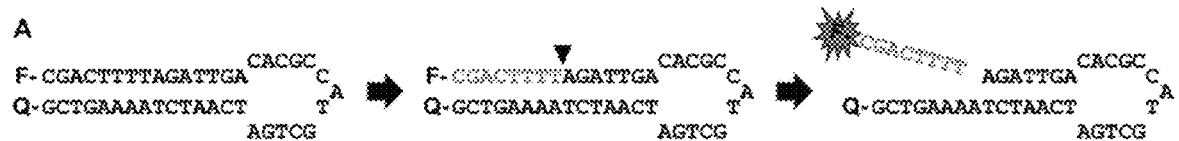
FIGS. 4A-4U show the results of fluorescent oligonucleotide nicking assay results for L1 EN inhibitors.
Figures 4B, 4C:
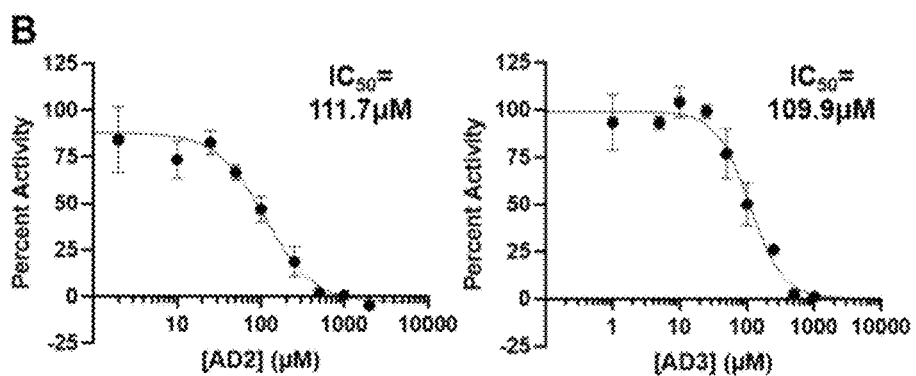
Figures 4D, 4E:
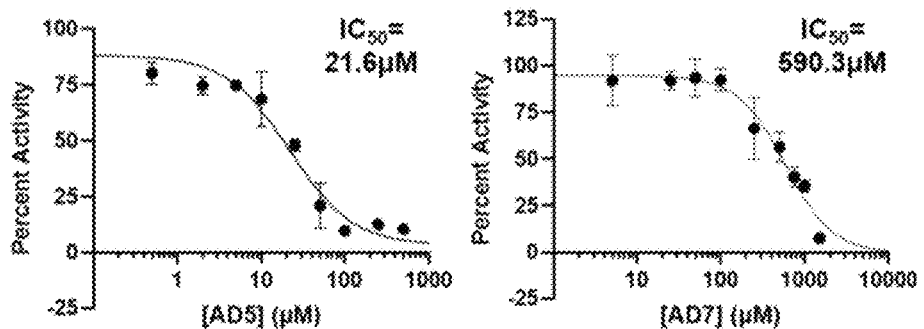
Figure 4F:
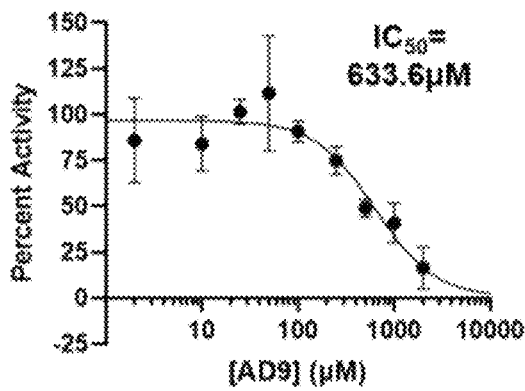
Figure 4G:
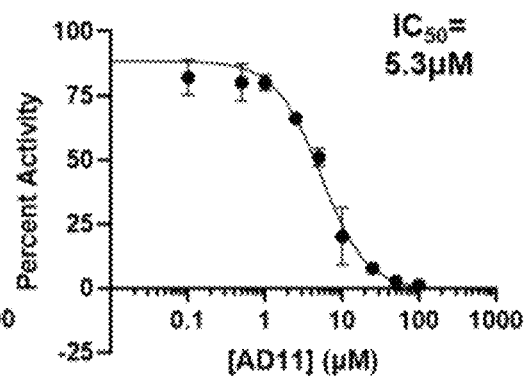
Figure 4H:
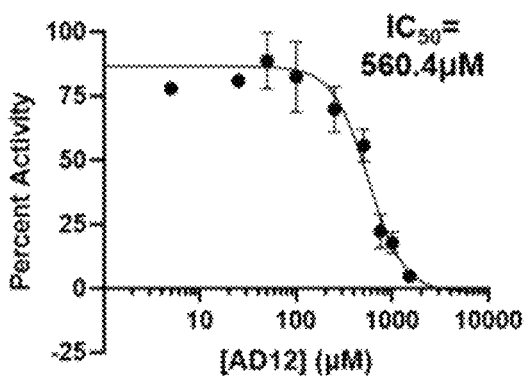
Figure 4I:
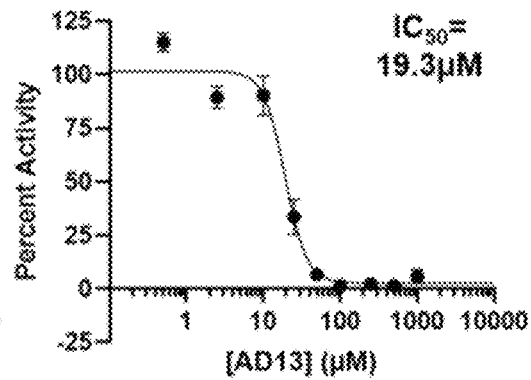
Figure 4J:
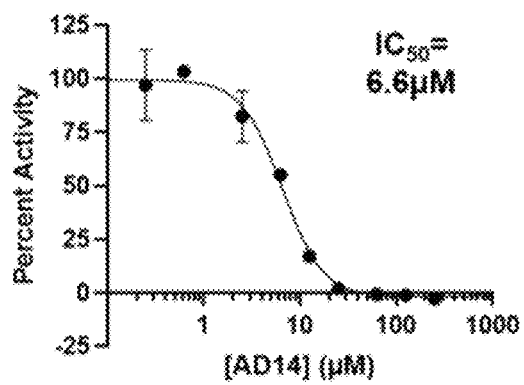
Figure 4K:
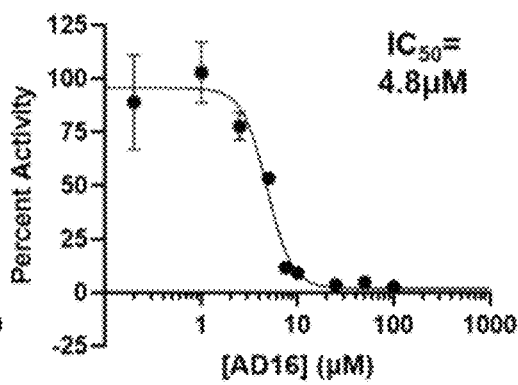
Figure 4L:
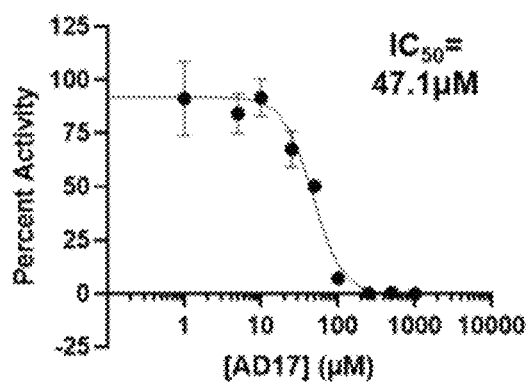
Figure 4M:
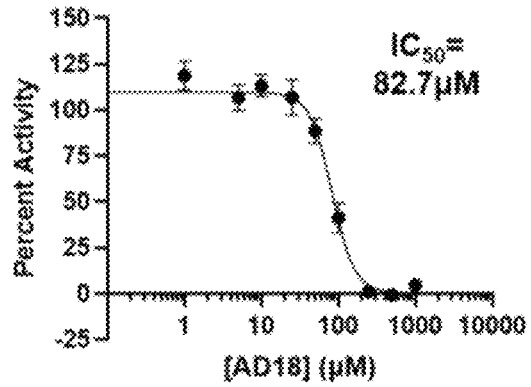
Figure 4N:
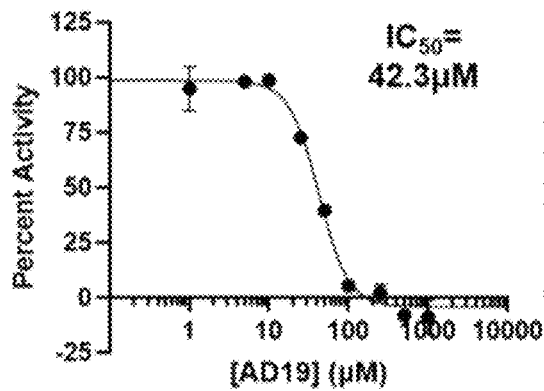
Figure 4O:
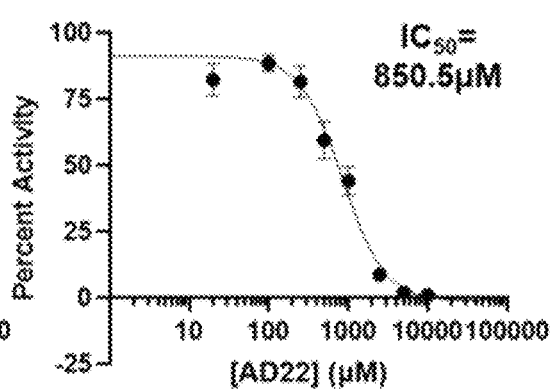
Figure 4P:
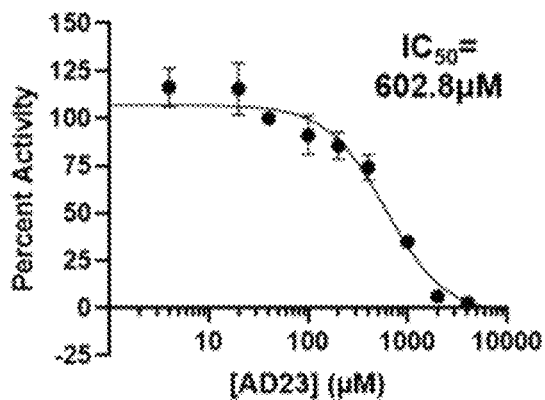
Figure 4Q:
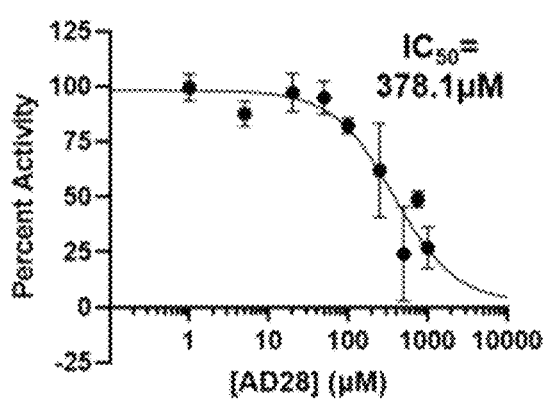
Figure 4R:
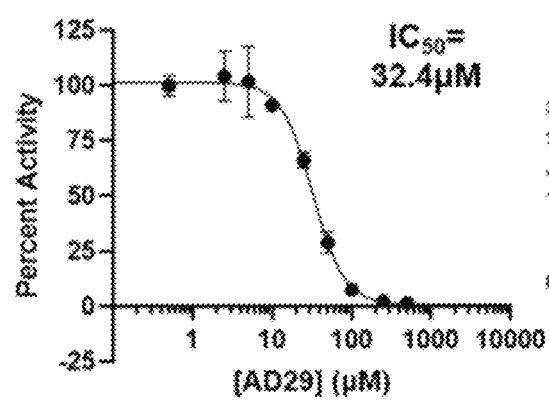
Figure 4S:
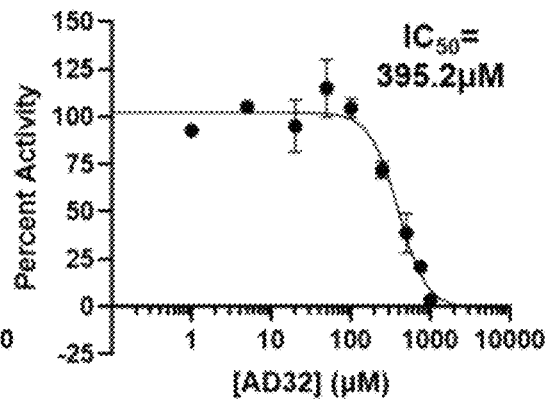
Figure 4T:
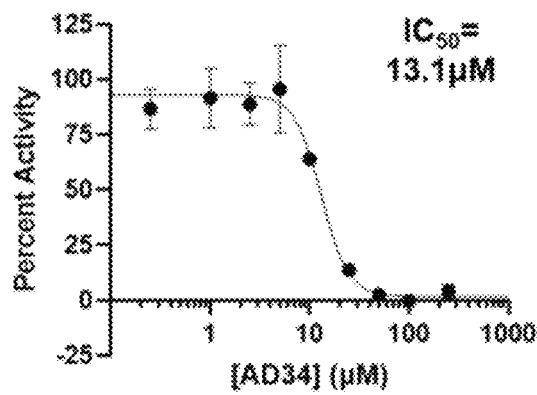
Figure 4U:
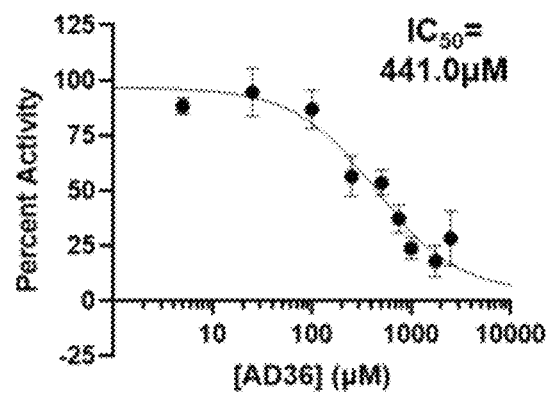

At left is shown the sequence of the hairpin oligonucleotide containing 5' 6-FAM fluorescein fluorophore (F) and 3' DABCYL quencher (Q), adapted from Srinivasan, et al., 2012.[ix] At middle of FIG. 4A, the arrowhead indicates location of nick by L1 EN at the semi-specific target site sequence, SEQ ID NO: 2, 5'-TTTT*A-3'. The melting temperature of the green sequence, SEQ ID NO: 3, F-CGACTTT, or F-(SEQ ID NO: 3), is lower than reaction temperature, whereas melting temperature of full hairpin is higher than the reaction temperature. At right, the nicked sequence is released away from the quencher, allowing for fluorescence to occur as a real-time readout for activity using a plate reader. FIGS. 4B-4U show representative assay results for L1 EN inhibitors. Graphs show percent of no inhibitor control L1 EN activity as a function of indicated inhibitor concentration. Activity was determined as initial rate of reaction under multiple turnover conditions and normalized to no inhibitor control. $IC_{50}$ values were calculated using [inhibitor] vs. response non-linear fit in GraphPad Prism version 9.4.1 for Windows. No inhibitor control and full inhibition by 50 mM EDTA were included in fit calculations to guide definition of top and bottom of fit curve. Representative assay results are shown for AD2 (FIG. 4B), AD3 (FIG. 4C), AD5 (FIG. 4D), AD7 (FIG. 4E), AD9 (FIG. 4F), AD11 (FIG. 4G), AD12 (FIG. 4H), AD13 (FIG. 4I), AD14 (FIG. 4J), AD16 (FIG. 4K), AD17 (FIG. 4L), AD18 (FIG. 4M), AD19 (FIG. 4N), AD22 (FIG. 4O), AD23 (FIG. 4P), AD28 (FIG. 4Q), AD29 (FIG. 4R), AD32 (FIG. 4S), AD34 (FIG. 4T), and AD36 (FIG. 4U).

Figure 5A:
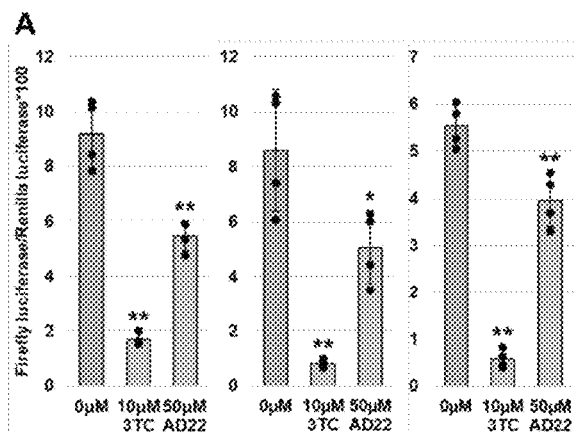
Figure 5B:
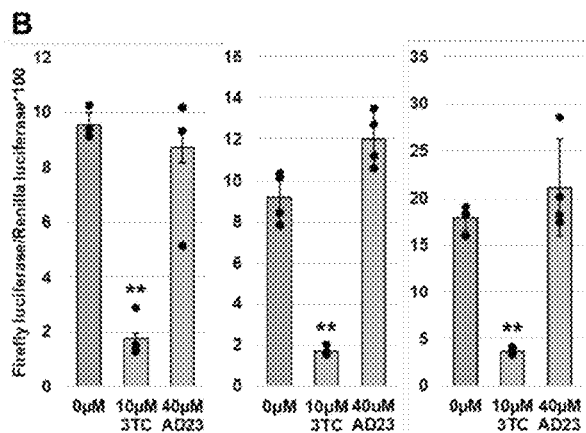
Figure 5C:
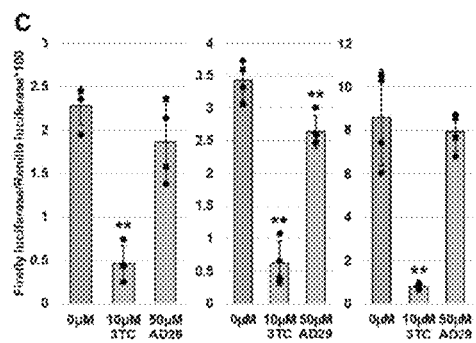
Figure 5D:
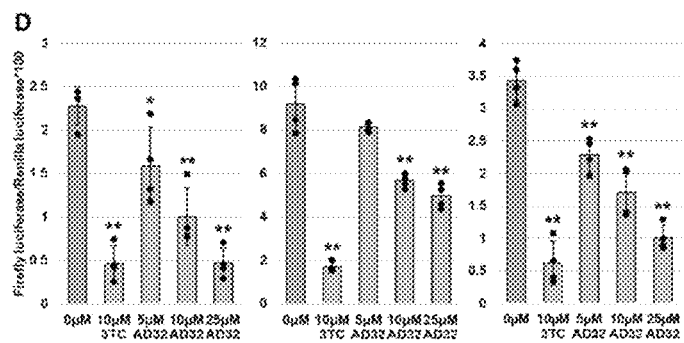
Figure 5E:
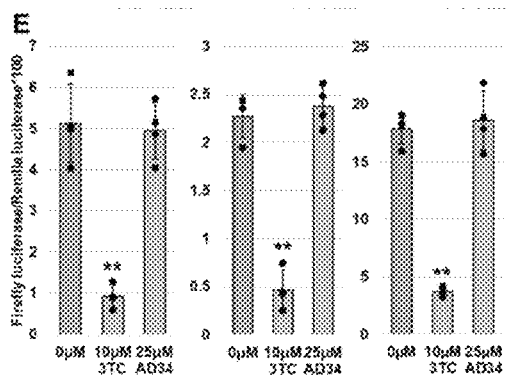
Figure 5F:
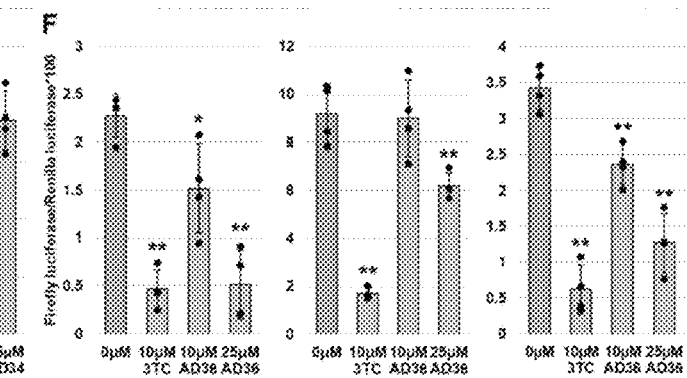

FIGS. 5A-5F show retrotransposition assay results for new inhibitors. Retrotransposition was measured in Hela cells by expression of a luciferase reporter after a retrotransposition event. 3TC was included for comparison to L1 RT inhibition. During compound screening with this assay, PrestoBlue Viability Reagent was used to test cytotoxicity; compounds with statistically significant toxicity were subsequently tested at lower concentrations or excluded from further testing. Statistical significance relative to no inhibitor control (0 μM) determined using an unpaired two-tailed t-test. FIGS. 5A-5F panels: FIG. 5A) AD22, FIG. 5B) AD23, FIG. 5C) AD29, FIG. 5D) AD32, FIG. 5E) AD34, FIG. 5F) AD36. Error bars=S.D., *p≤0.05, **p≤0.01.

Figure 6A:
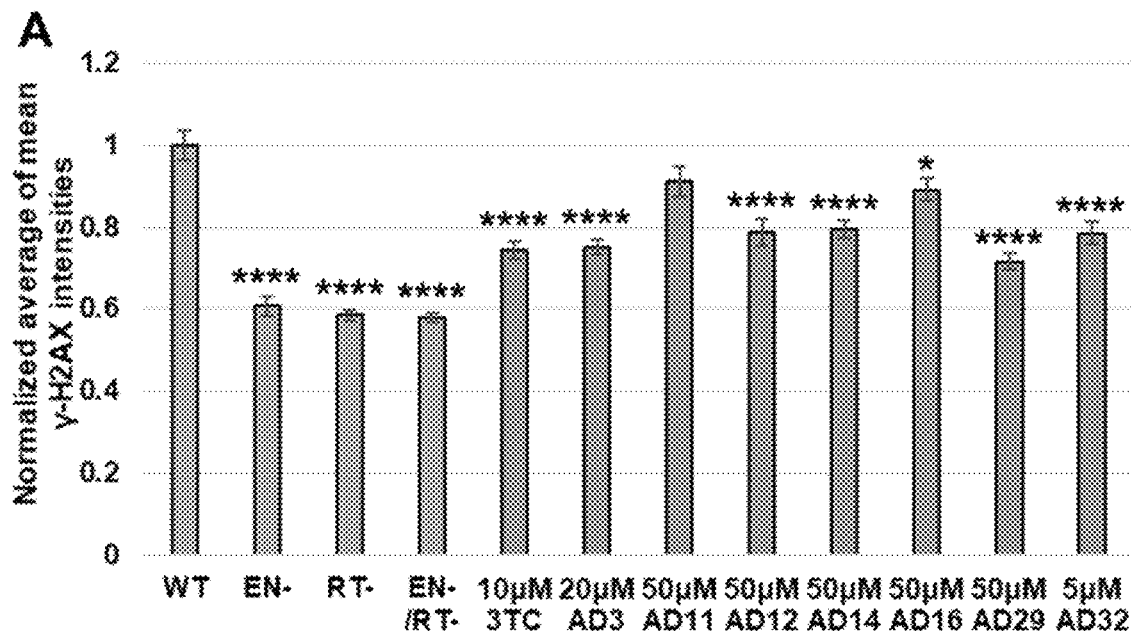
Figure 6B:
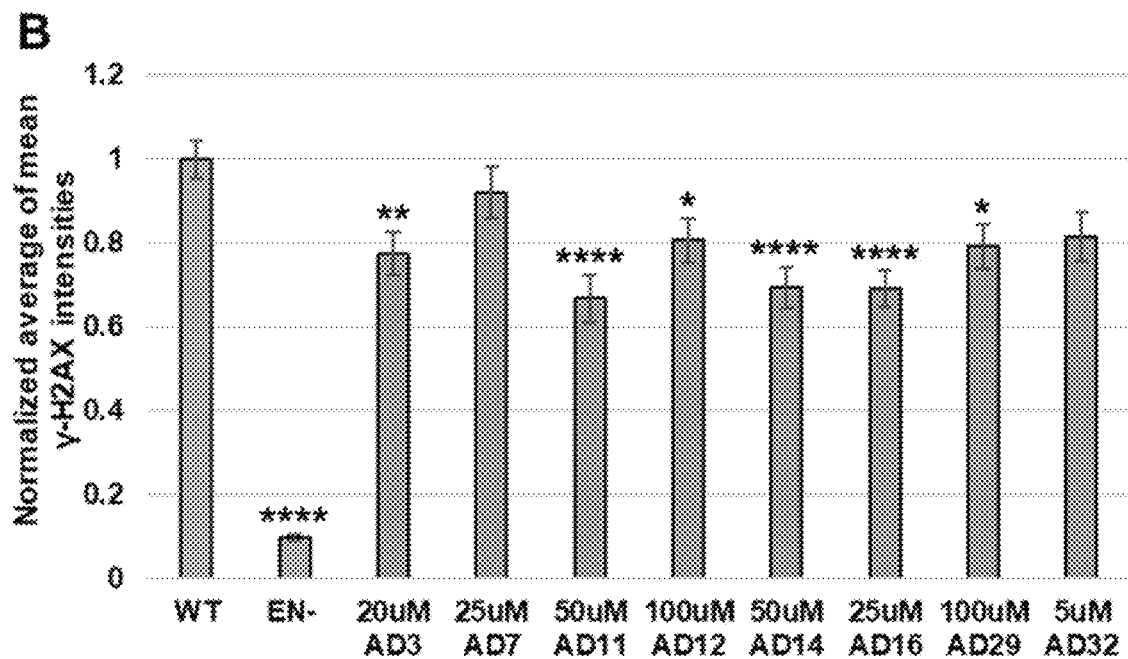

FIGS. 6A-6B show the effects of L1 EN inhibitors on L1-induced DNA damage. HeLa Tet-On cell lines containing doxycycline-inducible full-length (FL, ORF1 and ORF2) or L1 EN domain only L1 expression constructs were generated for WT and mutant (EN-, H230A; RT-, D702Y) L1. FIG. 6A shows average of mean γ-H2AX intensities of individual nuclei (n=233-723) normalized to WT no inhibitor control for FL expression. FIG. 6B shows average of mean γ-H2AX intensities of individual nuclei (n=68-256) normalized to WT no inhibitor control for L1 EN domain expression. Results are from at least 2 independent experiments per sample. All samples from the same experiment were processed in parallel and images were acquired with the same exposure. Mean γ-H2AX intensity analysis was performed with CellProfiler. Statistical significance vs. WT was determined by one-way ANOVA followed by Dunnett's multiple comparisons test using GraphPad Prism version 9.4.1 for Windows. Error bars: ±S.E., *p<0.05, p<0.01, *p<0.001, ****p<0.0001.

Figure 7A:
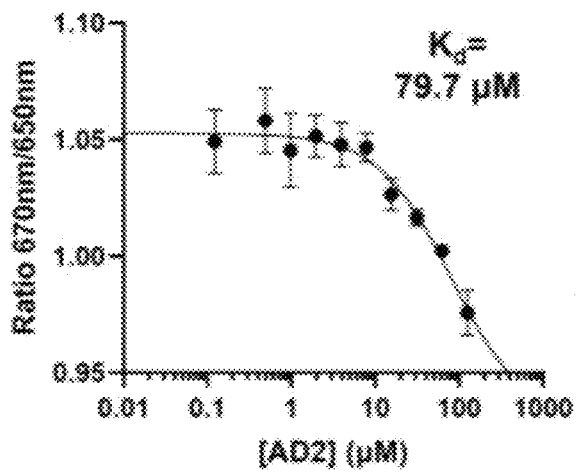
Figure 7B:
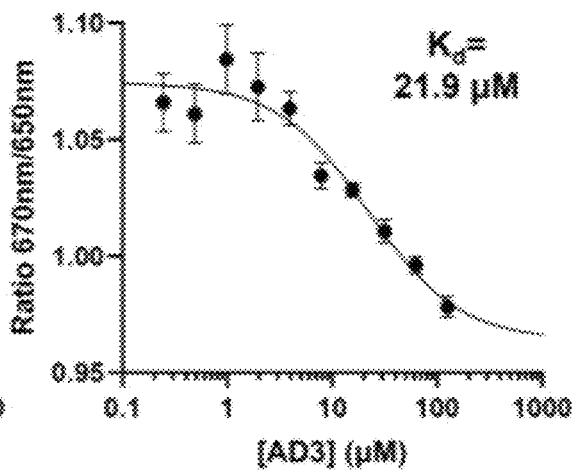
Figure 7C:
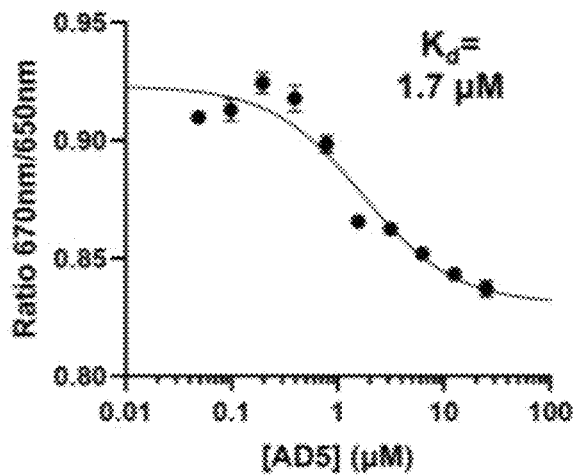
Figure 7D:
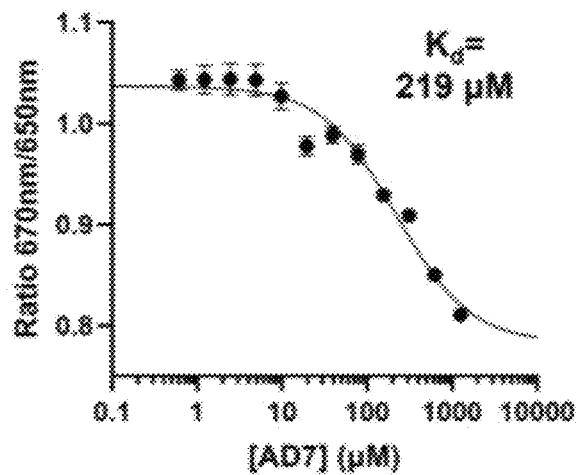
Figure 7E:
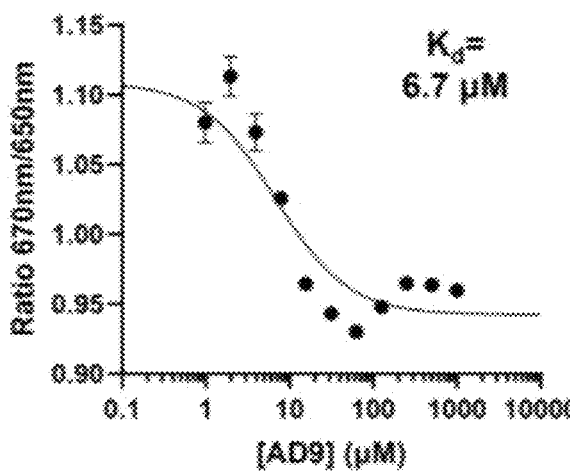
Figure 7F:
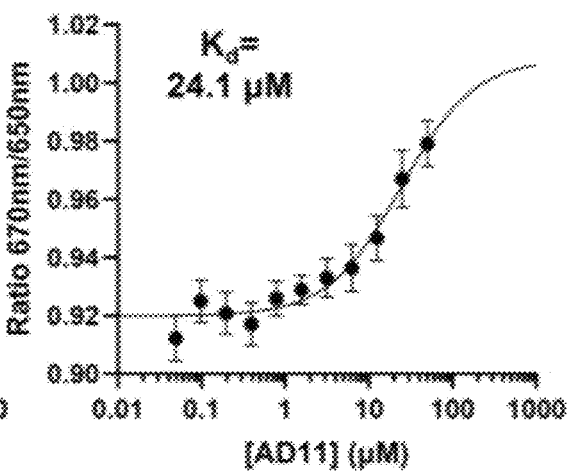
Figures 7G, 7H:
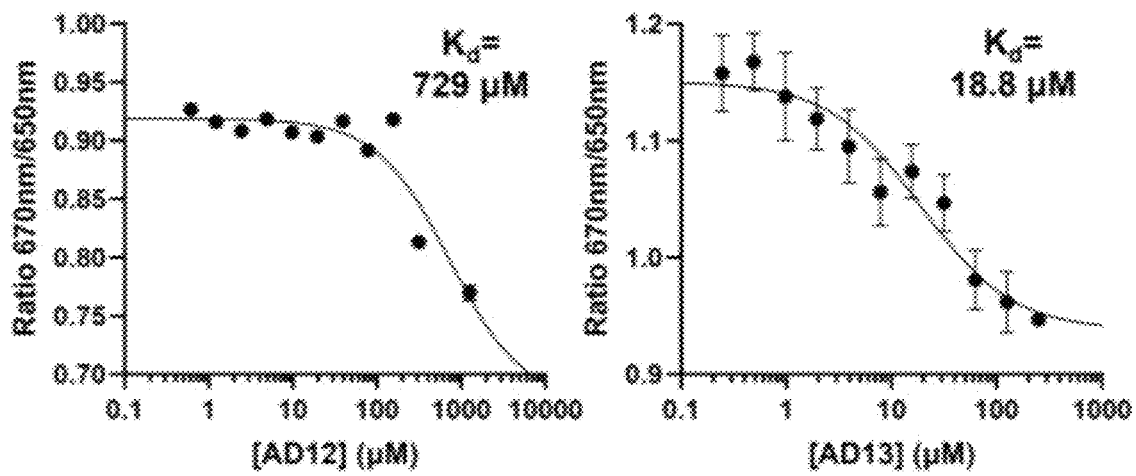
Figures 7I, 7J:
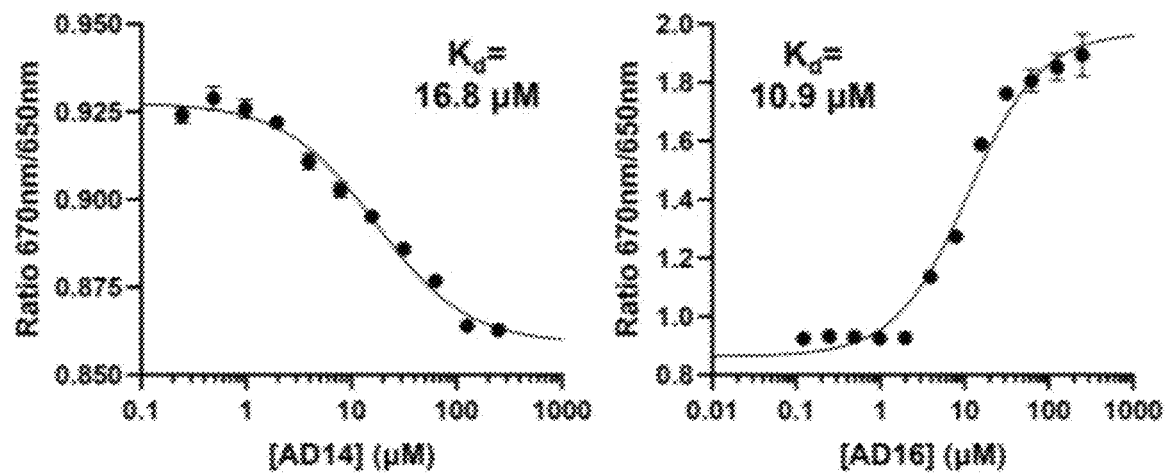
Figures 7K, 7L:
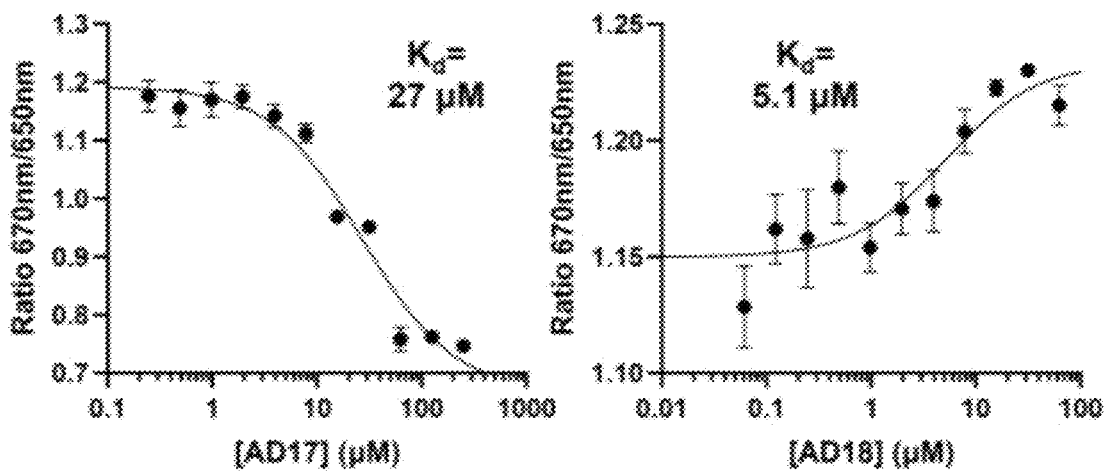
Figure 7M:
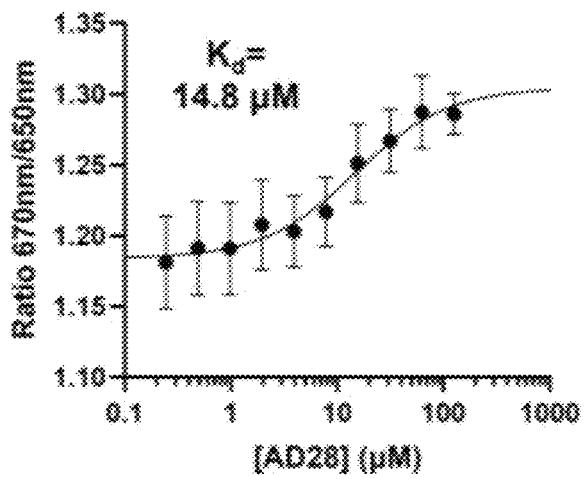
Figure 7N:
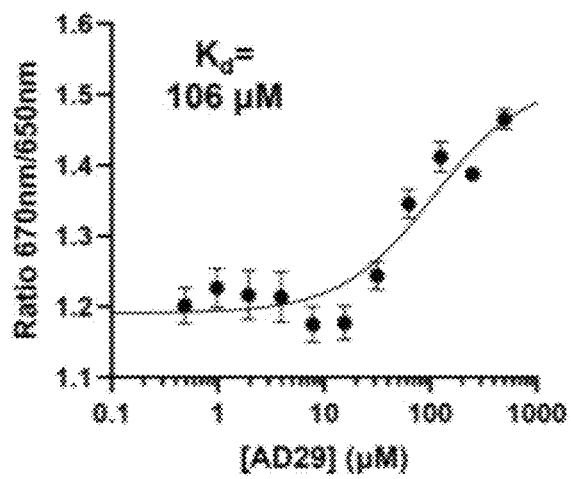
Figure 7O:
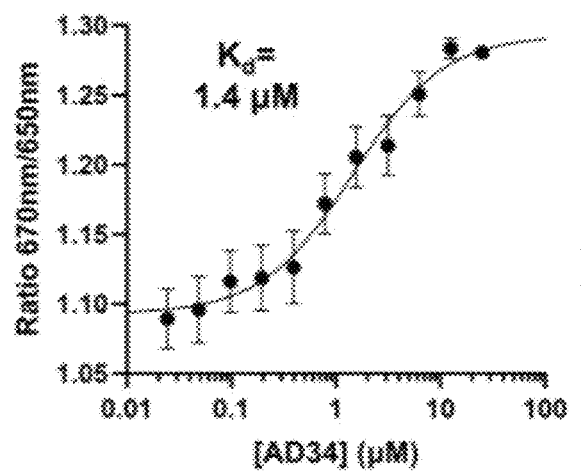
Figure 7P:
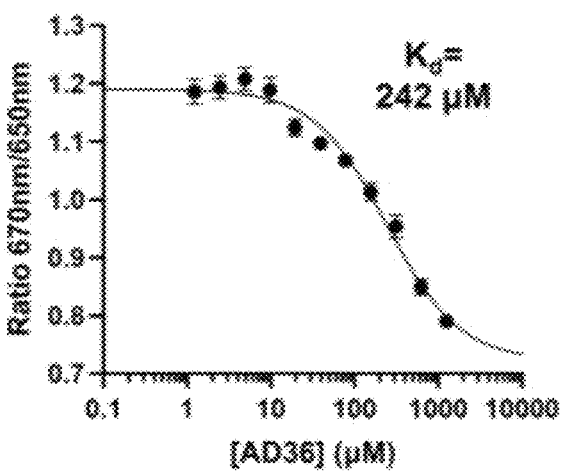
Figure 7Q:
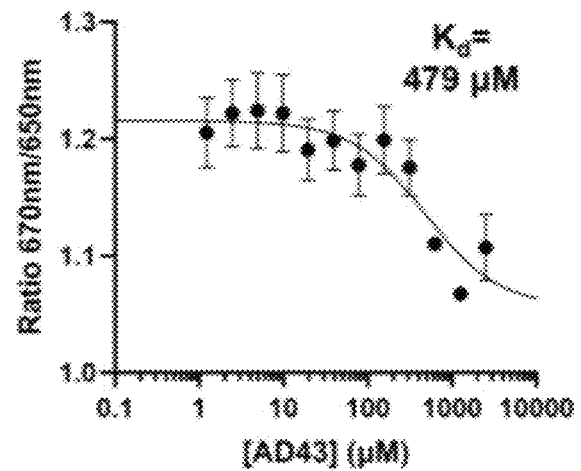
Figure 7R:
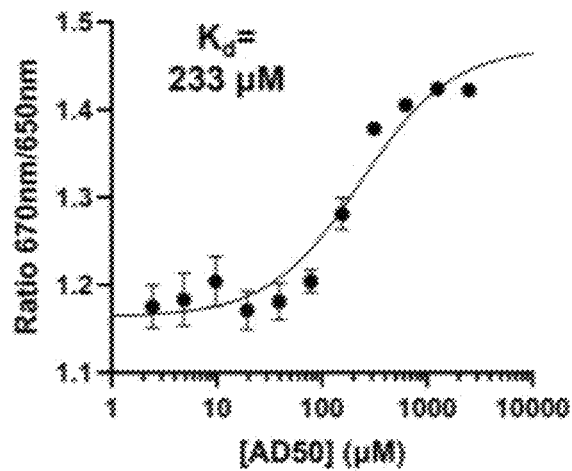

FIGS. 7A-7R show spectral shift binding affinity measurements of EN inhibitors. Representative assay results for each EN inhibitor with detectable binding. EN was fluorescently tagged and incubated with indicated concentrations of inhibitors. Spectral shift measurements were completed using a Monolith X instrument (NanoTemper). $K_d$ values were calculated by MO. Control software (NanoTemper). Error bars=s.d. from triplicate reads of each capillary. Representative assay results are shown for AD2 (FIG. 7A), AD3 (FIG. 7B), AD5 (FIG. 7C), AD7 (FIG. 7D), AD9 (FIG. 7E), AD11 (FIG. 7F), AD12 (FIG. 7G), AD13 (FIG. 7H), AD14 (FIG. 7I), AD16 (FIG. 7J), AD17 (FIG. 7K), AD18 (FIG. 7L), AD28 (FIG. 7M), AD29 (FIG. 7N), AD34 (FIG. 7O), AD36 (FIG. 7P), AD43 (FIG. 7Q), and AD50 (FIG. 7R).

Figure 8A:
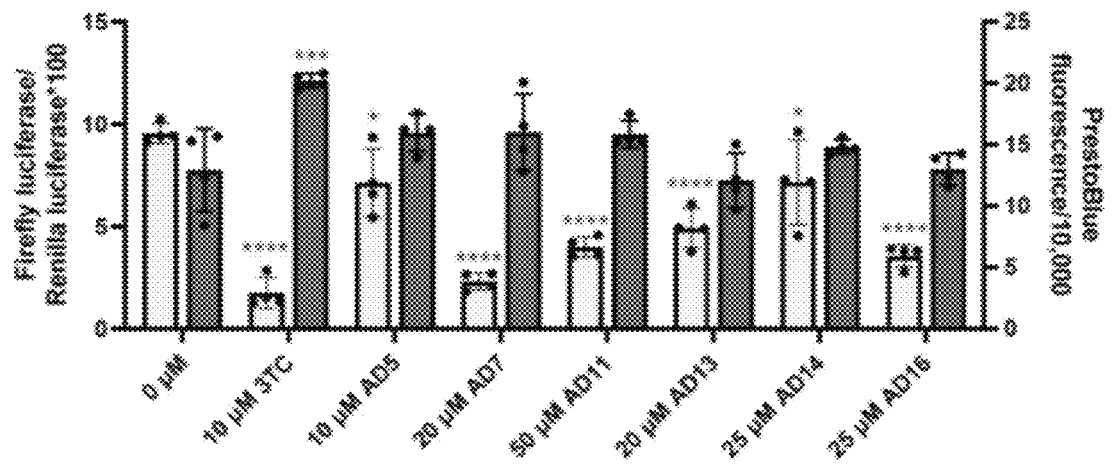
Figures 8B, 8C:
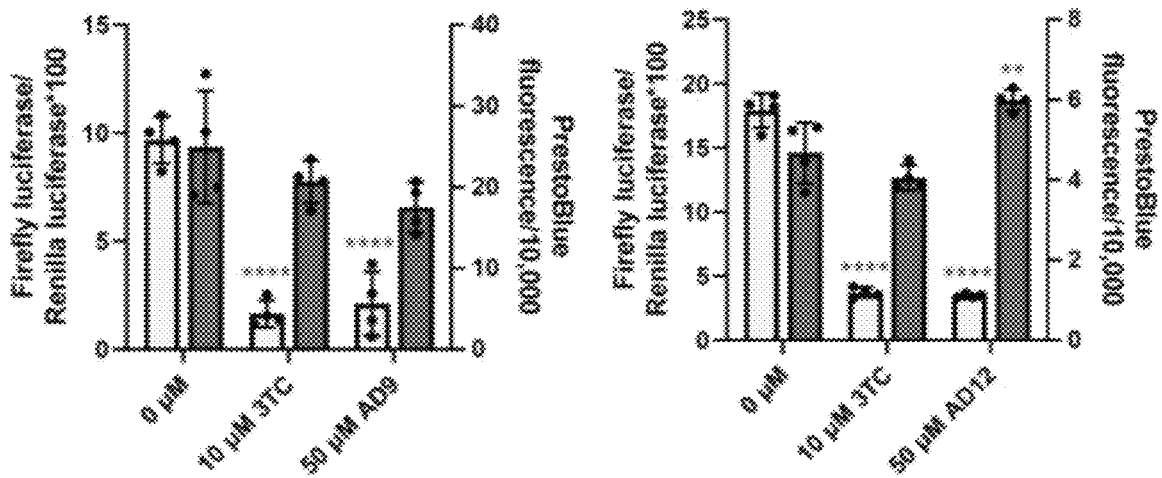
Figure 8D:
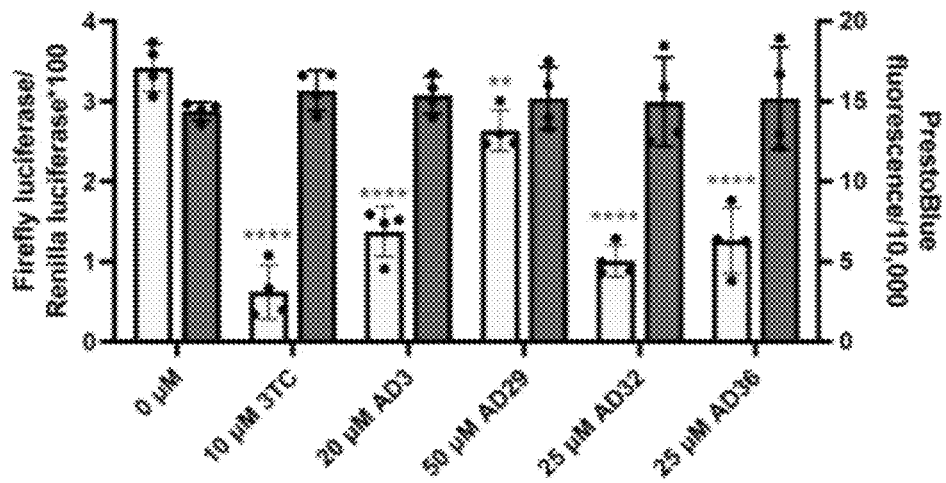
Figure 8E:
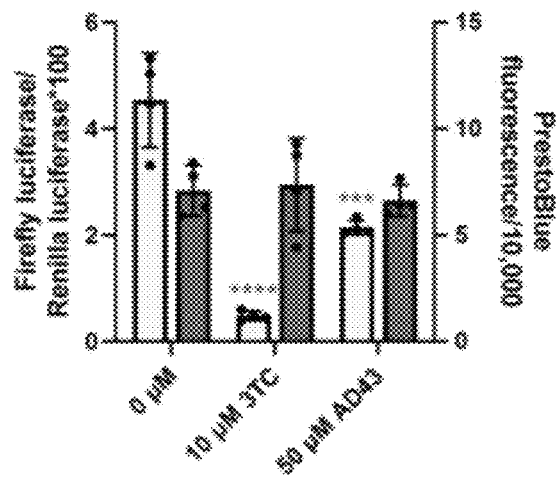
Figure 8F:
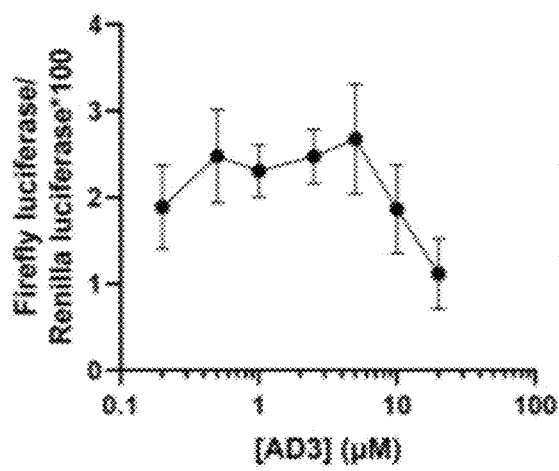
Figure 8G:
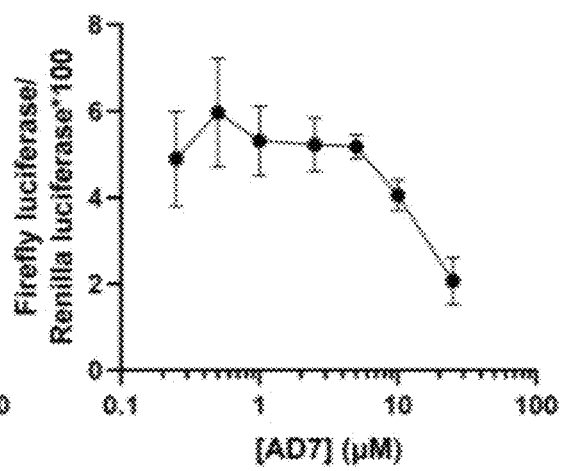
Figure 8H:
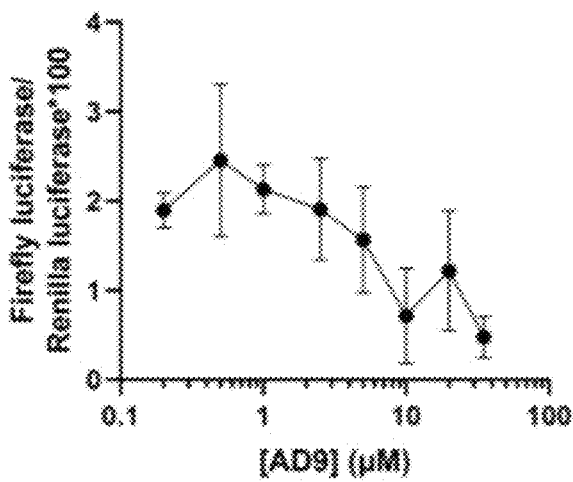
Figure 8I:
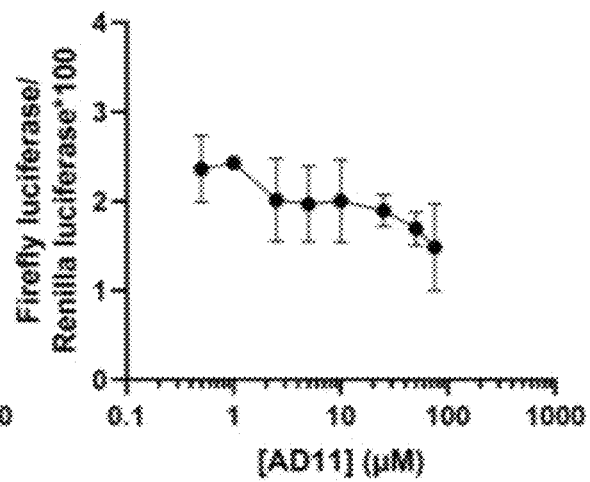
Figure 8J:
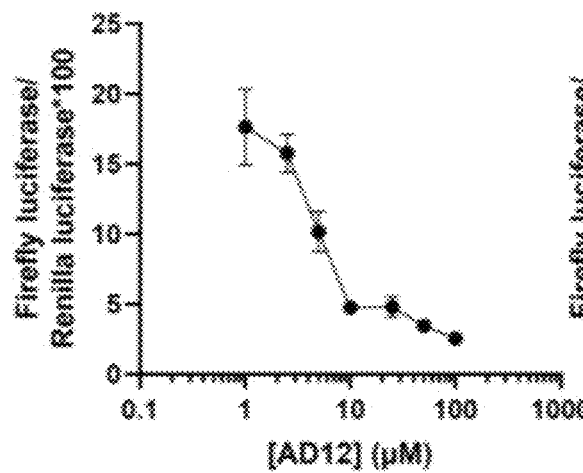
Figure 8K:
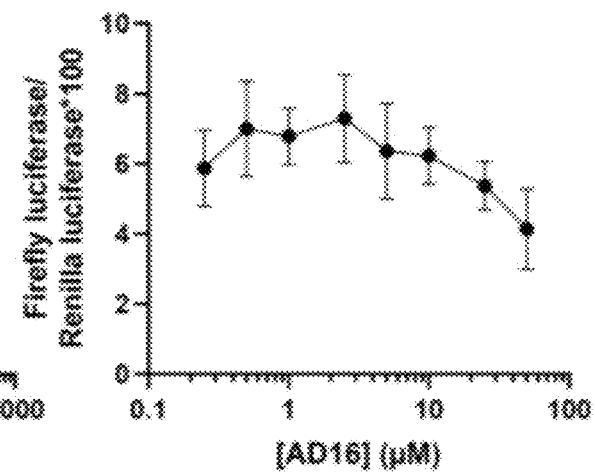
Figure 8L:
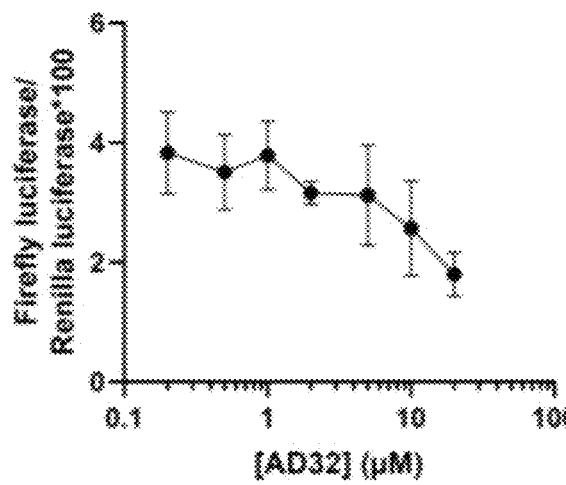
Figure 8M:
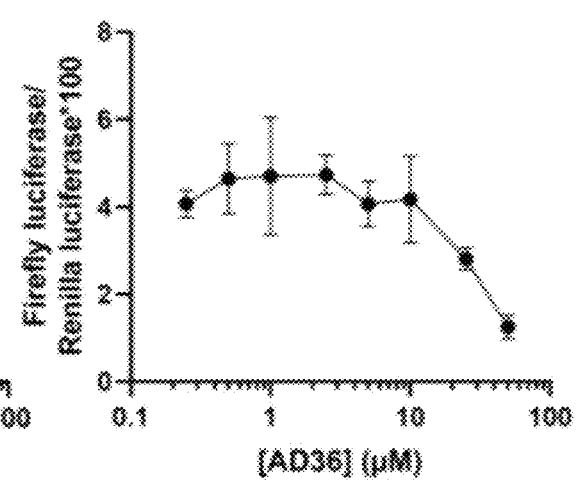

FIGS. 8A-8M show examples of EN inhibitors reducing L1 retrotransposition in cell culture. In FIGS. 8A-8E, retrotransposition (lighter bars) was measured in HeLa cells by expression of a Firefly luciferase reporter after a retrotransposition event normalized to Renilla luciferase activity. 3TC was included for comparison to RT inhibition. During compound screening, PrestoBlue Viability Reagent (darker bars) was used to test cytotoxicity; compounds with statistically significant cytotoxicity were subsequently tested at lower concentrations or excluded from further cellular testing. Statistical significance of the mean relative to no inhibitor control (0 µM) was determined by one-way ANOVA followed by Dunnett's multiple comparisons test using GraphPadPrism: *$p<0.05$, $p<0.01$, *$p<0.001$, ****$p<0.0001$. FIGS. 8F-8M show concentration-dependent inhibition for selected EN inhibitors as follows: AD3 (FIG. 8F), AD7 (FIG. 8G), AD9 (FIG. 8H), AD11 (FIG. 8I), AD12 (FIG. 8J), AD16 (FIG. 8K), AD32 (FIG. 8L), and AD36 (FIG. 8M). Results from 4 replicates for each treatment and concentration. Error bars=s.d.

Figure 9A:
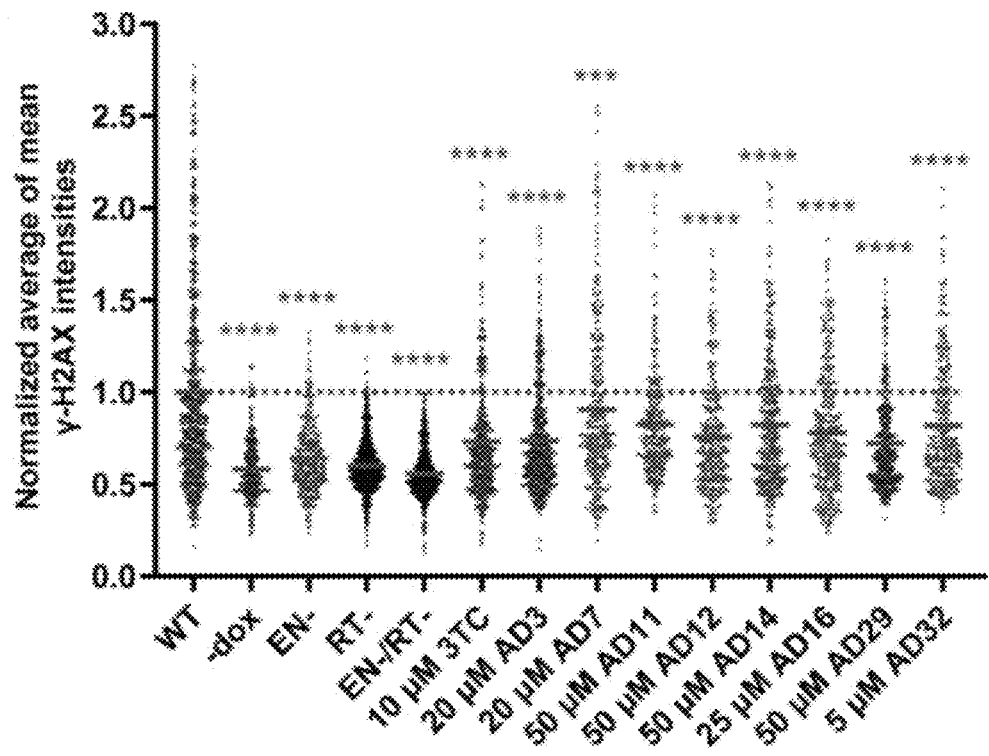
Figure 9B:
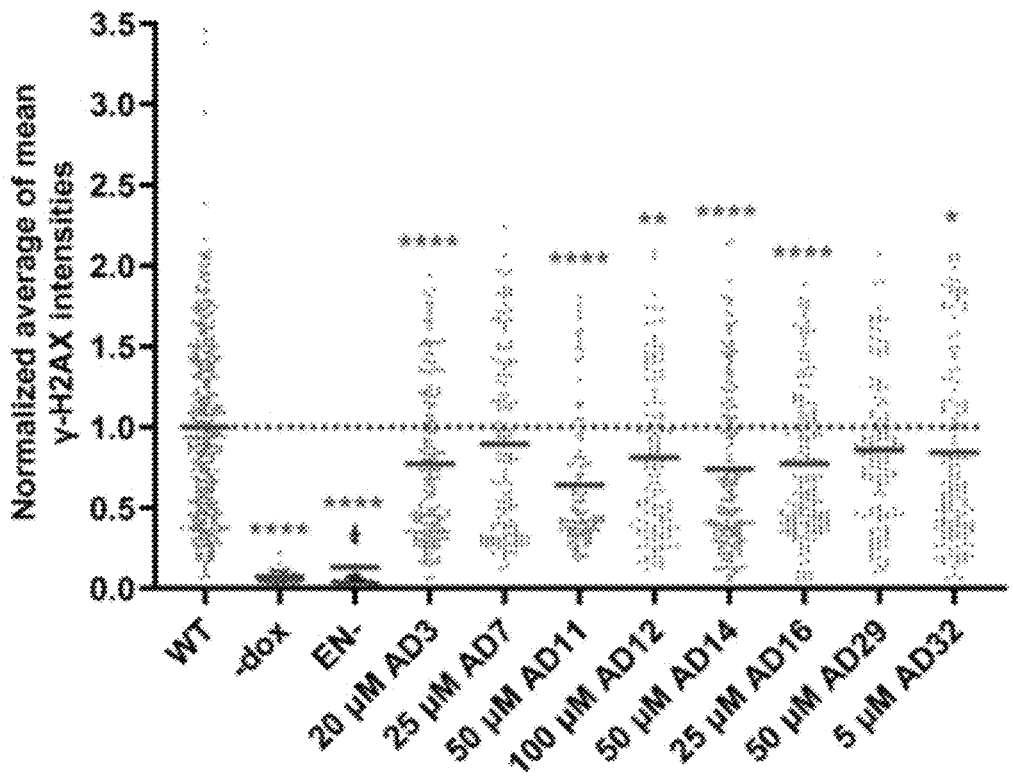
Figure 9C:
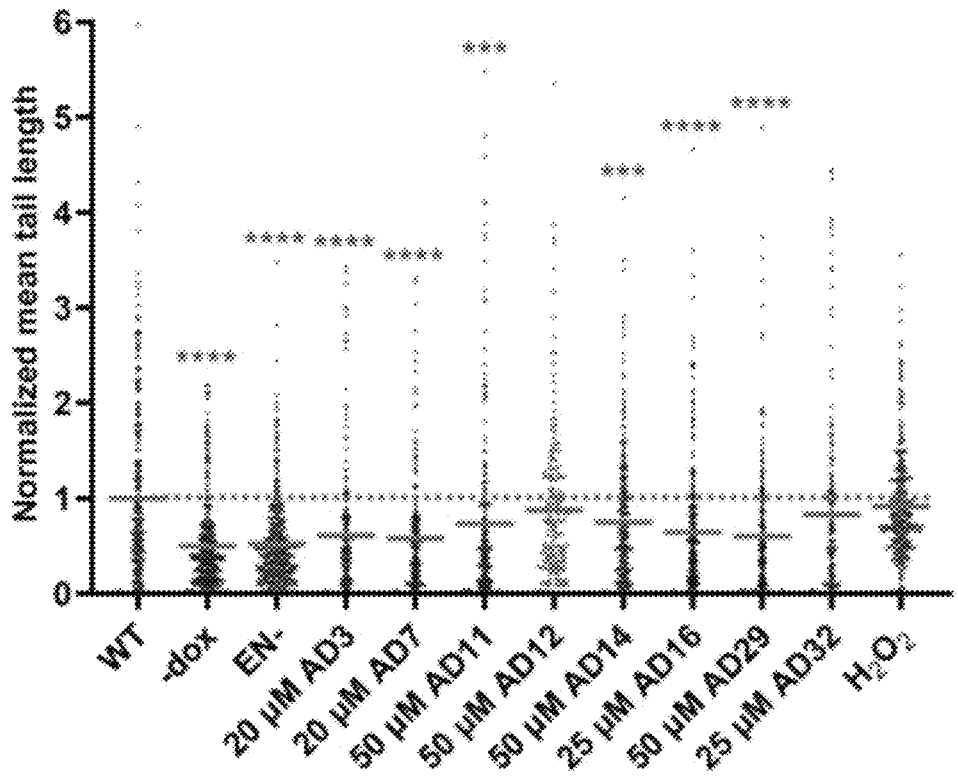
Figure 9D:
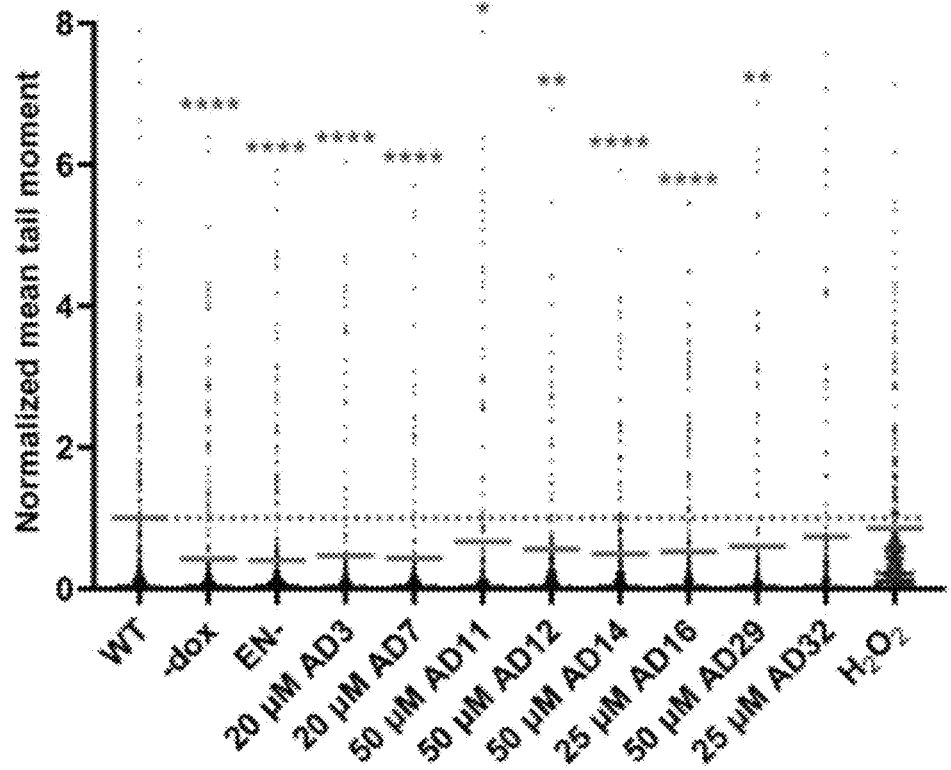

FIGS. 9A-9D show examples of EN inhibitors mitigating L1-induced DNA damage. HeLa Tet-On cell lines containing doxycycline-inducible FL or EN domain L1 expression constructs were generated for WT and mutant (EN-, H230A; RT-, D702Y; EN-/RT-, H230A/D702Y) L1. These cells were used for both the γ-H2AX immunofluorescence assay (FIG. 9A, FIG. 9B) and neutral comet assay (FIG. 9C, FIG. 9D). In FIG. 9A, average of mean γ-H2AX intensities of individual nuclei normalized to WT no inhibitor control (dotted line) for FL (n=254-752) or EN domain (FIG. 9B, n=56-325). Results are from at least 3 independent experiments per sample. Mean γH2AX intensity analysis was performed with CellProfiler. In FIG. 9C, mean comet tail length (FIG. 9C) and mean comet tail moment (FIG. 9D) normalized to EN WT no inhibitor control (dotted line) measured by OpenComet (n=174-391). Statistical significance of the mean (solid lines in FIG. 9A, FIG. 9B, FIG. 9C, and FIG. 9D) vs. WT was determined by one-way ANOVA followed by Dunnett's multiple comparisons test using GraphPad Prism: *$p<0.05$, $p<0.01$, *$p<0.001$, ****$p<0.0001$.

Figure 10F:
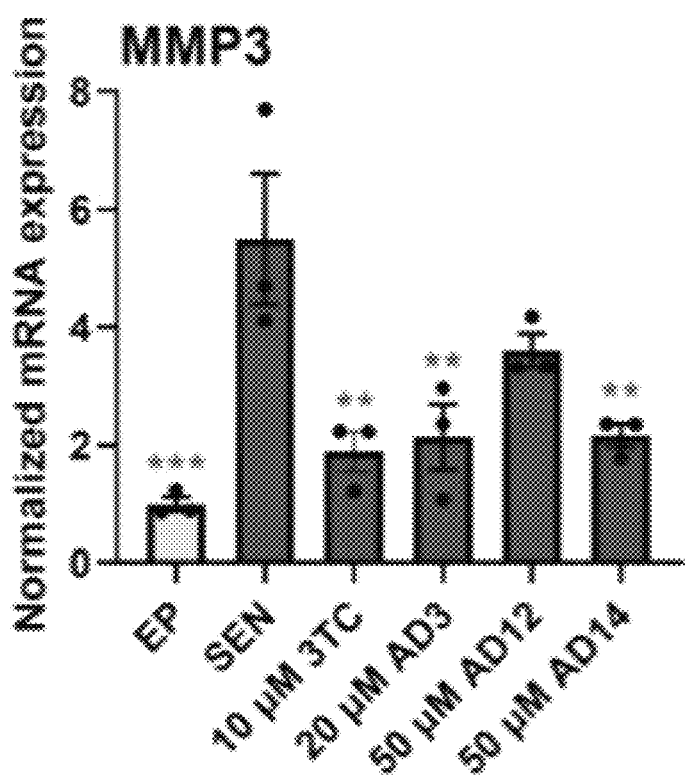

FIGS. 10A-10F show examples of EN inhibitors impacting inflammation markers in senescent cells. A timeline of senescent (SEN) culture generation and treatment is illustrated in FIG. 10A. Cells were passaged until they stopped dividing (SEN entry) and then maintained for 3 to 5 months, after which they were treated with inhibitors for 1 month before harvesting cultures for RNA. RT-qPCR of inflammatory markers for SEN cultures treated with inhibitors from 5 to 6 months (IL6 and IL1β, FIG. 10B, FIG. 10C), 4 to 5 months (CCL2 and IFNα, FIG. 10D, FIG. 10E), or 3 to 4 months (MMP3, FIG. 10F) SEN. All samples were normalized to early passage (EP). Statistical significance of the mean relative to SEN was determined by one-way ANOVA followed by Dunnett's multiple comparisons test using GraphPadPrism: *$p<0.05$, $p<0.01$, *$p<0.001$, ****$p<0.0001$. Error bars=s.e.

DETAILED DESCRIPTION OF THE INVENTION

It is to be appreciated that certain aspects, modes, embodiments, variations and features of the invention are described below in various levels of detail in order to provide a substantial understanding of the present invention.

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the compositions or processes are described as using specific materials or an order of individual steps, it is appreciated that materials or steps may be interchangeable such that the description of the invention may include multiple parts or steps arranged in many ways as is readily appreciated by one of skill in the art.

Definitions

The definitions of certain terms as used in this specification and the appended claims are provided below. Unless defined otherwise, all technical and scientific terms used herein generally have the same meaning as commonly understood by one of ordinary skill in the art to which this invention belongs.

As used in this specification and the appended claims, the singular forms "a," "an" and "the" include plural referents unless the content clearly dictates otherwise. For example, reference to "a cell" includes a combination of two or more cells, and the like.

The term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

The term "subject" refers to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human subjects. The human subject may be a pediatric, adult, or a geriatric subject. The human subject may be of either sex.

The terms "effective amount" and "therapeutically effective amount" include an amount sufficient to prevent or ameliorate a manifestation of disease or medical condition, such as an age-associated disorder. It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the subject, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the terms "treating" or "treatment" or "to treat" or "alleviating" or "to alleviate" refer to both (1) therapeutic measures that cure, slow down, lessen symptoms of, and/or halt progression of a diagnosed disease or infection and (2) prophylactic or preventative measures that prevent or slow the development of a disease or infection.

As used herein, the term "long-term" administration means that the therapeutic agent or drug is administered for a period of at least 12 weeks. This includes that the therapeutic agent or drug is administered such that it is effective over, or for, a period of at least 12 weeks and does not necessarily imply that the administration itself takes place for 12 weeks, e.g., if sustained release compositions or long-acting therapeutic agent or drug is used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

As used herein, the term "age-related inflammation" (or "age-associated inflammation") is an inflammation, typically a chronic, particularly a chronic systemic inflammation which occurs with increasing age. Such inflammation may be observed above the age of 30, 35 or 40 but typically is seen in subjects aged 45, 50, 55 or 60 or more. In many cases this may be a low-level inflammation.

As used herein, the term "chronic inflammation" means an inflammation (e.g., an inflammatory condition) that is of persistent or prolonged duration in the body of a subject. Generally speaking, this means an inflammatory response or condition of duration of 20, 25 or 30 days or more or 1 month or more, more particular of at least 2 or 3 months or more. Chronic inflammation leads to a progressive shift in the type of cells present at the site of inflammation. Chronic inflammation may be a factor in the development of a number of diseases or disorders, including particularly degenerative diseases, or diseases or conditions associated with loss of youthful function or aging.

As used herein, the term "systemic inflammation" is inflammation which is not confined to a particular tissue or site or location in the body. The inflammation may be generalized throughout the body. Systemic inflammation typically involves the endothelium and other organ systems.

As used herein, the term "low-level inflammation" (which term is used herein as synonymous with "low-grade inflammation") is characterized by a 2- to threefold increase in the systemic concentrations of cytokines such as TNFα, IL-6, and CRP, e.g., as measured in the plasma or serum. The increase may be relative to, or as compared with, normal concentrations or reference concentrations, for example concentrations as determined in a particular reference cohort or population of subjects, e.g., young subjects (e.g., young adults) or healthy subjects, for example subjects who are not suffering from any disease or condition, including any inflammatory disease, or who do not have inflammation. The increase may also be relative to the level of concentration in a subject prior to development of the inflammation. Low-level inflammation may be observed in the absence of overt signs or symptoms of disease. Thus, low-level inflammation may be sub-clinical inflammation. Alternatively, a subject with low-level inflammation may not have a clinically diagnosed condition or disease but may exhibit certain signs or symptoms of an inflammatory response or inflammatory condition. In other words, there may be signs or symptoms of the effect of inflammation in the body, but this may not yet have progressed to an overt or recognized disease.

As used herein, the term "cancer inflammation" is inflammation that occurs in the context of cancer and may alternatively be defined as "cancer-associated inflammation". Inflammation has been identified as a hallmark of cancer and may be necessary for tumorigenesis and maintenance of the cancer state. Cancer symptoms are associated with inflammation. Thus, a subject with cancer may have or exhibit inflammation, which can be a low-level or peripheral inflammation as discussed above, and in particular a chronic or systemic inflammation as discussed above.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-micro emulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4, 172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragées, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropyl methyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragées, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropyl methyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, micro-emulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art.[x]

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In other embodiments, the active compound will be administered once daily.

The patient receiving this treatment is any animal in need, including primates, in particular humans; and other mammals such as equines bovine, porcine, sheep, feline, and canine; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, l-ascorbic acid, l-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, l-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, l-pyroglutamic acid, salicylic acid, sebacic acid, stearic acid, succinic acid, sulfuric acid, l-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Role of Cellular Senescence in Aging and Age-Associated Diseases

Senescent cell accumulation with age contributes to sterile inflammation that underlies many age-associated diseases.[xi] Senescent cells undergo global chromatin changes, including an opening of constitutive heterochromatin containing retrotransposable elements (RTEs).[xii,xiii] RTEs are repetitive sequences that can copy themselves into new genomic locations using an RNA intermediate through the process of retrotransposition. The long interspersed nuclear element-1 (LINE-1 or L1) is the only active autonomously replicating RTE in humans, as it encodes the two catalytic activities required for its own retrotransposition: an endonuclease domain (EN) and a reverse transcriptase domain (RT).[xiv] Recent evidence has shown that L1 is derepressed in senescent cells and contributes to the proinflammatory senescence associated secretory phenotype (SASP).[xv] Furthermore, L1 RT inhibition by nucleoside reverse transcriptase inhibitors designed against the HIV RT, such as 3TC, reduces the SASP during prolonged senescence and in aged tissues.[xvi] FIG. 1 provides a flow chart outlining the molecular pathway of cellular senescence leading to age-associate, sterile inflammation, which are described in further detail below.

Recent evidence from our laboratory has shown that inhibition of the L1 RT domain by nucleoside reverse transcriptase inhibitors (NRTIs) originally designed against the HIV RT reduces the SASP in senescent cells in culture and in aging tissues. However, design of selective inhibitors for the L1 RT domain is currently not feasible due to the absence of structural information or knowledge about protein domain boundaries to enable recombinant protein purification. On the other hand, the structure of the L1 EN domain has been solved, allowing for structure-based inhibitor screening and design. The L1 EN is required for retrotransposition like the L1 RT, as L1 EN active site point mutations reduce retrotransposition similarly to those in the L1 RT. The L1 EN initiates L1 retrotransposition by nicking genomic DNA, which also results in double-strand breaks (DSBs) that can occur independent of L1 RT activity; it is estimated that the L1 EN can create 10-fold more DSBs than productive retrotransposition events. Additionally, inhibitors of the structurally homologous abasic site DNA repair endonuclease APE-1 have been characterized and provided initial candidate compounds. Based on these compounds, we developed inhibitors of the L1 EN that have shown efficacy in a biochemical assay and retrotransposition assay in cells. Therefore, the L1 EN is an advantageous target to inhibit L1 activity in the context of aging.

In the present invention, we have identified and characterized several L1 EN inhibitors with efficacy in a biochemical assay and a retrotransposition assay in cells.

Promotion of Age-Associated, "Sterile" Inflammation

Sterile inflammation, also known as inflammaging, is a hallmark of aging and a contributing factor to many age-related diseases.[xvii,xviii] As shown in our previous work, activation of L1 elements (and possibly other RTEs) promotes inflammaging, and that the L1 RT is a relevant target for the treatment of age-associated inflammation and disorders.

Accordingly, the present invention provides that L1 EN inhibitors can be used as "senostatic" drugs that are able to halt, or block the harmful effects of senescent cells, in particular the SASP, and prevent or reverse age-related inflammation and disorders.

Line-1 Endonuclease (L1 EN) Inhibitors

The inhibitors developed herein are the first inhibitors of the L1 EN domain to be discovered and the first of any retrotransposon-encoded endonuclease. While NRTIs inhibit the L1 RT, they result in off-target effects on mitochondrial polymerase γ. In addition, not all NRTIs are effective against the L1 RT and it is unclear why some are more effective than others in the absence of a L1 RT domain structure. In contrast, the L1 EN structure allows for virtual screening of large libraries of potential inhibitors to then test biochemically. The L1 EN can be easily purified recombinantly and assayed to allow for compound screening using a previously developed plasmid nicking biochemical activity assay. Additionally, a well-established L1 retrotransposition reporter assay can be used to test inhibitors in cells. Finally, L1 EN inhibitors will likely directly reduce DSBs based on previous studies that tested L1 EN point mutants. Therefore, L1 EN inhibitors were designed to specifically target the L1 EN given existing data, to not have off-target effects on mitochondrial polymerase γ, and to more effectively reduce DNA damage resulting from L1 activity.

Table 1 provides a list of the L1 EN inhibitors developed in the present invention. As described above, according to the methods of the present invention, L1 EN inhibitors can be used as "senostatic" drugs that are able to halt, or block the harmful effects of senescent cells, in particular the SASP, and prevent or reverse age-related inflammation and disorders.

TABLE 1

L1 EN INHIBITORS
Inhibitor ID, ZINC ID, and structure

AD1 (ZINC31769281)

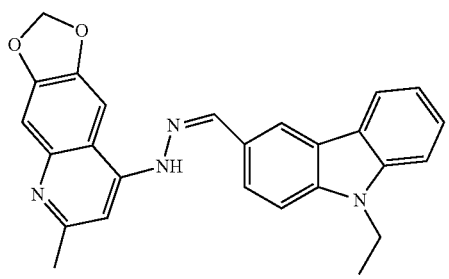 [SMILES: CCn1c2ccccc2c2cc(/C=N\Nc3cc(C)nc4cc5c(cc34)OCO5)ccc21]

TABLE 1-continued
L1 EN INHIBITORS
Inhibitor ID, ZINC ID, and structure
AD2 (ZINC89469886)
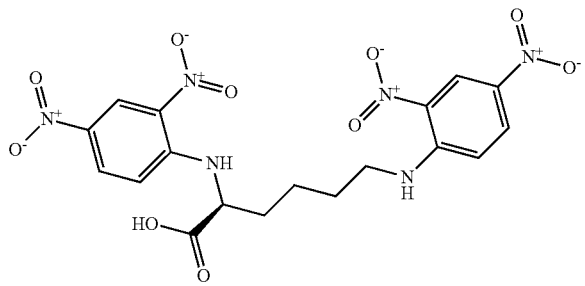 [SMILES: O=C(O)[C@H](CCCCNc1ccc([N+](=O)[O-])cc1[N+](=O)[O-])Nc1ccc([N+](=O)[O-])cc1[N+](=O)[O-]]
AD3 (ZINC100299612)
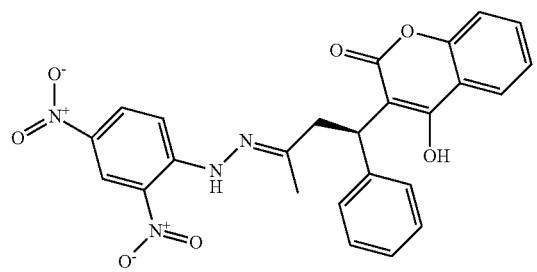 [SMILES: C/C(C[C@H](c1ccccc1)c1c(O)c2ccccc2oc1=O)=N\Nc1ccc([N+](=O)[O-])cc1[N+](=O)[O-]]
AD4 (ZINC25558200)
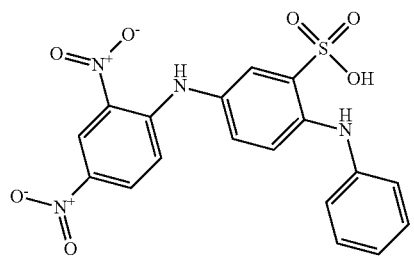 [SMILES: O=[N+]([O-])c1ccc(Nc2ccc(Nc3ccccc3)c(S(=O)(=O)O)c2)c([N+](=O)[O-])c1]
AD5 (ZINC100499350)
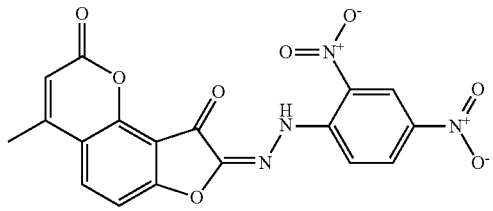 [SMILES: Cc1cc(=O)oc2c3c(ccc12)O/C(=N/Nc1ccc([N+](=O)[O-])cc1[N+](=O)[O-])C3=O]
AD6 (ZINC4550549)
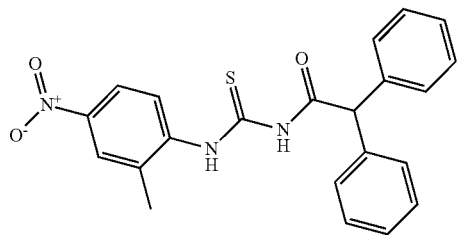 [SMILES: Cc1cc([N+](=O)[O-])ccc1NC(=S)NC(=O)C(c1ccccc1)c1ccccc1]

TABLE 1-continued
L1 EN INHIBITORS
Inhibitor ID, ZINC ID, and structure
AD7 (ZINC254379081)
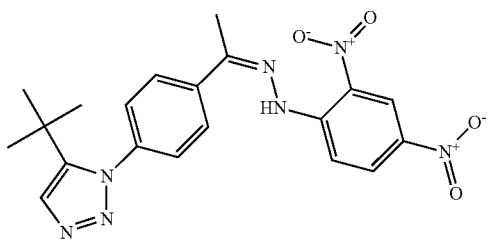 [SMILES: C/C(=N/Nc1ccc([N+](=O)[O-])cc1[N+](=O)[O-])c1ccc(-n2nncc2C(C)(C)C)cc1]
AD8 (ZINC4517567)
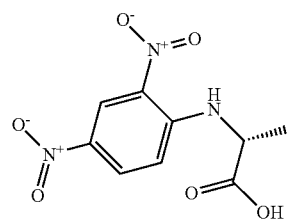 [SMILES: C[C@@H](Nc1ccc([N+](=O)[O-])cc1[N+](=O)[O-])C(=O)O]
AD9 (ZINC20677610)
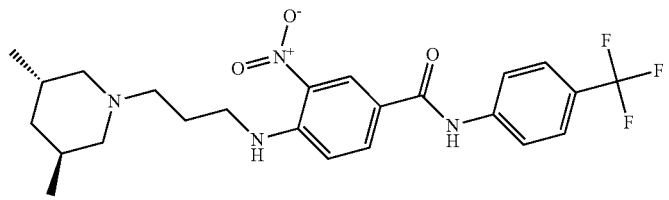 [SMILES: C[C@H]1C[C@H](C)CN(CCCNc2ccc(C(=O)Nc3ccc(C(F)(F)F)cc3)cc2[N+](=O)[O-])C1]
AD10 (ZINC1218780)
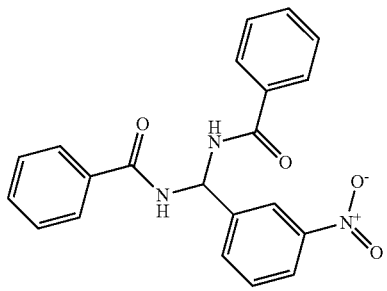 [SMILES: O=C(NC(NC(=O)c1ccccc1)c1cccc([N+](=O)[O-])c1)c1ccccc1]
AD11 (ZINC12428901)
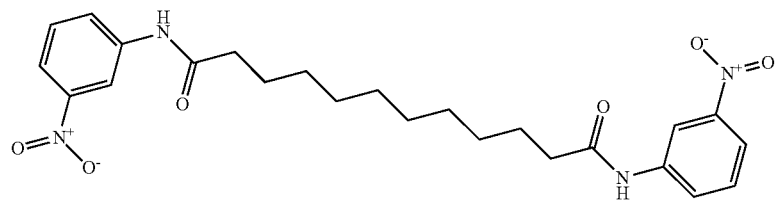 [SMILES: O=C(CCCCCCCCCCC(=O)Nc1cccc([N+](=O)[O-])c1)Nc1cccc([N+](=O)[O-])c1]

TABLE 1-continued
L1 EN INHIBITORS
Inhibitor ID, ZINC ID, and structure
AD12 (ZINC1482077)
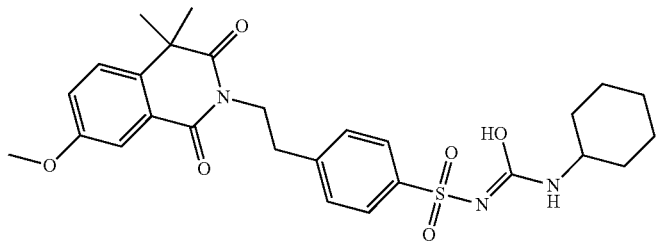 [SMILES: COc1ccc2c(c1)C(=O)N(CCc1ccc(S(=O)(=O)/N=C(\O)NC3CCCCC3)cc1)C(=O)C2(C)C]
AD13 (ZINC8398444)
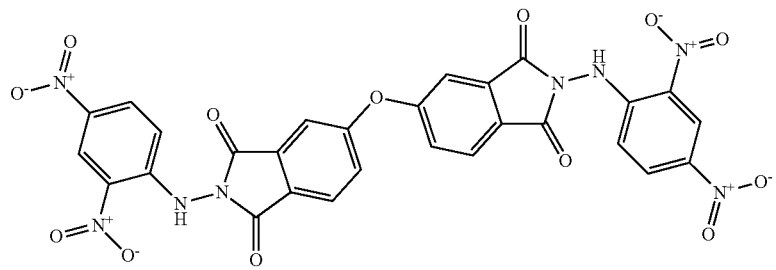 [SMILES: O=C1c2ccc(Oc3ccc4c(c3)C(=O)N(Nc3ccc([N+](=O)[O-])cc3[N+](=O)[O-])C4=O)cc2C(=O)N1Nc1ccc([N+](=O)[O-])cc1[N+](=O)[O-]]
AD14 (ZINC5758200)
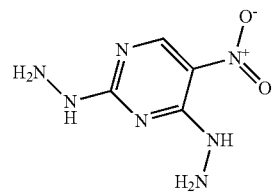
AD15 (ZINC537791)
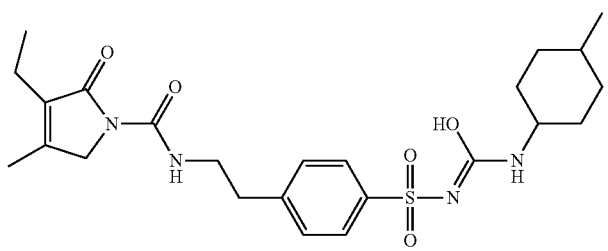
AD16 (ZINC33355084)
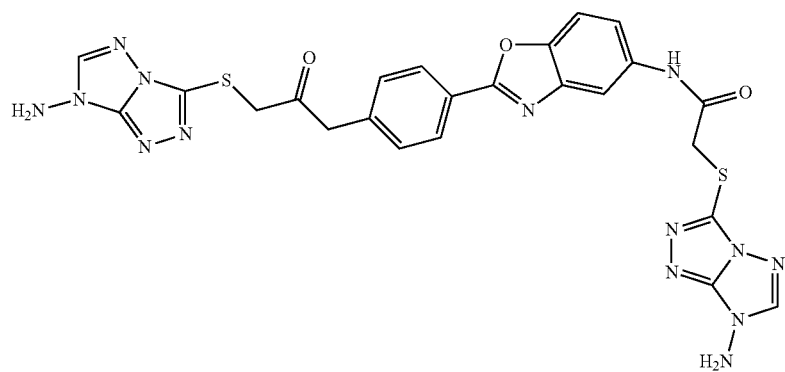 [SMILES: Nn1cnn2c(SCC(=O)Cc3ccc(-c4nc5cc(NC(=O)CSc6nnc7n(N)cnn67)ccc5o4)cc3)nnc12]

TABLE 1-continued
L1 EN INHIBITORS
Inhibitor ID, ZINC ID, and structure
AD17 (ZINC101372673)
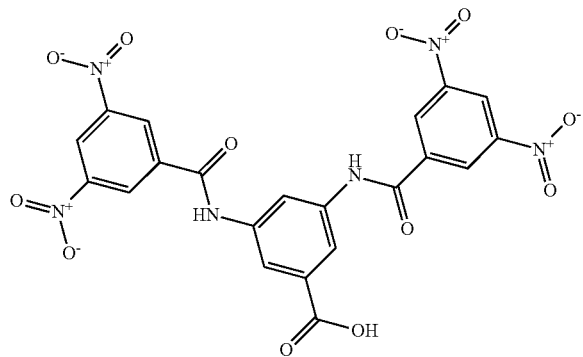 [SMILES: O=C(O)c1cc(NC(=O)c2cc([N+](=O)[O-])cc([N+](=O)[O-])c2)cc(NC(=O)c2cc([N+](=O)[O-])cc([N+](=O)[O-])c2)c1]
AD18 (ZINC9602289)
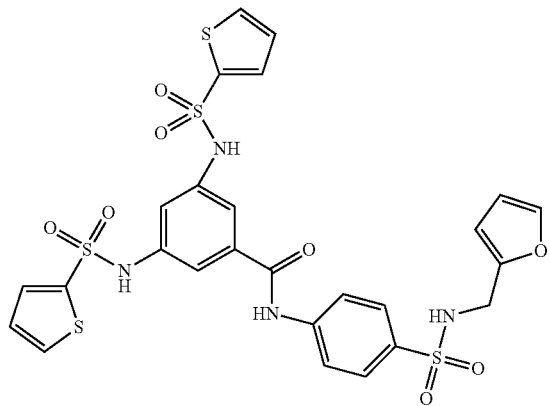 [SMILES: O=C(Nc1ccc(S(=O)(=O)NCc2ccco2)cc1)c1cc(NS(=O)(=O)c2cccs2)cc(NS(=O)(=O)c2cccs2)c1]
AD19 (ZINC150344228)
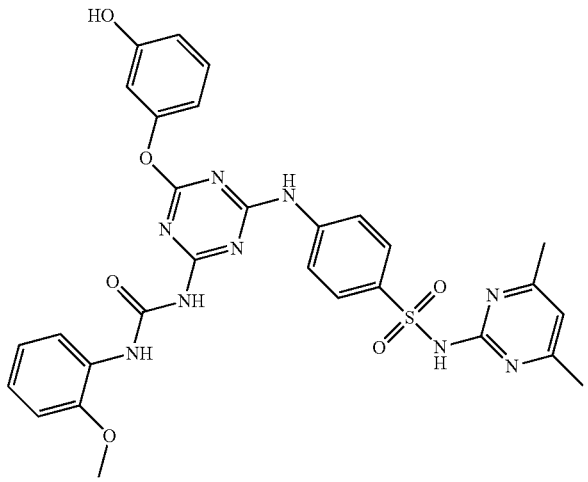 [SMILES: COc1ccccc1NC(=O)Nc1nc(Nc2ccc(S(=O)(=O)Nc3nc(C)cc(C)n3)cc2)nc(Oc2cccc(O)c2)n1]

TABLE 1-continued
L1 EN INHIBITORS
Inhibitor ID, ZINC ID, and structure
AD20 (ZINC8398012)
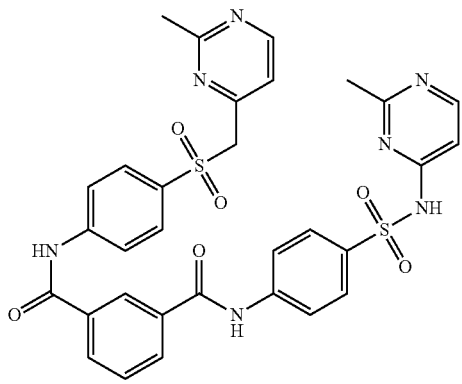 [SMILES: Cc1nccc(CS(=O)(=O)c2ccc(NC(=O)c3cccc(C(=O)Nc4ccc(S(=O)(=O)Nc5ccnc(C)n5)cc4)c3)cc2)n1]
AD22 (ZINC5944441)
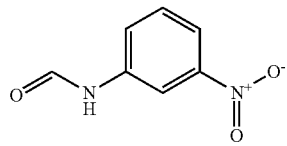 [SMILES: O=CNc1cccc([N+](=O)[O-])c1]
AD23 (ZINC4086624)
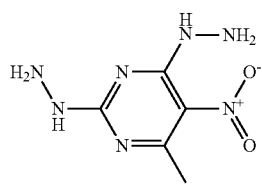
AD28 (ZINC9116296)
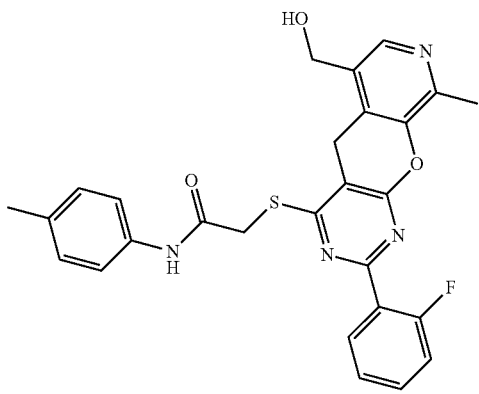
AD29 (ZINC33355295)
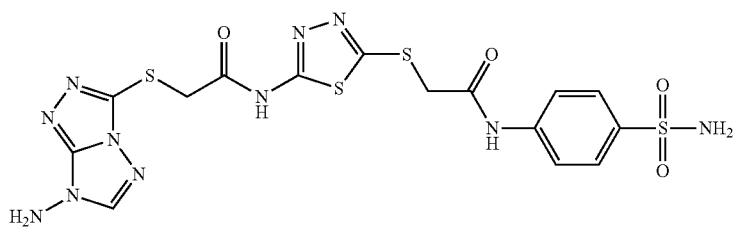 [SMILES: Nn1cnn2c(SCC(=O)Nc3nnc(SCC(=O)Nc4ccc(S(N)(=O)=O)cc4)s3)nnc12]

TABLE 1-continued
L1 EN INHIBITORS
Inhibitor ID, ZINC ID, and structure
AD32 (ZINC9056988)
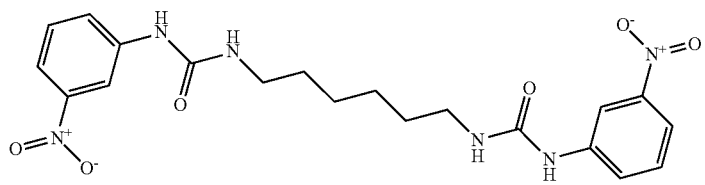 [SMILES: O=C(NCCCCCCNC(=O)Nc1cccc([N+](=O)[O-])c1)Nc1cccc([N+](=O)[O-])c1]
AD34 (ZINC33356589)
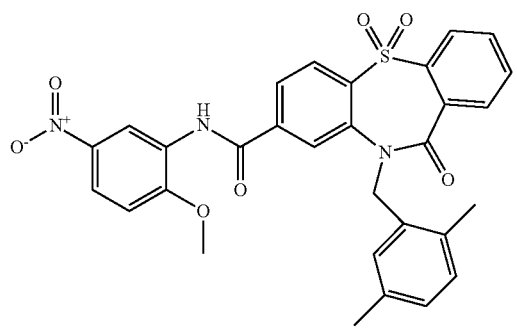 [SMILES: COc1ccc([N+](=O)[O-])cc1NC(=O)c1ccc2c(c1)N(Cc1cc(C)ccc1C)C(=O)c1ccccc1S2(=O)=O]
AD36 (ZINC16215374)
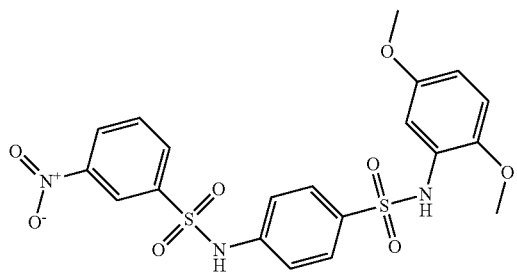 [SMILES: COc1ccc(OC)c(NS(=O)(=O)c2ccc(NS(=O)(=O)c3cccc([N+](=O)[O-])c3)cc2)c1]
AD37 (ZINC100007011)
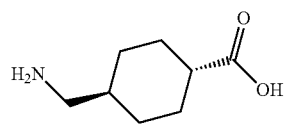 [SMILES: NC[C@H]1CC[C@H](C(=O)O)CC1]
AD38 (ZINC154737)
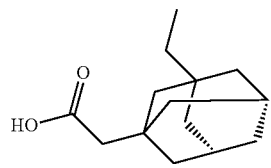 [SMILES: CCC12C[C@H]3C[C@@H](C1)CC(CC(=O)O)(C3)C2]

TABLE 1-continued
L1 EN INHIBITORS
Inhibitor ID, ZINC ID, and structure
AD39 (ZINC49550468)
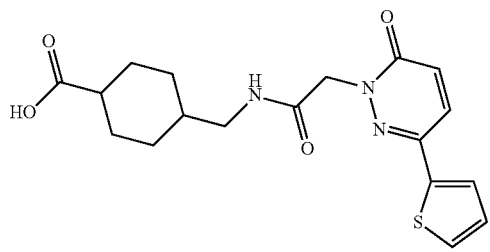 [SMILES: O=C(Cn1nc(-c2cccs2)ccc1=O)NCC1CCC(C(=O)O)CC1]
AD40 (ZINC3883091)
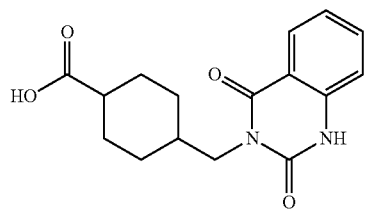 [SMILES: O=C(O)C1CCC(Cn2c(=O)[nH]c3ccccc3c2=O)CC1]
AD41 (ZINC425300)
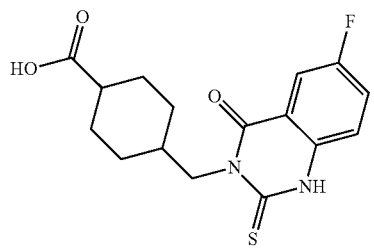 [SMILES: O=C(O)C1CCC(Cn2c(=S)[nH]c3ccc(F)cc3c2=O)CC1]
AD42 (ZINC238950702)
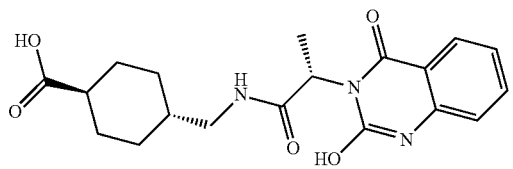 [SMILES: C[C@@H](C(=O)NC[C@H]1CC[C@H](C(=O)O)CC1)n1c(O)nc2ccccc2c1=O]
AD43 (ZINC238900190)
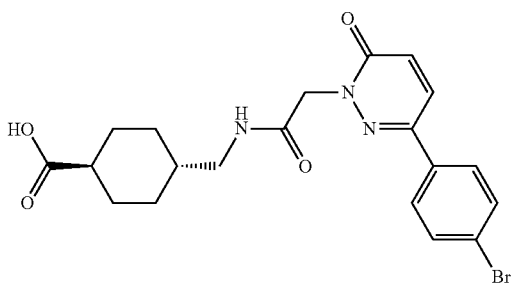 [SMILES: O=C(Cn1nc(-c2ccc(Br)cc2)ccc1=O)NC[C@H]1CC[C@H](C(=O)O)CC1]

TABLE 1-continued
L1 EN INHIBITORS
Inhibitor ID, ZINC ID, and structure
AD44 (ZINC950756015)
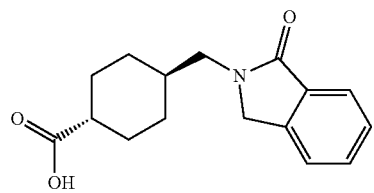 [SMILES: O=C1c2ccccc2CN1C[C@H]1CC[C@H](C(=O)O)CC1]
AD45 (ZINC952964257)
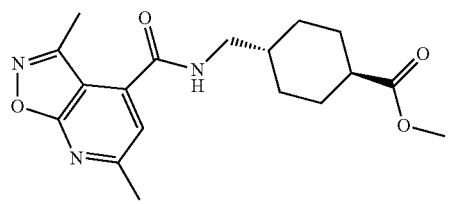 [SMILES: COC(=O)[C@H]1CC[C@H](CNC(=O)c2cc(C)nc3onc(C)c23)CC1]
AD46 (ZINC2029360)
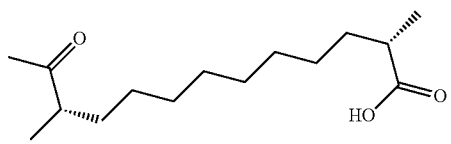 [SMILES: CC(=O)[C@@H](C)CCCCCCCC[C@H](C)C(=O)O]
AD47 (ZINC253387679)
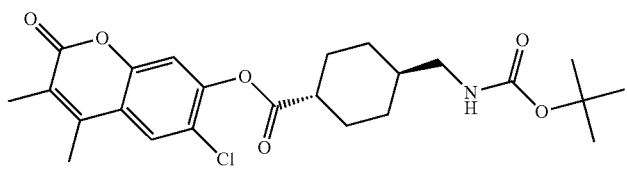 [SMILES: Cc1c(C)c2cc(Cl)c(OC(=O)[C@H]3CC[C@H](CNC(=O)OC(C)(C)C)CC3)cc2oc1=O]
AD48 (ZINC252695296)
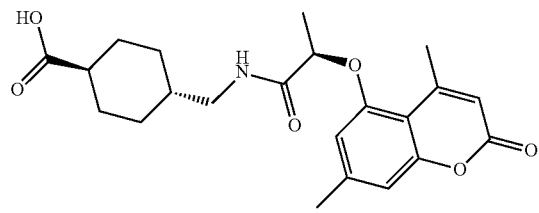 [SMILES: Cc1cc(O[C@H](C)C(=O)NC[C@H]2CC[C@H](C(=O)O)CC2)c2c(C)cc(=O)oc2c1]
AD49 (ZINC4747299)
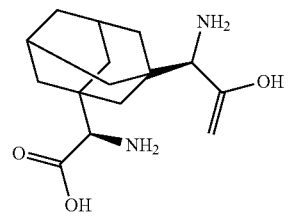

TABLE 1-continued

L1 EN INHIBITORS
Inhibitor ID, ZINC ID, and structure

AD50 (ZINC238924061)

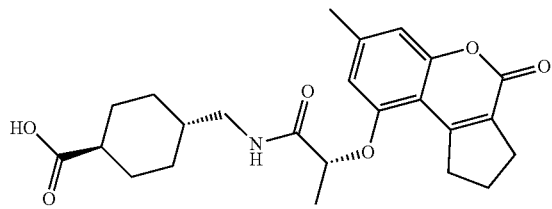 [SMILES: Cc1cc(O[C@H](C)C(=O)NC[C@H]2CC[C@H](C(=O)O)CC2)c2c3c(c(=O)oc2c1)CCC3]

AD51 (ZINC2204671)

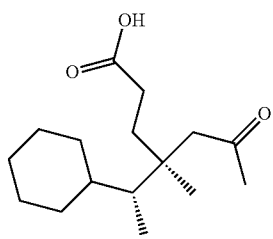 [SMILES: CC(=O)C[C@](C)(CCC(=O)O)[C@H](C)C1CCCCC1]

AD52 (ZINC242548640)

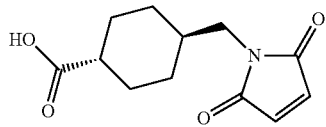 [SMILES: O=C1C=CC(=O)N1C[C@H]1CC[C@H](C(=O)O)CC1]

AD53 (ZINC242688517)

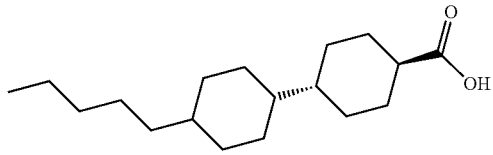 [SMILES: CCCCCC1CCC([C@H]2CC[C@H](C(=O)O)CC2)CC1]

AD54 (ZINC252585388)

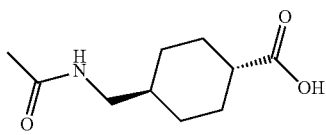

AD55 (ZINC245204959)

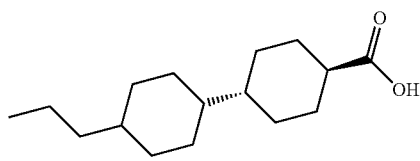 [SMILES: CCCC1CCC([C@H]2CC[C@H](C(=O)O)CC2)CC1]

In some embodiments, the subject undergoes long term administration of one or more L1 EN inhibitor, as defined herein. In one embodiment, the subject is treated for a period of at least 12 weeks. In many cases, long-term administration is for at least 4, 5, 6, 7, 8, 9 months or more, or for at least 1, 2, 3, 5, 7 or 10 years, or more.

Age-Associated Disorders

Given that cellular senescence is one of the major drivers of organismal aging and aging-associated diseases,[xix] the methods of the present invention can be used to prevent or treat disorders or diseases that have been associated with cellular senescence, in particular in which the presence of senescent cells is likely to have a deleterious effect, by the administration of one or more senostatic L1 EN inhibitor.

Disorders or diseases that have been associated with cellular senescence include, but are not limited to, Alzheimer's disease,[xx] amyotrophic lateral sclerosis (ALS), atherosclerosis,[xxi] Huntington's disease, vision loss, hearing loss, peripheral degenerative diseases, cardiovascular dysfunction,[xxii] atherosclerosis, frontotemporal dementia (FTD), multiple sclerosis (MS), Aicardi Goutiere's syndrome, progressive supra nuclear palsy (PSP), chemotherapy-induced adverse effects (e.g., bone marrow suppression, cardiotoxicity, cancer recurrence, blood clots, fatigue),[xxiii] hematopoietic stem cell function,[xxiv] osteoarthritis,[xxv] osteoporosis,[xxvi] osteoporosis, Parkinson's disease,[xxvii] physical function,[xxviii] pulmonary fibrosis,[xxix] skin aging, wound healing, and/or tissue regeneration.[xxx]

Methods of Treating, Preventing and Reversing Age-Associated Inflammation with L1 EN Inhibitors Provided is a method for treating, preventing and reversing age-associated inflammation in a patient in need thereof by administering a L1 EN inhibitor to a patient in need thereof. The age-associated inflammation may be in a patient having Alzheimer's disease, amyotrophic lateral sclerosis, Parkinson's disease, Huntington's disease, vision loss, hearing loss, peripheral degenerative diseases, and cardiovascular dysfunction.

In one embodiment is provided a method for delaying or reversing the progression of the underlying pathology of an age-associated inflammatory disorder, comprising administering to a patient in need thereof a therapeutically effective amount of at least one L1 EN inhibitor. In some embodiments, the patient experiences a decrease in one or more symptoms of Alzheimer's disease compared to before the first administration of the L1 EN inhibitor to the patient. In a further embodiment, the one or more L1 EN inhibitors inhibit L1 reverse transcriptase activity in a cell, e.g., a brain cell, of the patient.

In another embodiment, provided is a method for preventing the onset of an age-associated inflammatory disorder in a patient suspected of having mild cognitive impairment, comprising administering at least one L1 EN inhibitor to a patient in need thereof.

In some embodiments, the one or more L1 EN inhibitors are selected from AD2, AD3, AD4, AD5, AD6, AD7, AD8, AD9, AD10, AD11, AD12, AD13, AD14, AD16, AD17, AD18, AD19, AD20, AD22, AD23, AD28, AD29, AD32, AD34, AD36, AD37, AD38, AD39, AD40, AD41, AD42, AD43, AD44, AD45, AD46, AD47, AD48, AD49, AD50, AD51, AD52, AD53, AD54, and AD55. In some embodiments, the one or more L1 EN inhibitors are selected from AD22, AD23, AD28, AD29, AD32, AD34, AD36, AD37, AD38, AD39, AD40, AD41, AD42, AD43, AD44, AD45, AD46, AD47, AD48, AD49, AD50, AD51, AD52, AD53, AD54, and AD55. In some embodiments, the one or more L1 EN inhibitors are selected from AD22, AD23, AD28, AD29, AD32, AD34, and AD36. In some embodiments, the one or more L1 EN inhibitors are selected from AD37, AD38, AD39, AD40, AD41, AD42, AD43, AD44, AD45, AD46, AD47, AD48, AD49, AD50, AD51, AD52, AD53, AD54, and AD55.

The amounts effective can be determined with no more than routine experimentation. For example, amounts effective may range from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. In other embodiments, the dosage is 1 mg-500 mg. In some embodiments, the dosage is 10, 20, 30, 40, 50, 60, 70, 80, 90, 100, 110, 120, 130, 140, or 150 mg. These doses may be unitary or divided and may be administered one or more times per day. The above dosages are exemplary of the average case, but there can be individual instances in which higher or lower dosages are merited, and such are within the scope of this disclosure. In practice, the physician determines therapeutically effective amounts and the actual dosing regimen that is most suitable for an individual subject, which can vary with the age, weight, and response of the particular subject.

The L1 EN inhibitor may be administered once, twice or three times per day for 1 day to the end of life, or for 1 day to 1, 2, 3, 4, 5, 6, 7, 8, 9, or 10 or more years, or until the L1 EN inhibitor causes unacceptable side effects or is no longer useful.

The patient is monitored for changes in the symptoms of the age-associated inflammatory disease. In one embodiment, there is a reduction in the symptoms. In another embodiment, the symptoms remain about the same and there is no evidence of progression. In connection with Alzheimer's disease, such symptoms include memory loss, misplacing items, forgetting the names of places or objects, repeating questions, being less flexible, confusion, disorientation, obsessive behavior, compulsive behavior, delusions, aphasia, disturbed sleep, mood swings, depression, anxiety, frustration, agitation, difficulty in performing spatial tasks, agnosia, difficulty with ambulation, weight loss, loss of speech, loss of short term memory or loss of long term memory. Methods for monitoring and quantifying any change of these symptoms can be carried out by routine methods or by routine experimentation.

In one embodiment, symptoms of mild cognitive impairment and any change in the symptoms of Alzheimer's disease is determined using the criteria set forth in DSM-5. In another embodiment, symptoms of mild cognitive impairment and the any change in the symptoms of Alzheimer's disease is determined using the Clinician's Interview-Based Impression of Change (CIBIC-plus). In another embodiment, symptoms of mild cognitive impairment and any change in symptoms is determined using the Clinician's Interview-Based Impression of Change (CIBIC-plus).

Any change in symptoms may be monitored for 1-36 months or more, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months.

In another embodiment, the patient is monitored for a change in the underlying pathology of Alzheimer's disease. In one embodiment, there is a reduction in the underlying pathology. In another embodiment, the underlying pathology remains about the same and there is no evidence of progression.

In some embodiments, any change in the underlying pathology is identified by detection of a biomarker before and after the administration of the L1 EN inhibitor. In one embodiment, the biomarker is β-amyloid or Tau protein. In another embodiment, the biomarker is detected by PET imaging. In another embodiment, the underlying pathology is identified by measurement of brain volume before and after the L1 EN inhibitor administration.

In some embodiments, the decrease of the underlying pathology is reversed or delayed for at 1-36 months, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months after the first administration of L1 EN inhibitor.

In some embodiments, the patient is also administered at least one second therapeutic agent useful for the treatment of the symptoms of an age-associated inflammatory disorder. In one embodiment, the patient is administered at least one second therapeutic agent useful for the treatment of Alzheimer's disease. In some embodiments, the at least one second therapeutic agent is donepezil, galantamine, rivastigmine, or memantine. In another embodiment, the at least one second therapeutic agent is an antibody that binds to β-amyloid or Tau protein. In another embodiment, the antibody binds to β-amyloid and is bapineuzumab. In another embodiment, the antibody binds to Tau protein and is ABBV-8E12. In another embodiment, the at least one second therapeutic agent is a vaccine against β-amyloid or Tau protein. In another embodiment, the at least one second therapeutic agent is an agent that reduces or alters the brain content of β-amyloid or Tau. In another embodiment, the second therapeutic agent reduces or alters the brain content of β-amyloid and is a β-secretase 1 (BACE) inhibitor. In another embodiment, the BACE inhibitor is CTS-21166, verubecestat (MK-8931), lanabecestat (AZD3293) or LY2886721. In another embodiment, the second agent reduces or alters the brain content of β-amyloid or Tau alters the brain content of Tau and is nicotinamide, or MPT0G211.

The at least one L1 EN inhibitor and at least one second therapeutic agent may be administered separately or together as part of a unitary pharmaceutical composition.

When the age-associated inflammatory disorder is ALS, the patient may be administered at least one second agent useful for the treatment of the symptoms of ALS. In some embodiments, the at least one second agent is an integrase inhibitor. In some embodiments, the integrase inhibitor is raltegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-25 870810, MK-0518, BMS-538158, or GSK364735C.[xxxi]

The patient may be monitored for improvement of the symptoms of ALS. Such symptoms include one or more of the following: difficulty walking or doing normal daily activities, tripping and falling, weakness of the legs, feet or ankles, hand weakness or clumsiness, slurred speech or trouble swallowing, muscle cramps, twitching in the arms, shoulders or tongue, inappropriate crying, cognitive changes, and behavior changes.

Any change in symptoms may be monitored for 1-36 months or more, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. In some embodiments, the decrease of the underlying pathology is reversed or delayed for at 1-36 months or longer, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months after the first administration of the L1 EN inhibitor.

Salts, Pharmaceutical Compositions, and Kits

The methods of the present disclosure can be accomplished by administering an at least one L1 EN inhibitor as the neat compound or as a pharmaceutical composition. Administration of a pharmaceutical composition, or neat compound of an L1 EN inhibitor, can be performed before or after the clinical diagnosis of a disorder associated with age-associated inflammation. Typically, the pharmaceutical compositions are sterile, and contain no toxic, carcinogenic, or mutagenic compounds that would cause an adverse reaction when administered.

Further provided are kits comprising at least one L1 EN inhibitor and, optionally, at least one second therapeutic agent useful for the treatment or prevention of a disorder associated with age-associated inflammation, packaged separately or together, and an insert having instructions for using these active agents. In one embodiment, the at least one L1 EN inhibitor is packaged alone together with instructions to administered together with the at least one second therapeutic agent. The at least one L1 EN inhibitor and the at least one second therapeutic agent can be administered simultaneously or sequentially to achieve the desired effect. In addition, the L1 EN inhibitor and the at least one second therapeutic agent can be administered from a single composition or two separate compositions.

Examples of the at least one second therapeutic agents useful for the treatment of Alzheimer's disease that may be in the kit include donepezil, galantamine, rivastigmine and memantine. Other optional therapeutic agents that may be in the kit include an antibody that binds to β-amyloid or Tau protein. In one embodiment, the antibody binds to β-amyloid and is bapineuzumab. In another embodiment, the antibody binds to Tau and is ABBV-8E12.

In another embodiment, the kit may contain least one second therapeutic agent that is a vaccine against β-amyloid or Tau protein.

In another embodiment, the kit may contain at least one second therapeutic agent that reduces or alters the brain content of β-amyloid or Tau protein. In some embodiments, the second therapeutic agent that alters or reduces the brain content of β-amyloid is a β-secretase 1 (BACE) inhibitor. In some embodiment, the BACE inhibitor is CTS21166, verubecestat (MK-8931), lanabecestat (AZD3293) or LY2886721, each of which have been in clinical trials for the treatment of Alzheimer's disease.

In another embodiment, the kit may contain a second agent that reduces or alters the brain content of Tau and is nicotinamide, or MPT0G211.

In some embodiments, the patient has ALS and the kit further comprises at least one second agent useful for the treatment of ALS. In other embodiments, the L1 EN inhibitor is packaged alone together with instructions to administer at least one second therapeutic agent for the treatment of ALS. In some embodiments, the at least one second therapeutic agent for the treatment of ALS is edaravone or riluzole.

In some embodiments, the at least one second agent is an integrase inhibitor. In some embodiments, the integrase inhibitor is raltegravir, curcumin, derivatives of curcumin, chicoric acid, derivatives of chicoric acid, 3,5-dicaffeoylquinic acid, derivatives of 3,5dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-25 870810, MK-0518, BMS-538158, or GSK364735C.[xxxii]

The second therapeutic agent is administered in an amount to provide its desired therapeutic effect. The effective dosage range for each optional therapeutic agent is known in the art, and the optional therapeutic agent is administered to an individual in need thereof within such established ranges.

The present disclosure encompasses the preparation and use of salts of L1 EN inhibitors. As used herein, a "pharmaceutically acceptable salt" refers to salts or zwitterionic forms of the L1 EN inhibitors. Salts of L1 EN inhibitors can be prepared during the final isolation and purification of the compounds or separately by reacting the compound with a suitable acid. The pharmaceutically acceptable salts of L1 EN inhibitors can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of L1 EN inhibitors include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2 naphthalenesulfonate, oxalate, pamoate, pectinate, persulfate, 3 phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p toluenesulfonate salts. In addition, available amino groups present in the L1 EN inhibitors can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to L1 EN inhibitors appearing herein is intended to include the L1 EN inhibitors as well as pharmaceutically acceptable salts, hydrates, or solvates thereof.

The present disclosure encompasses the preparation and use of solvates of L1 EN inhibitors. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g., a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. L1 EN inhibitors can be present as solvated forms with a pharmaceutically acceptable solvent, such as water, methanol, and ethanol, and it is intended that the disclosure includes both solvated and unsolvated forms of L1 EN inhibitors. One type of solvate is a hydrate. A "hydrate" relates to a particular subgroup of solvates where the solvent molecule is water. Solvates typically can function as pharmacological equivalents. Preparation of solvates is known in the art. See, e.g., Caira et al. (2004),[xxxiii] which describes the preparation of solvates of fluconazole with ethyl acetate and with water. Similar preparation of solvates, hemisolvates, hydrates, and the like are described by Van Tonder et al. (2004)[xxxiv] and Bingham et al. (2001).[xxxv] A typical, non-limiting, process of preparing a solvate would involve dissolving the at least one L1 EN inhibitor or at least one second therapeutic agent in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvate in a crystal of the solvate.

The at least one L1 EN inhibitor and at least one second therapeutic agent typically are administered in admixture with a pharmaceutical carrier to give a pharmaceutical composition selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of the at least one L1 EN inhibitor and at least one second therapeutic agent.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the at least one L1 EN inhibitor and/or at least one second therapeutic agent is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of the at least one L1 EN inhibitor and at least one second therapeutic agent. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of the at least one L1 EN inhibitor and at least one second therapeutic agent.

When a therapeutically effective amount of the at least one L1 EN inhibitor and at least one second therapeutic agent is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

The at least one L1 EN inhibitor and at least one second therapeutic agent can be readily combined with pharmaceutically acceptable carriers well-known in the art. Standard pharmaceutical carriers are described in Remington's Pharmaceutical Sciences.[xxxvi] Such carriers enable the active agents to be formulated as tablets, pills, dragees, capsules, liquids, gels, syrups, slurries, suspensions and the like, for oral ingestion by a subject to be treated. Pharmaceutical preparations for oral use can be obtained by adding the at least one L1 EN inhibitor and/or the at least one second therapeutic agent to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The at least one L1 EN inhibitor and at least one second therapeutic agent can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of the at least one L1 EN inhibitor and at least one second therapeutic agent can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The at least one L1 EN inhibitor and at least one second therapeutic agent also can be formulated in rectal compositions, such as suppositories or retention enemas, e.g., containing conventional suppository bases. In addition to the formulations described previously, the at least one L1 EN inhibitor and at least one second therapeutic agent also can be formulated as a depot preparation. Such long-acting formulations can be administered by implantation (for example, subcutaneously or intramuscularly) or by intramuscular injection. Thus, for example, the at least one L1 EN inhibitor and at least one second therapeutic agent can be formulated with suitable polymeric or hydrophobic materials (for example, as an emulsion in an acceptable oil) or ion exchange resins.

In particular, the at least one L1 EN inhibitor and at least one second therapeutic agent can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The at least one L1 EN inhibitor and at least one second therapeutic agent also can be injected parenterally, for example, intravenously, intramuscularly, subcutaneously, or intracoronarily. For parenteral administration, the at least one L1 EN inhibitor and at least one second therapeutic agent are typically used in the form of a sterile aqueous solution which can contain other substances, for example, salts or monosaccharides, such as mannitol or glucose, to make the solution isotonic with blood.

Some embodiments of the technology described herein can be defined according to any of the following numbered features 1-39 below:

1. A method for treating, preventing and/or reversing age-associated inflammation in a patient in need thereof comprising administering a therapeutically effective amount of a long interspersed nuclear element-1 (L1) endonuclease (EN) inhibitor to the patient, wherein the L1 EN inhibitor is selected from the group consisting of: AD20, AD22, AD23, AD28, AD29, AD32, AD34, AD36, AD37, AD38, AD39, AD40, AD41, AD42, AD43, AD44, AD45, AD46, AD47, AD48, AD49, AD50, AD51, AD52, AD53, AD54, and AD55.
2. The method of paragraph 1, wherein the age-associated inflammation is associated with an upregulation of L1, an accumulation of cytoplasmic L1 cDNA, an activation of a type-I interferon (IFN-I) response, and a reinforcement of a Senescence-Associated Secretory Phenotype (SASP) pro-inflammatory state.
3. The method of paragraph 2, wherein the L1 EN inhibitor is administered in an amount sufficient to prevent or reverse the upregulation of L1.
4. The method of paragraph 2, wherein the L1 EN inhibitor is administered in an amount sufficient to prevent or reverse the accumulation of cytoplasmic L1 cDNA.
5. The method of paragraph 2, wherein the L1 EN inhibitor is administered in an amount sufficient to prevent or reverse the activation of the IFN-I response.
6. The method of paragraph 2, wherein the L1 EN inhibitor is administered in an amount sufficient to prevent or reverse the SASP pro-inflammatory state.
7. The method of paragraph 1, wherein the age-associated inflammation is in a patient having Alzheimer's disease, amyotrophic lateral sclerosis (ALS), Parkinson's disease, Huntington's disease, vision loss, hearing loss, peripheral degenerative diseases, or cardiovascular dysfunction, frontotemporal dementia (FTD), multiple sclerosis (MS), Aicardi Goutiere's syndrome, progressive supra nuclear palsy (PSP), osteoarthritis, skin aging, atherosclerosis, chemotherapy-induced adverse effects, hematopoietic stem cell function, osteoporosis, physical function, and/or pulmonary fibrosis, or in a patient in need of wound healing or tissue regeneration.
8. The method of any one of paragraphs 1-6, wherein the age-associated inflammation is in a patient having Alzheimer's disease.
9. The method of any one of paragraphs 1-6, wherein the age-associated inflammation is in a patient having ALS.
10. A method for delaying or reversing the progression of the underlying pathology of a disorder caused by age-associated inflammation, comprising administering to a patient in need thereof a therapeutically effective amount of an L1 EN inhibitor.
11. The method of paragraph 10, wherein the patient has Alzheimer's disease or ALS and experiences a decrease in one or more symptoms of Alzheimer's disease or ALS compared to before the first administration to the patient.
12. The method of paragraph 11, wherein the patient has Alzheimer's disease and the one or more symptoms comprise memory loss, misplacing items, forgetting the names of places or objects, repeating questions, being less flexible, confusion, disorientation, obsessive behavior, compulsive behavior, delusions, aphasia, disturbed sleep, mood swings, depression, anxiety, frustration, agitation, difficulty in performing spatial tasks, agnosia, difficulty with ambulation, weight loss, loss of speech, loss of short term memory or loss of long term memory.
13. The method of paragraph 10, wherein the patient has Alzheimer's disease and the decrease in the one or more symptoms are evaluated according to the DSM-5.
14. The method of paragraph 10, wherein the patient has Alzheimer's disease, and the decrease of symptoms is determined using the cognitive subscale of the Alzheimer's Disease Assessment Scale (ADAS-cog).
15. The method of paragraph 10, wherein the patient has Alzheimer's disease, and the decrease of symptoms is determined using the Clinician's Interview-Based Impression of Change (CIBIC-plus).
16. The method of paragraph 10, wherein the patient has Alzheimer's disease, and the decrease of symptoms is determined using the Activities of Daily Living Scale (ADL).
17. The method of any one of paragraphs 11-16, wherein any change in the underlying pathology is identified by detection of a biomarker before and after the L1 EN inhibitor administration.
18. The method of paragraph 17, wherein the biomarker is β-amyloid or Tau protein.
19. The method of paragraph 17 or 18, wherein the biomarker is detected by PET imaging.
20. The method of paragraph 17 or 18, wherein the biomarker is detected by measurement in the cerebrospinal fluid.
21. The method of any one of paragraphs 1-20, further comprising administering at least one second therapeutic agent to the patient.
22. The method of paragraph 21, wherein the patient has Alzheimer's disease and the at least one second therapeutic agent is useful for the treatment of the symptoms of Alzheimer's disease.
23. The method of paragraph 21, wherein the at least one second therapeutic agent is donepezil, galantamine, rivastigmine, or memantine.
24. The method of paragraph 21, wherein the at least one second therapeutic agent is an antibody that binds to β-amyloid or Tau protein.
25. The method of paragraph 24, wherein the antibody is binds to β-amyloid and is bapineuzumab.
26. The method of paragraph 24, wherein the antibody binds to Tau protein and is ABBV-8E12.
27. The method of paragraph 21, wherein the at least one second therapeutic agent is a vaccine against β-amyloid or Tau protein.
28. The method of paragraph 21, wherein the at least one second therapeutic agent is an agent that reduces or alters the brain content of β-amyloid or Tau.
29. The method of paragraph 28, wherein the second therapeutic agent reduces or alters the brain content of β-amyloid and is a β-secretase 1 (BACE) inhibitor.
30. The method of paragraph 29, wherein the BACE inhibitor is CTS-21166, verubecestat (MK-8931), lanabecestat (AZD3293) or LY2886721.
31. The method of paragraph 21, wherein the second agent reduces or alters the brain content of Tau and is nicotinamide, or MPT0G211.
32. The method of paragraph 20, wherein the patient has ALS and the at least one second therapeutic agent is useful for the treatment of ALS.
33. The method of paragraph 32, wherein the drug useful for the treatment of ALS is edaravone or riluzole.
34. The method of paragraph 32, wherein the at least one second agent is an integrase inhibitor.
35. The method of paragraph 34, wherein the integrase inhibitor is raltegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-25 870810, MK-0518, BMS-538158, or GSK364735C.
36. The method of any one of paragraphs 1-33, wherein the patient is evaluated for one or more symptoms or disease pathology 1-36 months after the first administration to the patient of the L1 EN inhibitor.
37. The method of any one of paragraphs 1-36, wherein the L1 EN inhibitor is selected from the group consisting of AD22, AD23, AD28, AD29, AD32, AD34, AD36, AD37, AD38, AD39, AD40, AD41, AD42, AD43, AD44, AD45, AD46, AD47, AD48, AD49, AD50, AD51, AD52, AD53, AD54, and AD55.
38. The method of any one of paragraphs 1-36, wherein the L1 EN inhibitor is selected from the group consisting of: AD22, AD23, AD28, AD29, AD32, AD34, and AD36.
39. The method of any one of paragraphs 1-36, wherein the L1 EN inhibitor is selected from the group consisting of: AD37, AD38, AD39, AD40, AD41, AD42, AD43, AD44, AD45, AD46, AD47, AD48, AD49, AD50, AD51, AD52, AD53, AD54, and AD55.

EXAMPLES

The invention now being generally described, it will be more readily understood by reference to the following examples which are included merely for purposes of illustration of certain aspects and embodiments of the present invention and are not intended to limit the invention.

Example 1 Novel L1 EN Inhibitors

As described above, recent evidence from our laboratory has shown that inhibition of the L1 RT domain by nucleoside reverse transcriptase inhibitors (NRTIs) originally designed against the HIV RT reduces the SASP in senescent cells in culture and in aging tissues. However, design of selective inhibitors for the L1 RT domain is currently not feasible due to the absence of structural information or knowledge about protein domain boundaries to enable recombinant protein purification. On the other hand, the structure of the L1 EN domain has been solved, allowing for structure-based inhibitor screening and design. The L1 EN is required for retrotransposition like the L1 RT, as L1 EN active site point mutations reduce retrotransposition similarly to those in the L1 RT. The L1 EN initiates L1 retrotransposition by nicking genomic DNA, which also results in double-strand breaks (DSBs) that can occur independent of L1 RT activity; it is estimated that the L1 EN can create 10-fold more DSBs than productive retrotransposition events. Additionally, inhibitors of the structurally homologous abasic site DNA repair endonuclease APE-1 have been characterized and provided initial candidate compounds.

Based on these APE-1 compounds, we developed inhibitors of the L1 EN that have shown efficacy in a biochemical assay and retrotransposition assay in cells. The inhibitors developed herein are the first inhibitors of the L1 EN domain to be discovered and the first of any retrotransposon-encoded endonuclease.

Methods

Biochemical Assay

The biochemical assay was based on Feng et al. (1996)[xxxvii] and Repanas et al. (2007).[xxxviii] Untagged human L1 EN domain (1-239) was purified from E. coli using heparin, cation-exchange, and size exclusion chromatography as previously described by Weichenrieder et al. (2004).[xxxix] Substrate supercoiled plasmid for the biochemical assay, pUC57, containing the E. coli codon-optimized ORF0 sequence (GenScript), was prepared using a QIAPrep Spin Miniprep Kit (Qiagen). Compounds were obtained from the following sources: AD1 (National Cancer Institute), AD2 (Alinda), AD3 (ChemBridge), AD4 (AK Scientific), AD5 (ChemDiv), AD6 (ChemBridge), AD7 (Enamine), AD8 (Sigma), AD9 (ChemDiv), AD10 (ChemBridge), AD11 (ChemDiv), AD12 (Sigma), AD13 (Specs), AD14 (Specs), AD15 (TargetMol), AD16 (Vitas), AD17 (Vitas), AD18 (UkrOrgSynthesis), AD19 (TimTec), AD20 (Vitas). All compounds were stored in DMSO at −20° C. as between 10 mM and 250 mM stocks depending on solubility.

Briefly, samples containing 20 nM purified L1 EN and compounds at the concentrations indicated above were incubated at room temperature for 60 minutes prior to adding 2 nM of plasmid. The reaction buffer was as follows: 20 mM HEPES pH 7.5, 100 mM NaCl, 10 mM $MgCl_2$, 0.1 mg/mL bovine serum albumin, and 4 mM DTT. Samples were incubated at 37° C. for 30 minutes before the reactions were stopped by heat inactivation at 70° C. for 10 minutes or addition of 50 mM EDTA. Samples were then run on a 1% agarose gel containing ethidium bromide in 1×TAE buffer for 90 minutes at 120V and the products visualized with a UV imager. Slower migration of plasmid relative to uncut substrate indicated L1 EN nicking activity. Linear plasmid resulted from multiple nicks near each other on opposite strands.

Cellular Assay

For the L1 retrotransposition reporter cellular assay, retrotransposition was measured by expression of a Firefly luciferase reporter after a retrotransposition event normalized to control Renilla luciferase expression. L1 was expressed from the doxycyclineinducible, dual luciferase-encoding plasmid pPM404 containing the human L1 sequence maintained episomally in HeLa-M2 cells. Hela cells were cultured at 37° C. in a humidified 5% $CO_2$ incubator in Dulbecco's Modified Eagle's Medium (DMEM)-high glucose with 10% heat inactivated fetal bovine serum and 1 μg/mL puromycin to maintain pPM404.

The HeLa-M2 cell line and the retrotransposition cellular assay were previously described in Mita et al. (2020).[xl] Briefly, cells were plated in a 96-well plate at a density of 15,000 cells per well. L1 expression was induced with 1 μg/mL of doxycycline and the compounds added at the concentrations indicated above. The final concentration of DMSO in each well was 0.1%. Each concentration was tested in quadruplicate in each independent assay. Cells were cultured for 2 days before luciferase reporter activity was quantified using the Dual-Luciferase® Reporter Assay System (Promega). The Cytation 5 Plate Reader (BioTek) was used to measure Firefly and Renilla signals. L1 activity was calculated as Firefly luciferase/Renilla luciferase*100. Independent assays used to calculate retrotransposition efficiencies in Table 2 are shown as separate graphs. The most effective compounds were also tested at multiple concentrations to show concentration-dependent inhibition. Statistical significance relative to no compound control was determined using an unpaired two-tailed t-test.

Development of Novel L1 EN Inhibitors

In a preliminary study, we demonstrated that one of the weaker APE-1 inhibitors,[ix] AD2 (ZINC ID: ZINC89469886, NCI: NSC89640, Ki=13 μM for APE-1), was effective against the L1 EN in the biochemical activity assay. In contrast, the most effective APE-1 inhibitor from the same screen, AD1 (ZINC ID: ZINC31769281, NCI: NSC332395, Ki=0.12 μM for APE-1), did not inhibit the L1 EN. These results demonstrate that, despite some overlap, compounds inhibit the L1 EN and APE-1 differently. This observation, combined with differences in the endonucleases' respective DNA binding pockets, indicated that development of compounds specific to the L1 EN was feasible.

We then screened analogs of AD2 that contained similar functional groups using an in silico molecular docking approach and tested top scoring compounds in the biochemical assay. We found that AD5 (ZINC ID: ZINC 100499350) inhibits activity completely at a 20-fold lower concentration than AD2. Several more AD2 analogs were identified (AD3, AD4, AD6, AD7, AD8, AD9, AD10, and AD11), including many with improved efficacy in the biochemical assay (see Table 2). Indeed, most of the analogs more effective than AD2 in the biochemical assay also reduced retrotransposition in the cellular reporter assay.

A similar molecular docking approach was then used to screen compound libraries filtered for structural similarity to the most effective AD2 analogs and libraries that are not filtered in order to obtain compounds with different functional groups. From a filtered library, AD14 was identified and determined to have efficacy in both assays. From an unfiltered library, we also identified AD12 (ZINC ID: ZINC1482077, Gliquidone) and AD15 (ZINC ID: ZINC537791, Glimepiride), sulfonylurea compounds used to treat diabetes mellitus type 2, and both inhibited L1 EN activity in the biochemical assay and reduced retrotransposition in the cellular reporter assay. Screening of unfiltered libraries also identified AD16, AD18, AD19, and AD20, which are structurally distinct from AD2, as well as AD13 and AD17, which have structural similarity to AD2. These compounds were effective in the biochemical assay, and some demonstrated efficacy in the retrotransposition assay.

A summary of results from each identified L1 EN inhibitor can be found in Table 2 and data for each inhibitor can be found in FIG. 2A to FIG. 2S and FIG. 3A to FIG. 3P.

TABLE 2

BIOCHEMICAL AND CELLULAR DATA FOR L1 EN INHIBITORS

Figure 2A:
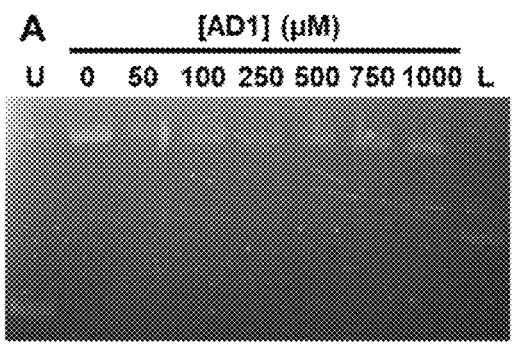
FIGS. 2A-2S show the results of the biochemical plasmid nicking L1 EN activity assay[vii] of the APE-1 inhibitor AD1 (FIG. 2A) and L1 EN inhibitors AD2-AD20 (FIGS. 2B-2S, respectively). Supercoiled plasmid was incubated with purified L1 EN[viii] inhibitors, and the reaction products visualized on an agarose gel. L1 EN nicking activity causes slower migration of plasmid. L, linearized plasmid; U, uncut plasmid.
Figure 2B:
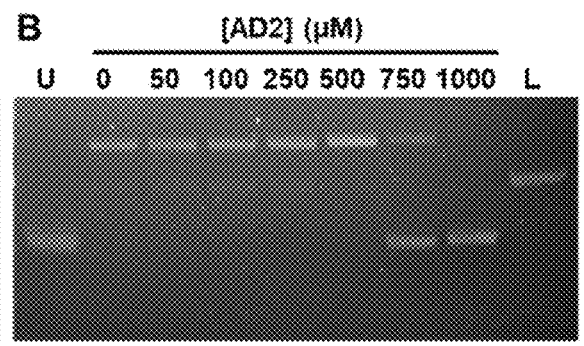
Figure 2C:
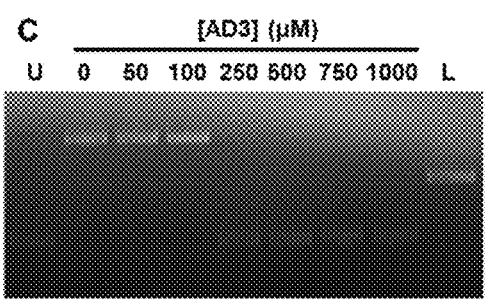
Figure 2D:
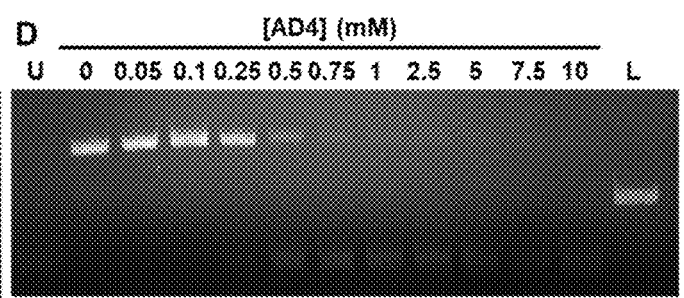
Figure 2E:
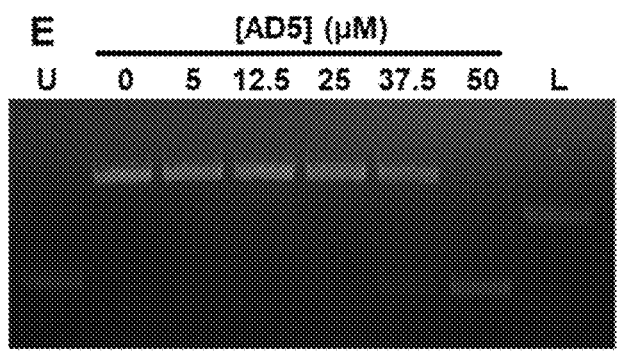

| Inhibitor ID, ZINC ID, and structure* | Biochemical assay: concentration at maximum inhibition | Cellular assay: retrotransposition efficiency (mean ± SD) |
|---|---|---|
| AD1 (ZINC31769281) 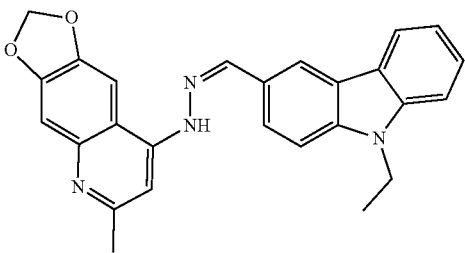 [SMILES: CCn1c2ccccc2c2cc(/C=N\Nc3cc(C)nc4cc5c(cc34)OCO5)ccc21] | No inhibition FIG. 2A | N.D.** |
| AD2 (ZINC89469886) 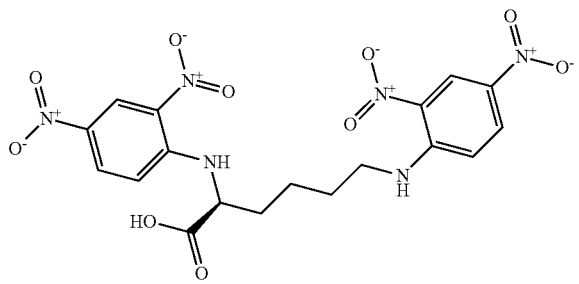 [SMILES: O=C(O)[C@H](CCCCNc1ccc([N+](=O)[O-])cc1[N+](=O)[O-])Nc1ccc([N+](=O)[O-])cc1[N+](=O)[O-]] | 100% inhibition at 1 mM FIG. 2B | 50 µM: 102.9 ± 27.4 FIG. 3A |
| AD3 (ZINC100299612) 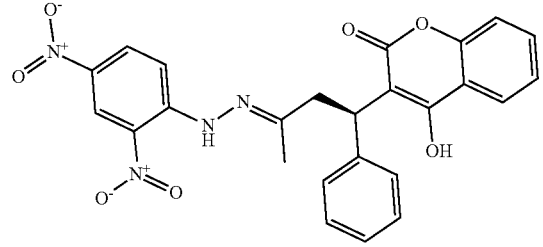 [SMILES: C/C(C[C@H](c1ccccc1)c1c(O)c2ccccc2oc1=O)=N\Nc1ccc([N+](=O)[O-])cc1[N+](=O)[O-]] | 100% inhibition at 250 µM FIG. 2C | 50 µM: 10.2 ± 10.8 FIG. 3B |
| AD4 (ZINC25558200) 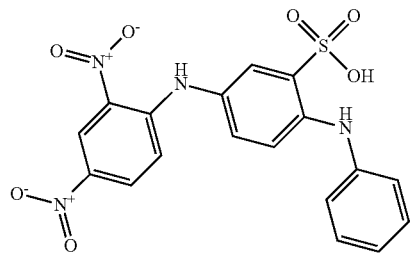 [SMILES: O=[N+]([O-])c1ccc(Nc2ccc(Nc3ccccc3)c(S(=O)(=O)O)c2)c([N+](=O)[O-])c1] | 100% inhibition at 1 mM FIG. 2D | N.D. |
| AD5 (ZINC100499350) 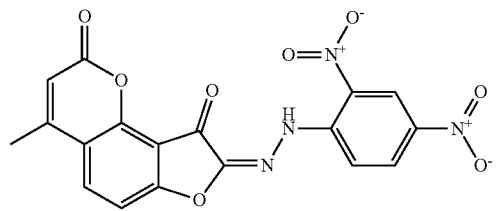 [SMILES: Cc1cc(=O)oc2c3c(ccc12)O/C(=N/Nc1ccc([N+](=O)[O-])cc1[N+](=O)[O-])C3=O] | 100% inhibition at 50 µM FIG. 2E | N.D. (poor solubility) |

TABLE 2-continued

BIOCHEMICAL AND CELLULAR DATA FOR L1 EN INHIBITORS

Figure 2F:
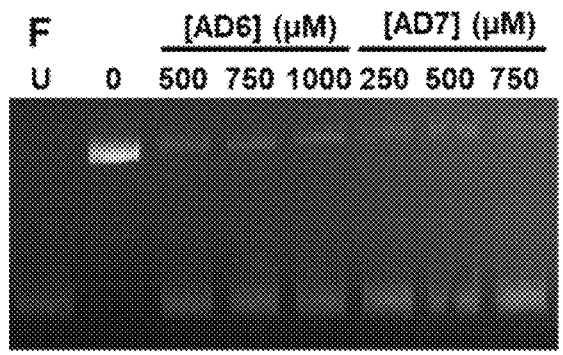
Figure 2G:
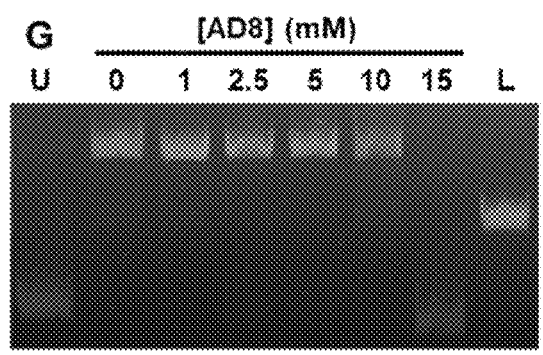
Figure 2H:
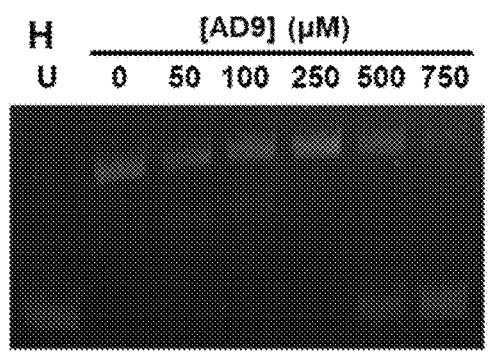
Figure 2I:
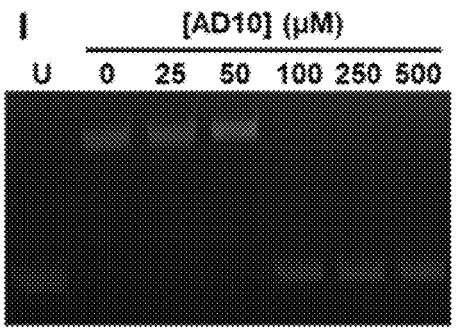
Figure 3D:
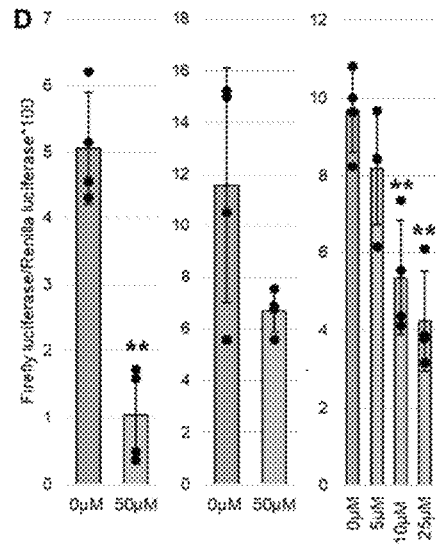
FIGS. 3A-3P show the results of the L1 retrotransposition reporter cellular assay of L1 EN inhibitors. Retrotransposition was measured by expression of a Firefly luciferase reporter after a retrotransposition event normalized to control Renilla luciferase expression. L1 was expressed from the doxycycline-inducible, dual luciferase-encoding plasmid pPM404 containing the human L1 sequence maintained episomally in HeLa-M2 cells.
Figure 3E:
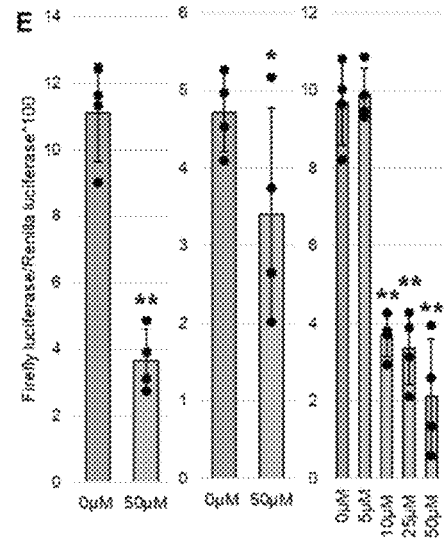
Figure 3F:
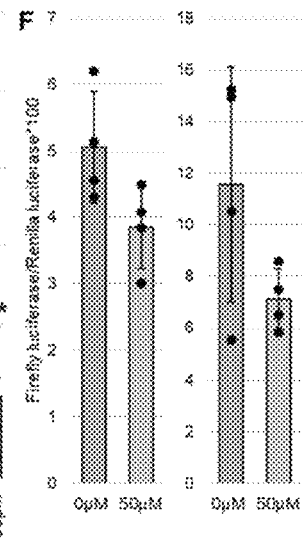

| Inhibitor ID, ZINC ID, and structure* | Biochemical assay: concentration at maximum inhibition | Cellular assay: retrotransposition efficiency (mean ± SD) |
|---|---|---|
| AD6 (ZINC4550549) 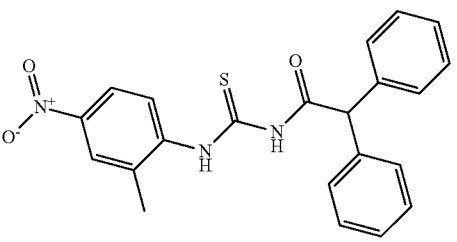 [SMILES: Cc1cc([N+](=O)[O-])ccc1NC(=S)NC(=O)C(c1ccccc1)c1ccccc1] | 90% inhibition at 750 μM FIG. 2F | 10 μM: 79.1 ± 25.5 FIG. 3C |
| AD7 (ZINC254379081) 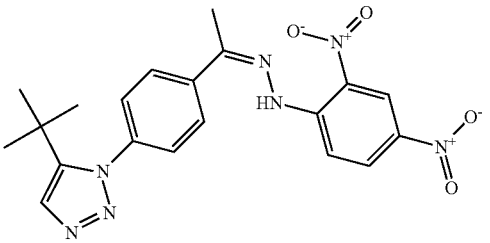 [SMILES: C/C(=N/Nc1ccc([N+](=O)[O-])cc1[N+](=O)[O-])c1ccc(-n2nncc2C(C)(C)C)cc1] | 80% inhibition at 500 μM FIG. 2F | 50 μM: 39.2 ± 22.5 FIG. 3D |
| AD8 (ZINC4517567) 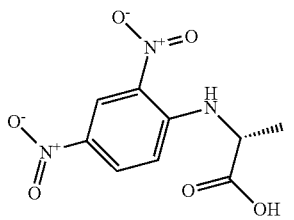 [SMILES: C[C@@H](Nc1ccc([N+](=O)[O-])cc1[N+](=O)[O-])C(=O)O] | 100% inhibition at 15 mM FIG. 2G | N.D. |
| AD9 (ZINC20677610) 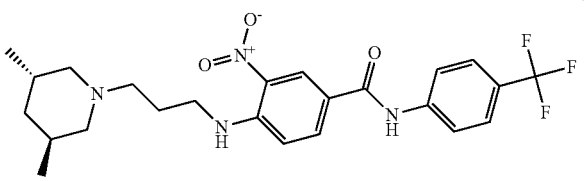 [SMILES: C[C@H]1C[C@H](C)CN(CCCNc2ccc(C(=O)Nc3ccc(C(F)(F)F)cc3)cc2[N+](=O)[O-])C1] | 80% inhibition at 750 μM FIG. 2H | 50 μM: 42.3 ± 28.7 FIG. 3E |
| AD10 (ZINC1218780) 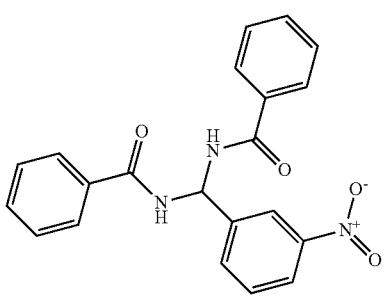 [SMILES: O=C(NC(NC(=O)c1ccccc1)c1cccc([N+](=O)[O-])c1)c1ccccc1] | 100% inhibition at 100 μM FIG. 2I | 50 μM: 68.9 ± 13.2 FIG. 3F |

TABLE 2-continued

BIOCHEMICAL AND CELLULAR DATA FOR L1 EN INHIBITORS

Figure 2J:
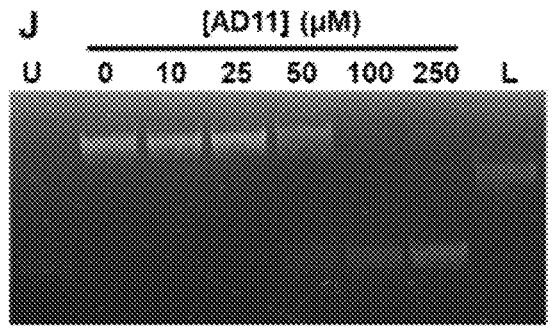
Figure 2K:
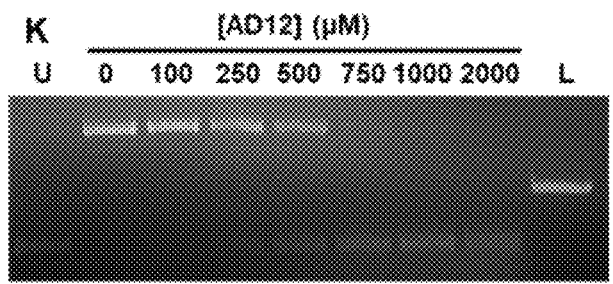
Figure 2L:
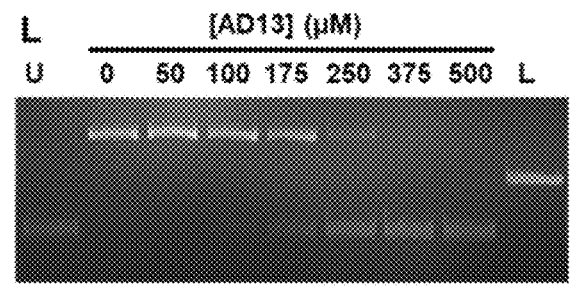
Figure 2M:
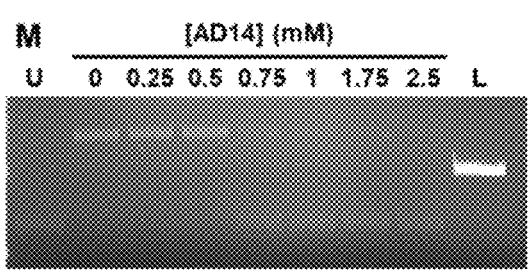
Figure 2N:
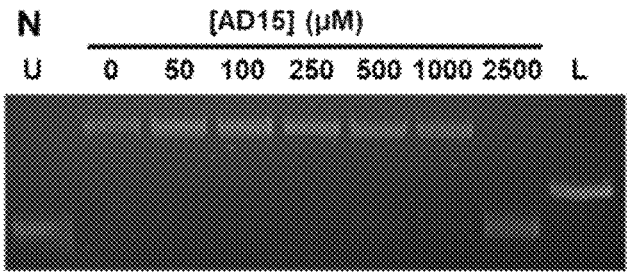
Figure 3G:
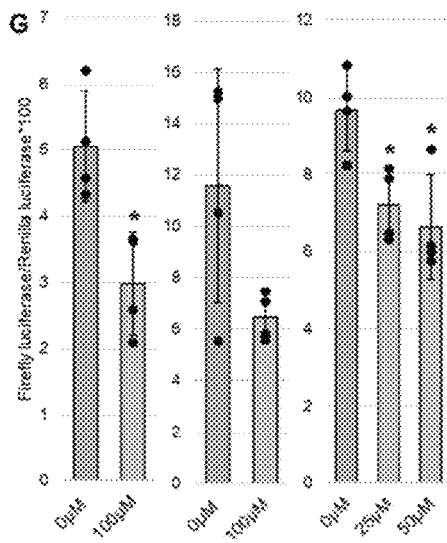
Figure 3H:
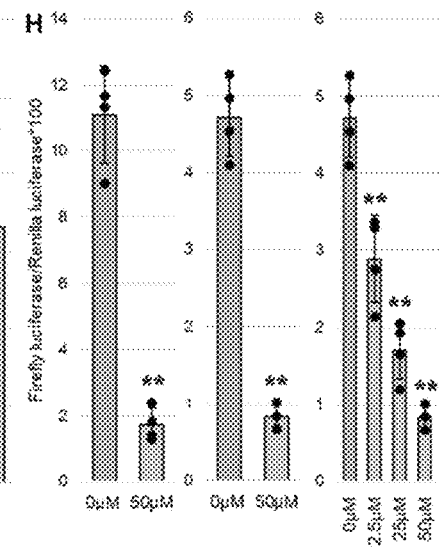
Figure 3I:
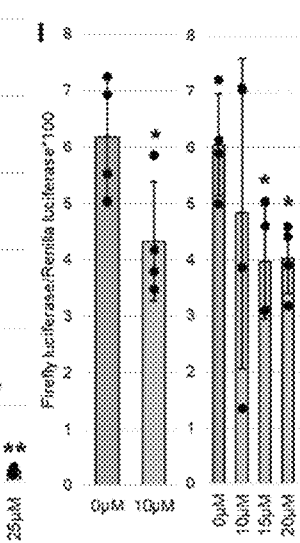

| Inhibitor ID, ZINC ID, and structure* | Biochemical assay: concentration at maximum inhibition | Cellular assay: retrotransposition efficiency (mean ± SD) |
|---|---|---|
| AD11 (ZINC12428901) | 100% inhibition at 10.0 μM FIG. 2J | 100 μM: 57.5 ± 11.4 FIG. 3G |
| AD12 (ZINC1482077) | 100% inhibition at 750 μM FIG. 2K | 50 μM: 17.7 ± 4.2 FIG. 3H |
| AD13 (ZINC8398444) | 100% inhibition at 500 μM FIG. 2L | 10 μM: 74.8 ± 32.4 FIG. 3I |
| AD14 (ZINC5758200) | 90% inhibition at 750 μM FIG. 2M | 10 μM: 73.4 ± 12.1 FIG. 3J |
| AD15 (ZINC537791) | 100% inhibition at 2.5 mM FIG. 2N | 50 μM: 17.1 ± 4.2 FIG. 3K |

Figure 2O:
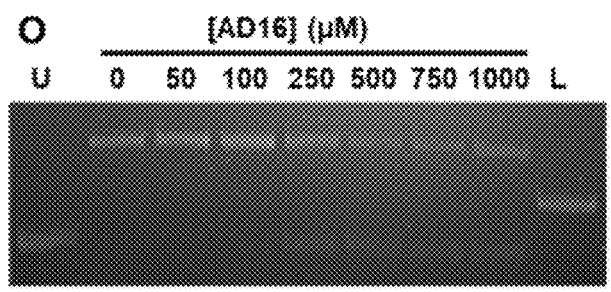
Figure 2P:
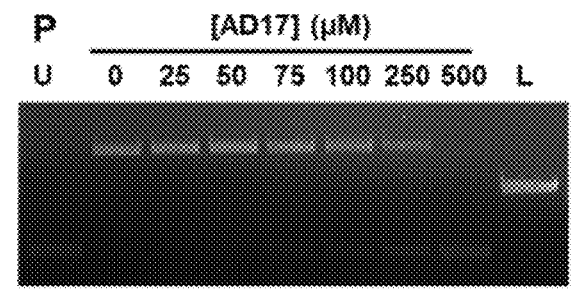

TABLE 2-continued
BIOCHEMICAL AND CELLULAR DATA FOR L1 EN INHIBITORS
| Inhibitor ID, ZINC ID, and structure* | Biochemical assay: concentration at maximum inhibition | Cellular assay: retrotransposition efficiency (mean ± SD) |
|---|---|---|
| AD16 (ZINC33355084) 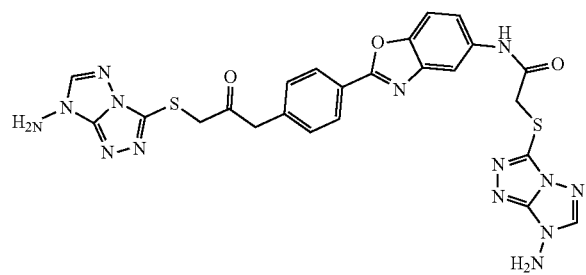 [SMILES: Nn1cnn2c(SCC(=O)Cc3ccc(-c4nc5cc(NC(=O)CSc6nnc7n(N)cnn67)ccc5o4)cc3)nnc12] | 50% inhibition at 500 μM FIG. 2O | 50 μM: 45.8 ± 24.9 FIG. 3L |
| AD17 (ZINC101372673) 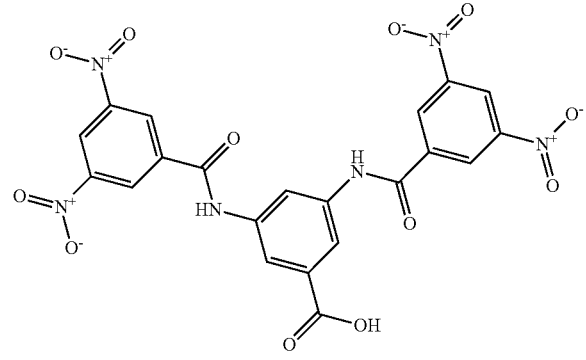 [SMILES: O=C(O)c1cc(NC(=O)c2cc([N+](=O)[O-])cc([N+](=O)[O-])c2)cc(NC(=O)c2cc([N+](=O)[O-])cc([N+](=O)[O-])c2)c1] | 100% inhibition at 500 μM FIG. 2P | 5 μM: 79.9 ± 8.6 FIG. 3M |
| AD18 (ZINC9602289) 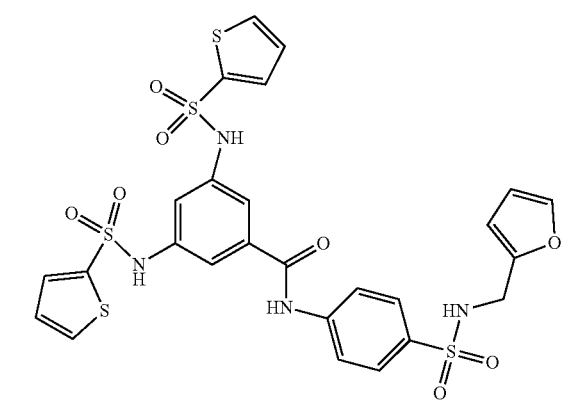 [SMILES: O=C(Nc1ccc(S(=O)(=O)NCc2ccco2)cc1)c1cc(NS(=O)(=O)c2cccs2)cc(NS(=O)(=O)c2cccs2)c1] | 50% inhibition at 750 μM FIG. 2Q | 10 μM: 73.6 ± 14.3 FIG. 3N |

TABLE 2-continued

BIOCHEMICAL AND CELLULAR DATA FOR L1 EN INHIBITORS

| Inhibitor ID, ZINC ID, and structure* | Biochemical assay: concentration at maximum inhibition | Cellular assay: retrotransposition efficiency (mean ± SD) |
|---|---|---|
| AD19 (ZINC150344228) 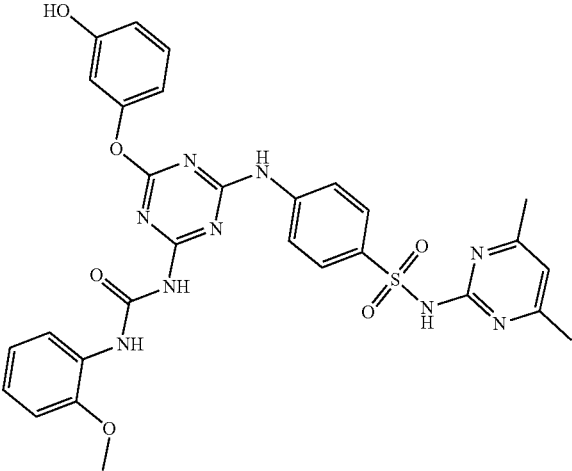 [SMILES: COc1ccccc1NC(=O)Nc1nc(Nc2ccc(S(=O)(=O)Nc3nc(C)cc(C)n3)cc2)nc(Oc2cccc(O)c2)n1] | 75% inhibition at 250 μM FIG. 2R | 25 μM: 92.5 ± 9.5 FIG. 3O |
| AD20 (ZINC8398012) 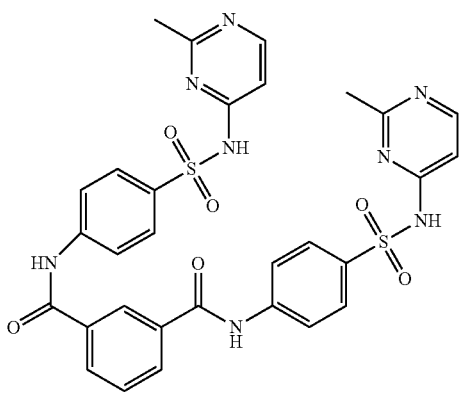 [SMILES: Cc1nccc(NS(=O)(=O)c2ccc(NC(=O)c3cccc(C(=O)Nc4ccc(S(=O)(=O)Nc5ccnc(C)n5)cc4)c3)cc2)n1] | 100% inhibition at 750 μM FIG. 2S | 50 μM: 102.5 ± 29.0 FIG. 3P |

*Images of compounds from ZINC database.
**N.D.: no data.

Having successfully identified numerous L1 EN inhibitors and having showed that these have efficacy in a biochemical assay and a retrotransposition assay in cells, the L1 endonuclease appears to be an advantageous target to inhibit L1 activity in the context of aging.

Example 2 Expanding Upon Characterizations of L1 EN Inhibitors

We have continued to characterize small molecule inhibitors of the LINE-1 (L1) endonuclease domain. We have found new inhibitors with efficacy in vitro and in cells using pharmacophore filtering and molecular docking in combination. We have also developed two new assays to quantify the impact of both existing and new L1 EN inhibitors on L1 activity.

Previously, we had used a plasmid-based nicking assay to screen candidate compounds and reported the inhibitor concentration at which there was maximum inhibition of L1 EN activity. However, we have now developed an improved biochemical assay for better quantification of inhibition and comparison among various inhibitors. This assay uses as the substrate a 43-nucleotide hairpin sequence containing a 5' fluorophore (6-FAM, fluorescein) and 3' quencher (BHQ-1, DABCYL quencher) such that prior to nicking fluorescent signal is minimal (FIG. 4A). The 43-nucleotide hairpin sequence containing a 5' fluorophore (6-FAM, fluorescein, F) and 3' quencher (BHQ-1, DABCYL quencher, Q) is described as F-(SEQ ID NO: 1)-Q, F-CGACTTTTAGAT-TGACACGCCATGCTGATCAATCTAAAAGTCG-Q, (FIG. 4A). L1 EN nicking results in fluorescence, allowing for real-time monitoring of activity in 96-well plates and quantification of inhibitor effects by calculating $IC_{50}$ values from a range of inhibitor concentrations. Using this assay, we have been able to show varying degrees of efficacy from inhibitors with different structural scaffolds (Table 3, FIG.

4B-FIG. 4U). In Table 3, IC$_{50}$ values were calculated from the fluorescent oligonucleotide EN nicking assay for previously described L1 EN inhibitors (AD2-19, FIG. 4A-FIG. 4N), as well as new inhibitors (AD22-AD36, FIG. 4O-FIG. 4U). Compounds AD41, AD43, and AD50 recently underwent testing (Table 3). Additional updated retrotransposition assay efficacies are provided for all inhibitors (Table 3, right column). IC$_{50}$ values were calculated from 3 independent experiments of the fluorescent oligonucleotide nicking assay with 3 replicates each and are mean±standard deviation. Retrotransposition efficiencies were calculated relative to no inhibitor control and are mean±standard deviation. Retrotransposition assay results are from at least 3 independent experiments with 4 replicates each.

TABLE 3

SUMMARY OF L1 EN INHIBITOR STRUCTURES AND EFFICACIES IN VITRO AND IN CELLS.

| Inhibitor ID, ZINC ID, and structure* | Biochemical assay: fluorescent oligonucleotide nicking assay IC$_{50}$ (µM) | Cellular assay: retrotransposition efficiency (%) |
|---|---|---|
| AD2 (ZINC89469886) | 102.9 ± 9.6 | 50 µM: 98.0 ± 22.9 |
| AD3 (ZINC100299612) | 114.2 ± 19.7 | 20 µM: 59.0 ± 22.4 |
| AD5 (ZINC100499350) | 16.8 ± 6.3 | 10 µM: 89.7 ± 14.0 |
| AD7 (ZINC254379081) | 875.1 ± 247.4 | 20 µM: 42.2 ± 23.9 |

TABLE 3-continued
SUMMARY OF L1 EN INHIBITOR STRUCTURES AND EFFICACIES IN VITRO AND IN CELLS.
| Inhibitor ID, ZINC ID, and structure* | Biochemical assay: fluorescent oligonucleotide nicking assay IC$_{50}$ (µM) | Cellular assay: retrotransposition efficiency (%) |
|---|---|---|
| AD9 (ZINC20677610) | 670.9 ± 142.5 | 50 µM: 21.9 ± 10.9 |
| AD11 (ZINC12428901) | 3.8 ± 1.4 | 50 µM: 52.2 ± 14.4 |
| AD12 (ZINC1482077) | 690.9 ± 142.5 | 50 µM: 17.7 ± 1.9 |
| AD13 (ZINC8398444) | 33.3 ± 16.2 | 20 µM: 75.4 ± 30.7 |
| AD14 (ZINC5758200) | 5.9 ± 1.7 | 25 µM: 71.6 ± 10.4 |
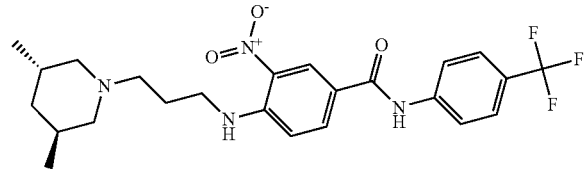 [SMILES: C[C@H]1C[C@H](C)CN(CCCNc2ccc(C(=O)Nc3ccc(C(F)(F)F)cc3)cc2[N+](=O)[O-])C1]
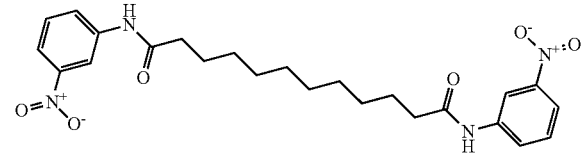 [SMILES: O=C(CCCCCCCCCCC(=O)Nc1cccc([N+](=O)[O-])c1)Nc1cccc([N+](=O)[O-])c1]
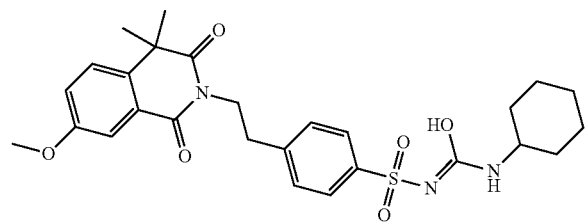 [SMILES: COc1ccc2c(c1)C(=O)N(CCc1ccc(S(=O)(=O)/N=C(\O)NC3CCCCC3)cc1)C(=O)C2(C)C]
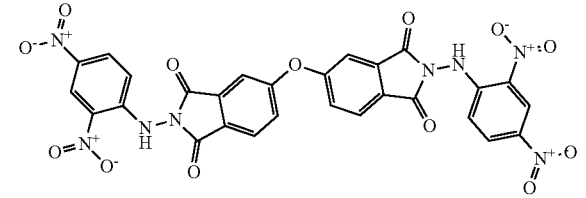 [SMILES: O=C1c2ccc(Oc3ccc4c(c3)C(=O)N(Nc3ccc([N+](=O)[O-])cc3[N+](=O)[O-])C4=O)cc2C(=O)N1Nc1ccc([N+](=O)[O-])cc1[N+](=O)[O-]]
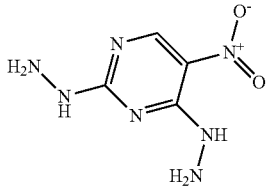 [SMILES: NNc1ncc([N+](=O)[O-])c(NN)n1]

TABLE 3-continued
SUMMARY OF L1 EN INHIBITOR STRUCTURES AND EFFICACIES IN VITRO AND IN CELLS.
| Inhibitor ID, ZINC ID, and structure* | Biochemical assay: fluorescent oligonucleotide nicking assay IC$_{50}$ (μM) | Cellular assay: retrotransposition efficiency (%) |
|---|---|---|
| AD16 (ZINC33355084) | 5.7 ± 0.9 | 25 μM: 59.2 ± 21.7 |
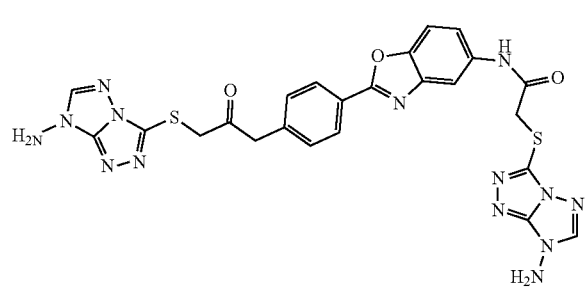 [SMILES: Nn1cnn2c(SCC(=O)Cc3ccc(-c4nc5cc(NC(=O)CSc6nnc7n(N)cnn67)ccc5o4)cc3)nnc12]
| | | |
|---|---|---|
| AD17 (ZINC101372673) | 47.1 ± 7.8 | 5 μM: 94.8 ± 15.8 |
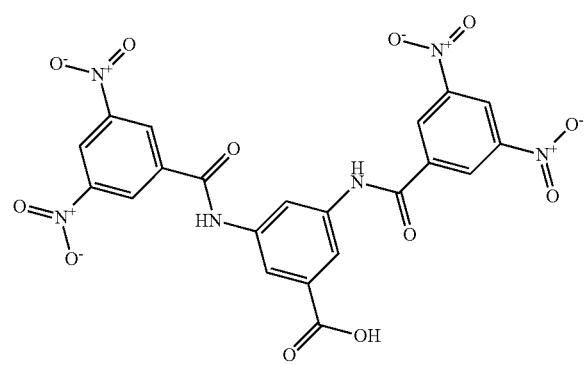 [SMILES: O=C(O)c1cc(NC(=O)c2cc([N+](=O)[O-])cc([N+](=O)[O-])c2)cc(NC(=O)c2cc([N+](=O)[O-])cc([N+](=O)[O-])c2)c1]
| | | |
|---|---|---|
| AD18 (ZINC9602289) | 75.8 ± 8.3 | 10 μM: 92.2 ± 16.4 |
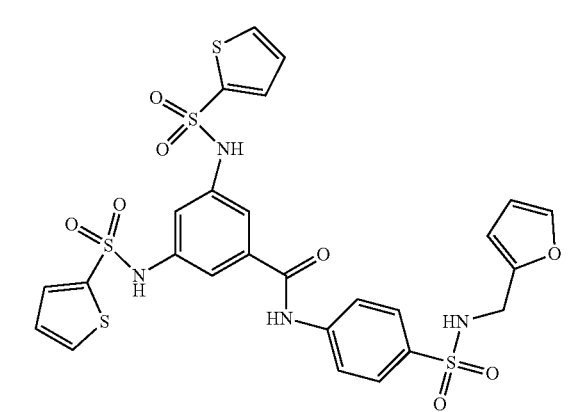 [SMILES: O=C(Nc1ccc(S(=O)(=O)NCc2ccco2)cc1)c1cc(NS(=O)(=O)c2cccs2)cc(NS(=O)(=O)c2cccs2)c1]

TABLE 3-continued
SUMMARY OF L1 EN INHIBITOR STRUCTURES AND EFFICACIES IN VITRO AND IN CELLS.
| Inhibitor ID, ZINC ID, and structure* | Biochemical assay: fluorescent oligonucleotide nicking assay $IC_{50}$ (μM) | Cellular assay: retrotransposition efficiency (%) |
| --- | --- | --- |
| AD19 (ZINC150344228) | 31.1 ± 14.1 | 25 μM: 95.2 ± 2.6 |
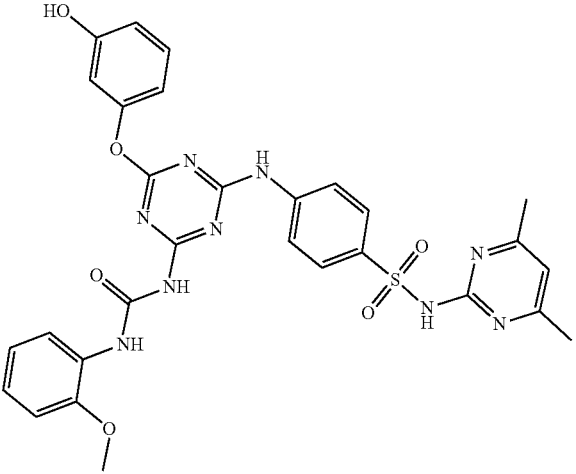 [SMILES: COc1ccccc1NC(=O)Nc1nc(Nc2ccc(S(=O)(=O)Nc3nc(C)cc(C)n3)cc2)nc(Oc2cccc(O)c2)n1]
| AD22 (ZINC5944441) | 1058.7 ± 192.0 | 50 μM: 63.3 ± 7.1 |
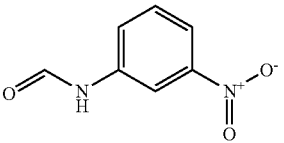 [SMILES: O=CNc1cccc([N+](=O)[O-])c1]
| AD23 (ZINC4086624) | 447.6 ± 163.2 | 40 μM: 113.9 ± 20.1 |
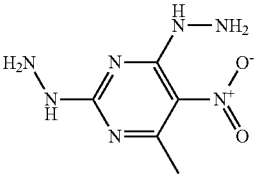
| AD28 (ZINC9116296) | 417.3 ± 34.4 | Toxicity at 2.5 μM |
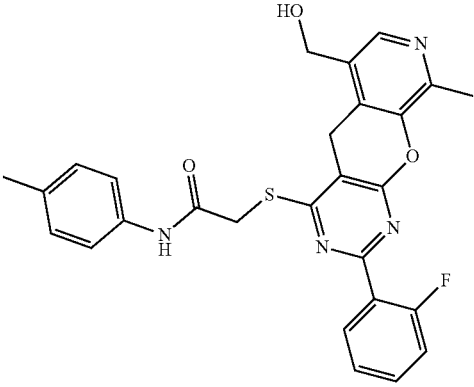

TABLE 3-continued
SUMMARY OF L1 EN INHIBITOR STRUCTURES AND EFFICACIES IN VITRO AND IN CELLS.
| Inhibitor ID, ZINC ID, and structure* | Biochemical assay: fluorescent oligonucleotide nicking assay IC$_{50}$ (µM) | Cellular assay: retrotransposition efficiency (%) |
|---|---|---|
| AD29 (ZINC33355295) | 29.1 ± 2.9 | 50 µM: 85.8 ± 7.9 |
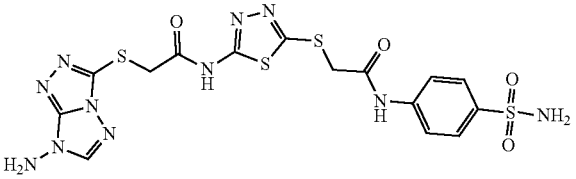 [SMILES: Nn1cnn2c(SCC(=O)Nc3nnc(SCC(=O)Nc4ccc(S(N)(=O)=O)cc4)s3)nnc12]
| | | |
|---|---|---|
| AD32 (ZINC9056988) | 460.9 ± 83.0 | 25 µM: 35.1 ± 16.5 |
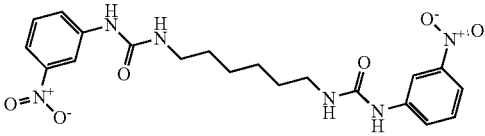 [SMILES: O=C(NCCCCCCNC(=O)Nc1cccc([N+](=O)[O-])c1)Nc1cccc([N+](=O)[O-])c1]
| | | |
|---|---|---|
| AD34 (ZINC33356589) | 13.6 ± 4.4 | 25 µM: 104.3 ± 7.8 |
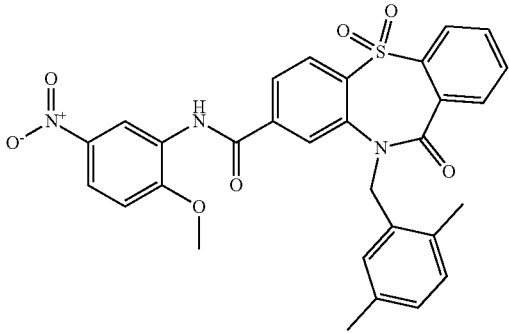 [SMILES: COc1ccc([N+](=O)[O-])cc1NC(=O)c1ccc2c(c1)N(Cc1cc(C)ccc1C)C(=O)c1ccccc1S2(=O)=O]
| | | |
|---|---|---|
| AD36 (ZINC16215374) | 928.3 ± 436.7 | 25 µM: 42.9 ± 22.2 |
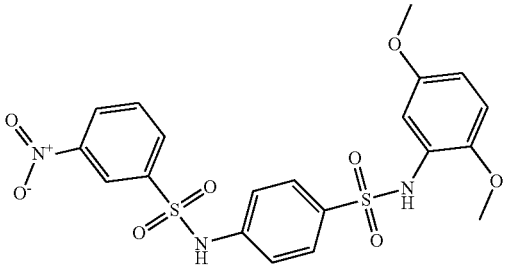 [SMILES: COc1ccc(OC)c(NS(=O)(=O)c2ccc(NS(=O)(=O)c3cccc([N+](=O)[O-])c3)cc2)c1]
| | | |
|---|---|---|
| AD37 (ZINC100007011) | N.D. | N.D. |
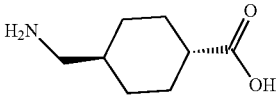

TABLE 3-continued
SUMMARY OF L1 EN INHIBITOR STRUCTURES AND EFFICACIES IN VITRO AND IN CELLS.
| Inhibitor ID, ZINC ID, and structure* | Biochemical assay: fluorescent oligonucleotide nicking assay IC$_{50}$ (μM) | Cellular assay: retrotransposition efficiency (%) |
|---|---|---|
| AD38 (ZINC154737) | N.D. | N.D. |
| AD39 (ZINC49550468) | N.D. | N.D. |
| AD40 (ZINC3883091) | N.D. | N.D. |
| AD41 (ZINC425300) | 458.8 ± 224.3 | 25 μM: 129.4 ± 12.0 |
| AD42 (ZINC238950702) | N.D. | N.D. |
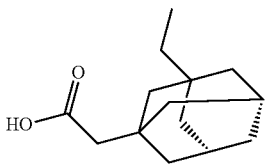 [SMILES: CCC12C[C@H]3C[C@@H](C1)CC(CC(=O)O)(C3)C2]
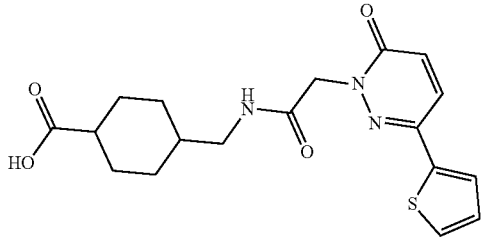 [SMILES: O=C(Cn1nc(-c2cccs2)ccc1=O)NCC1CCC(C(=O)O)CC1]
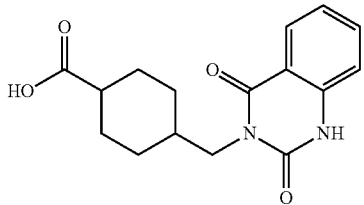 [SMILES: O=C(O)C1CCC(Cn2c(=O)[nH]c3ccccc3c2=O)CC1]
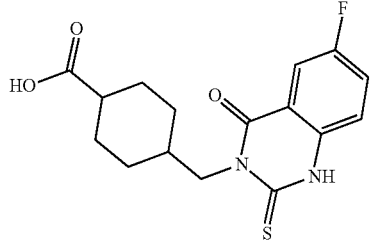 [SMILES: O=C(O)C1CCC(Cn2c(=S)[nH]c3ccc(F)cc3c2=O)CC1]
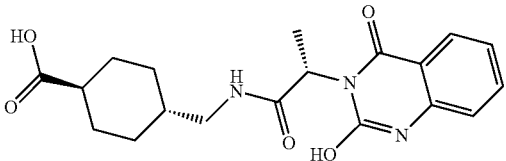 [SMILES: C[C@@H](C(=O)NC[C@H]1CC[C@H](C(=O)O)CC1)n1c(O)nc2ccccc2c1=O]

TABLE 3-continued
SUMMARY OF L1 EN INHIBITOR STRUCTURES AND EFFICACIES IN VITRO AND IN CELLS.
| Inhibitor ID, ZINC ID, and structure* | Biochemical assay: fluorescent oligonucleotide nicking assay IC$_{50}$ (μM) | Cellular assay: retrotransposition efficiency (%) |
|---|---|---|
| AD43 (ZINC238900190) | 703.9 ± 176.7 | 50 μM: 57.3 ± 9.0 |
| 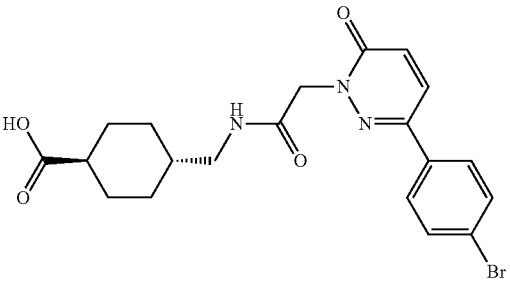 [SMILES: O=C(Cn1nc(-c2ccc(Br)cc2)ccc1=O)NC[C@H]1CC[C@H](C(=O)O)CC1] | | |
| AD44 (ZINC950756015) | N.D. | N.D. |
| 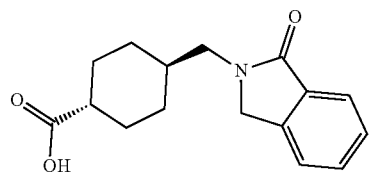 [SMILES: O=C1c2ccccc2CN1C[C@H]1CC[C@H](C(=O)O)CC1] | | |
| AD45 (ZINC952964257) | N.D. | N.D. |
| 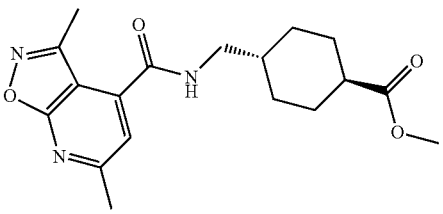 [SMILES: COC(=O)[C@H]1CC[C@H](CNC(=O)c2cc(C)nc3onc(C)c23)CC1] | | |
| AD46 (ZINC2029360) | N.D. | N.D. |
| 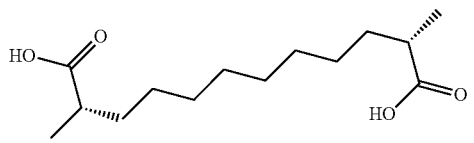 [SMILES: C[C@@H](CCCCCCCC[C@H](C)C(=O)O)C(=O)O] | | |
| AD47 (ZINC253387679) | N.D. | N.D. |
| 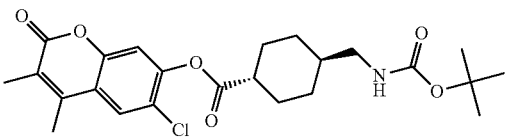 [SMILES: Cc1c(C)c2cc(Cl)c(OC(=O)[C@H]3CC[C@H](CNC(=O)OC(C)(C)C)CC3)cc2oc1=O] | | |
| AD48 (ZINC252695296) | N.D. | N.D. |
| 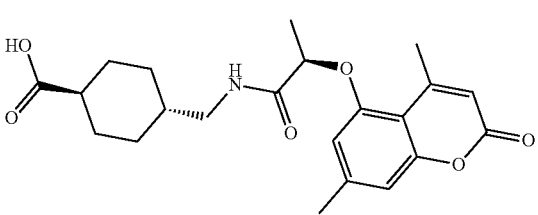 [SMILES: Cc1cc(O[C@H](C)C(=O)NC[C@H]2CC[C@H](C(=O)O)CC2)c2c(C)cc(=O)oc2c1] | | |

TABLE 3-continued

SUMMARY OF L1 EN INHIBITOR STRUCTURES AND EFFICACIES IN VITRO AND IN CELLS.

| Inhibitor ID, ZINC ID, and structure* | Biochemical assay: fluorescent oligonucleotide nicking assay IC$_{50}$ (μM) | Cellular assay: retrotransposition efficiency (%) |
|---|---|---|
| AD49 (ZINC4747299) | N.D. | N.D. |
| AD50 (ZINC238924061) | 291.6 ± 18.4 | 25 μM: 100.5 ± 15.0 |
| AD51 (ZINC2204671) | N.D. | N.D. |
| AD52 (ZINC242548640) | N.D. | N.D. |
| AD53 (ZINC242688517 | N.D. | N.D. |
| AD54 (ZINC252585388) | N.D. | N.D. |

TABLE 3-continued

SUMMARY OF L1 EN INHIBITOR STRUCTURES AND EFFICACIES IN VITRO AND IN CELLS.

| Inhibitor ID, ZINC ID, and structure* | Biochemical assay: fluorescent oligonucleotide nicking assay IC$_{50}$ (μM) | Cellular assay: retrotransposition efficiency (%) |
|---|---|---|
| AD55 (ZINC245204959)  | N.D. | N.D. |

*Images of compounds from ZINC database.
**N.D.: no data (not yet tested).

The nicking assay and retrotransposition assay are further described in FIGS. 4A-4U and FIGS. 5A-5F, respectively. FIG. 4A shows a schematic of the fluorescent oligonucleotide nicking assay. The schematic illustrates the hairpin oligonucleotide containing F-(SEQ ID NO: 1)-Q, F-CGACTTTTAGATTGACACGCCATGCTGAT-CAATCTAAAAGTCG-Q. At left is shown the sequence of the hairpin oligonucleotide containing 5' 6-FAM fluorescein fluorophore (F) and 3' DABCYL quencher (Q), adapted from Srinivasan, et al., 2012.[ix] The EN target sequence was added to the stem of the hairpin, the 5-FAM fluorescent tag was included at the 5' end, and the DABCYL quencher was included at the 3' end. The sequence representation is in F-(SEQ ID NO: 1)-Q, 5'-F-CGACTTTTAGAT-TGACACGCCATGTCGATCAATCTAAAAGTCG-Q-3'. Reactions were completed in buffer containing 20 mM HEPES pH 7.5, 50 mM NaCl, and 2.5 mM MgCl2. EN WT at 2.5 nM was incubated with inhibitors or vehicle for 1 hour before adding 25 nM oligo. Fluorescence was measured at regular intervals at 37° C. using a Synergy H1 plate reader (BioTek). Initial rates were normalized to no inhibitor control to calculate percent activity and IC$_{50}$ values were obtained using [inhibitor] vs. response non-linear fit in GraphPad Prism version 9.4.1 for Windows. No inhibitor control and full inhibition by 50 mM EDTA were included in fit calculations to guide definition of the top and bottom of the fit curve.

At middle of FIG. 4A, the arrowhead indicates location of nick by L1 EN at the semi-specific target site sequence, SEQ ID NO: 2, 5'-TTTT*A-3'. The melting temperature of the green sequence, SEQ ID NO: 3, F-CGACTTT, or F-(SEQ ID NO: 3), is lower than reaction temperature, whereas melting temperature of full hairpin is higher than the reaction temperature. At right, the nicked sequence is released away from the quencher, allowing for fluorescence to occur as a real-time readout for activity using a plate reader.

FIG. 4B to FIG. 4U show representative assay results for L1 EN inhibitors. Graphs show percent of no inhibitor control L1 EN activity as a function of indicated inhibitor concentration. Activity was determined as initial rate of reaction under multiple turnover conditions and normalized to no inhibitor control. IC$_{50}$ values were calculated using [inhibitor] vs. response non-linear fit in GraphPad Prism version 9.4.1 for Windows. No inhibitor control and full inhibition by 50 mM EDTA were included in fit calculations to guide definition of top and bottom of fit curve. FIG. 4B to FIG. 4U shows representative assay results for AD2, AD3, AD5, AD7, AD9, AD11, AD12, AD13, AD14, AD16, AD17, AD18, AD19, AD22, AD23, AD28, AD29, AD32, AD34, and AD36, respectively.

Additionally, we have continued to use the established L1 retrotransposition cell culture reporter assay to characterize the effects of both existing inhibitors AD2-AD19 (Table 3) and new inhibitors AD22-AD36 (Table 3, FIGS. 5A-5F) in cells. FIGS. 5A-5F shows the retrotransposition assay results for new inhibitors. Retrotransposition was measured in HeLa cells by expression of a luciferase reporter after a retrotransposition event. 3TC was included for comparison to L1 RT inhibition. During compound screening with this assay, PrestoBlue Viability Reagent was used to test cytotoxicity; compounds with statistically significant toxicity were subsequently tested at lower concentrations or excluded from further testing. Statistical significance relative to no inhibitor control (0 μM) determined using an unpaired two-tailed t-test. FIGS. 5A-5F panels: FIG. 5A) AD22, FIG. 5B) AD23, FIG. 5C) AD29, FIG. 5D) AD32, FIG. 5E) AD34, FIG. 5F) AD36. Error bars=S.D., *p≤0.05, **p≤0.01.

DNA Damage Cellular Assay

ORFeus expression constructs were introduced into HeLa Tet-On cells by transfection with FuGENE HD (Promega) for 24 hours followed by selection with 1 μg/mL puromycin. Cells were induced with 2 μg/mL doxycycline and treated with inhibitors or vehicle for 24 hours. Cells were then washed with PBS prior to fixation in 4% paraformaldehyde for 20 minutes. Samples were permeabilized and blocked before incubating with γ-H2AX monoclonal mouse antibody JBW301 (Millipore Sigma, 1:1000) for 2 hours. Samples were then treated with appropriate secondary antibodies diluted 1:200 for 2 hours followed by DAPI (1 μg/mL) for 20 minutes. Finally, coverslips were mounted onto slides with ProLong Gold Antifade Mountant (Invitrogen). Images were acquired with a Nikon Ti2-E Fluorescence Microscope.

Quantification of γ-H2AX was completed with CellProfiler. An existing pipeline was modified to identify nuclei, identify γ-H2AX signal, and measure the mean γ-H2AX intensity for each nucleus with γ-H2AX signal. All images for each independent experiment were acquired during the same imaging session and with the same exposure.

We also wanted to explore the effects of L1 EN inhibitors on L1-induced DNA damage in HeLa cells. Inactivation of L1 EN by active site point mutation has been previously shown to significantly reduce DNA damage when L1 is overexpressed, so we reasoned that pharmacological L1 EN inhibition would have a similar effect. We have demonstrated that several inhibitors reduce DNA damage relative to no inhibitor treatment (FIGS. 6A-6B). After induction of L1 expression and addition of inhibitors, DNA damage is detected using immunofluorescence for γ-H2AX, a marker of double-stranded DNA breaks. This staining is then quantified using an adapted pipeline from Cell Profiler that measures the average γ-H2AX signal for each nucleus identified. Our results show that the inhibitors reduce γ-H2AX signal both when the full-length L1 element (ORF1 and ORF2) is expressed (FIG. 6A), as well as when the L1 EN domain is expressed alone (FIG. 6B). Our results demonstrate that small molecule L1 EN inhibitors can reduce DNA damage promoted by the expression of L1 elements.

FIGS. 6A-6B shows the effects of L1 EN inhibitors on L1-induced DNA damage. HeLa Tet-On cell lines containing doxycycline-inducible full-length (FL, ORF1 and ORF2) or L1 EN domain only L1 expression constructs were generated for WT and mutant (EN-, H230A; RT-, D702Y) L1. FIG. 6A shows average of mean γ-H2AX intensities of individual nuclei (n=233-723) normalized to WT no inhibitor control for FL expression. FIG. 6B shows average of mean γ-H2AX intensities of individual nuclei (n=68-256) normalized to WT no inhibitor control for L1 EN domain expression. Results are from at least 2 independent experiments per sample. All samples from the same experiment were processed in parallel and images were acquired with the same exposure. Mean γ-H2AX intensity analysis was performed with CellProfiler. Statistical significance vs. WT was determined by one-way ANOVA followed by Dunnett's multiple comparisons test using GraphPad Prism version 9.4.1 for Windows. Error bars: ±S.E., *$p<0.05$, $p<0.01$, *$p<0.001$, ****$p<0.0001$. The DNA Damage Cellular Assay is further described below.

Biophysical Characterization of EN Inhibitors

After quantifying the effects on inhibitors on in vitro EN activity, we sought to measure direct interactions between the EN and inhibitors in the absence of DNA using spectral shift. In this method, fluorescently labeled EN is incubated with varying concentrations of inhibitor. Changes in the environment of the fluorophore, including nearby binding of a ligand or conformational changes in the protein, cause a shift in the emission spectrum. By calculating the ratio of fluorescence at two wavelengths as a function of inhibitor concentration, a binding curve can be generated and a dissociation constant (Kd) fit applied. Since this shift can either be a "red" shift or "blue" shift, the ratio value of the bound state may be higher or lower than the unbound state, resulting in a curve that may increase or decrease with higher inhibitor concentrations. Our results show binding that predominantly corresponds with $IC_{50}$ values, with higher efficacy inhibitors generally showing higher affinity $K_d$ values (FIGS. 7A-7R). As with the oligonucleotide assay, we have completed these measurements in triplicate and the results are summarized in Table 4. The $K_d$ values (Table 4) were calculated from at least 3 independent spectral shift experiments with 3 replicate measurements each and are mean±s.d. (in Table 4, N.D., binding not detected).

TABLE 4

INHIBITOR ID, ZINC ID, AND $K_D$ (µM)

| Inhibitor ID and ZINC ID | $K_d$ (µM) |
|---|---|
| AD2 (ZINC89469886) | 82.4 ± 34.4 |
| AD3 (ZINC100299612) | 10.4 ± 8.0 |
| AD5 (ZINC100499350) | 1.4 ± 0.2 |
| AD7 (ZINC254379081) | 223.0 ± 57.1 |
| AD9 (ZINC20677610) | 5.0 ± 2.2 |
| AD11 (ZINC12428901) | 12.7 ± 10.1 |
| AD12 (ZINC1482077) | 740.7 ± 393.6 |
| AD13 (ZINC8398444) | 21.5 ± 13.1 |
| AD14 (ZINC5758200) | 19.8 ± 8.5 |
| AD16 (ZINC33355084) | 8.8 ± 1.8 |
| AD17 (ZINC101372673) | 27.2 ± 19.9 |
| AD18 (ZINC9602289) | 11.6 ± 7.7 |
| AD28 (ZINC9116296) | 14.7 ± 3.7 |
| AD29 (ZINC33355295) | 139.7 ± 42.9 |
| AD32 (ZINC9056988) | N.D. |
| AD34 (ZINC33356589) | 1.8 ± 0.4 |
| AD36 (ZINC16215374) | 228.0 ± 18.5 |
| AD41 (ZINC425300) | N.D. |
| AD43 (ZINC238900190) | 516.3 ± 69.0 |
| AD50 (ZINC238924061) | 207.0 ± 43.3 |

EN Inhibitors Reduce L1 Retrotransposition in Cell Culture

After characterizing EN inhibitors biochemically and biophysically, we determined the effects of these inhibitors on L1 retrotransposition in cells. We first evaluated the inhibitors with regard to L1 retrotransposition, as this represents the most direct and well-characterized impact of L1 activity in cells. We used an established HeLa cell culture dual-luciferase reporter assay to measure L1 retrotransposition. In this assay, expression of a Firefly luciferase reporter occurs only after insertion of a new L1 element. We found that several compounds that inhibited EN activity in the in vitro assays reduced retrotransposition relative to the no inhibitor control (FIGS. 8A-8E). Significantly, we found at least one inhibitor from each round of docking with cellular activity. The RT inhibitor 3TC served as a comparison to inhibition of the RT domain. Several EN inhibitors decreased retrotransposition to a similar degree as 3TC, while for others the effect was less potent. We also monitored potential toxicity using the PrestoBlue assay followed by luciferase measurements, as these assays have been used in combination previously. For compounds with the best inhibition in this assay, we showed effects across multiple concentrations (FIGS. 8F-8M). A summary 200 of EN inhibitor retrotransposition efficiencies calculated as a percentage of the no inhibitor control across multiple independent experiments can be found in Table 5.

TABLE 5

SUMMARY OF EN INHIBITOR $IC_{50}$, $K_D$, AND RETROTRANSPOSITION VALUES.

| Inhibitor ID | $IC_{50}$ (µM) | $K_d$ (µM) | Inhibitor ID |
|---|---|---|---|
| AD2 | 102.9 ± 9.6 | 82.4 ± 34.4 | 50 µM: 98.0 ± 22.9 |
| AD3 | 114.2 ± 19.7 | 10.4 ± 8.0 | 20 µM: 59.0 ± 22.4 |
| AD5 | 16.8 ± 6.3 | 1.4 ± 0.2 | 10 µM: 89.7 ± 14.0 |
| AD7 | 875.1 ± 247.4 | 223.0 ± 57.1 | 20 µM: 42.2 ± 23.9 |
| AD9 | 670.9 ± 142.5 | 5.0 ± 2.2 | 50 µM: 21.9 ± 10.9 |
| AD11 | 3.8 ± 1.4 | 12.7 ± 10.1 | 50 µM: 52.2 ± 14.4 |
| AD12 | 690.9 ± 142.5 | 740.7 ± 393.6 | 50 µM: 17.7 ± 1.9 |
| AD13 | 33.3 ± 16.2 | 21.5 ± 13.1 | 20 µM: 75.4 ± 30.7 |
| AD14 | 5.9 ± 1.7 | 19.8 ± 8.5 | 25 µM: 71.6 ± 10.4 |
| AD16 | 5.7 ± 0.9 | 8.8 ± 1.8 | 25 µM: 59.2 ± 21.7 |
| AD17 | 47.1 ± 7.8 | 27.2 ± 19.9 | 5 µM: 94.8 ± 15.8 |
| AD18 | 75.8 ± 8.3 | 11.6 ± 7.7 | 10 µM: 92.2 ± 16.4 |
| AD28 | 417.3 ± 34.4 | 14.7 ± 3.7 | Toxicity at 2.5 µM |
| AD29 | 29.1 ± 2.9 | 139.7 ± 42.9 | 50 µM: 85.8 ± 7.9 |
| AD32 | 460.9 ± 83.0 | N.D. | 25 µM: 35.1 ± 16.5 |

TABLE 5-continued

SUMMARY OF EN INHIBITOR $IC_{50}$, $K_D$, AND RETROTRANSPOSITION VALUES.

| Inhibitor ID | $IC_{50}$ (µM) | $K_d$ (µM) | Inhibitor ID |
|---|---|---|---|
| AD34 | 13.6 ± 4.4 | 1.8 ± 0.4 | 25 µM: 104.3 ± 7.8 |
| AD36 | 928.3 ± 436.7 | 228.0 ± 18.5 | 25 µM: 42.9 ± 22.2 |
| AD41 | 458.8 ± 224.3 | N.D. | 25 µM: 129.9 ± 12.0 |
| AD43 | 703.9 ± 176.7 | 516.3 ± 69.0 | 50 µM: 57.3 ± 9.0 |
| AD50 | 291.6 ± 18.4 | 207.0 ± 43.3 | 25 µM: 100.5 ± 15.0 |

In Table 5, $IC_{50}$ values were calculated from 3 independent experiments of the fluorescent oligonucleotide nicking assay with 3 replicates each and are mean±s.d. Kd values were calculated from at least 3 independent spectral shift experiments with 3 replicate measurements each and are mean±s.d. N.D., binding not detected. Retrotransposition efficiencies (RetroT efficiency) relative to no inhibitor control were calculated from at least 3 independent experiments with 4 replicates each and are mean±s.d.

L1-Induced DNA Damage is Mitigated by EN Inhibitors

We next aimed to test the effects of EN inhibitors on DNA damage associated with L1 expression. Inactivation of EN by active site point mutation has been previously shown to significantly reduce DNA damage when L1 is overexpressed. We thus transfected doxycycline-inducible plasmid constructs expressing WT or mutant full-length L1 (FL, containing ORF1 and ORF2) or the EN domain into HeLa Tet208 On cells. With these cultures we measured the impacts of EN inhibitors on L1-induced DNA damage with two assays: γ-H2AX immunofluorescence staining and neutral comet assay. After induction of expression with doxycycline and addition of inhibitors, DNA damage was detected using immunofluorescence for γ-H2AX, a marker of double-stranded DNA breaks. This staining was then quantified using a pipeline from CellProfiler that we adapted to measure the average γ-H2AX signal for each nucleus with DNA damage. Point mutations in both domains either prevented or significantly reduced DNA damage, consistent with previously published results. Our results show that the EN inhibitors reduce γ-H2AX signal both when FL L1 is expressed, as well as when the EN domain is expressed alone (FIG. 9A, FIG. 9B). We also used the neutral comet assay, which detects overall DNA fragmentation by exposing cells to electrophoresis and measuring the amount of damaged DNA that migrates out of the disrupted nucleus. We showed DNA damage in response to EN WT induction that was mitigated by EN point mutation and lack of doxycycline. We included treatment with hydrogen peroxide as a control for DNA damage. We then quantified these images using OpenComet to identify nuclei and measure comet parameters, including tail length and tail moment (FIG. 9C, FIG. 9D). While tail length measures the distance the fragmented DNA travels from the nucleus, the tail moment also accounts for the percent of total DNA located in the tail relative to the nucleus. In both assays, we observed decreases in DNA damage in response to treatment with several inhibitors, with the amount of reduction falling between the uninduced and WT samples. Together, these assays demonstrate that small molecule EN inhibitors can reduce DNA damage caused by the expression of L1.

EN Inhibitors Impact Senescence-Associated Inflammatory Markers in Cell Culture

The final cellular impact of L1 we investigated was upregulation of inflammatory markers in senescent cells. To accomplish this, we generated replicative senescent cells in culture. Human diploid fibroblasts (LF1) were passaged until they no longer were dividing, then maintained in culture for 3 to 5 months without passaging before inhibitor treatment and sample harvesting (FIG. 10A). These durations were based on previous evidence from our laboratory demonstrating significant expression of L1 at later stages of senescence beginning around 3 months. We also performed a variety of assays to confirm senescence as previously described, including tracking growth rate, monitoring cellular morphology, completing the senescence-associated β-galactosidase assay, measuring expression of inflammatory factors, and visualizing senescence markers by immunofluorescence. We then used these cultures to test the effects of EN inhibitors on the expression of inflammatory markers in senescent cells (FIGS. 10B-10F). After treating cells with inhibitors for 1 month, we extracted the RNA and measured levels of components of the senescence-associated secretory phenotype (SASP) and type-I interferon (IFN) response by RT-qPCR. In all experiments we included 3TC as a control for RT inhibition. We found mostly similar effects for 3TC and EN inhibitors on the indicated markers across three independent cultures of senescent cells. In order to assay additional gene expression changes upon inhibitor treatment, we performed RNA-seq transcriptomic analysis. We found that 3TC and AD12 both resulted in decreased expression of our previously published IFN gene set and a set of genes associated with aging. These results demonstrate that pharmacological inhibition of both the RT and EN domains mitigates expression of inflammatory factors in senescent cells.

RNA-Seq Transcriptomic Analysis

RNA was extracted as described above and processed through Azenta Inc. using Illumina 2×150 bp paired-end sequencing. Reads were preprocessed with fastp, aligned to the GRCh38.p14 human genome assembly with STAR76, and assigned to genes using featureCounts. Counts were normalized and differential gene expression analysis was performed by DESeq. Gene Set Enrichment Analysis was performed for KEGG pathways, interferon response, and the aging gene set and the nominal p-values adjusted for false discovery rate by the Benjamini-Hochberg method. Heat maps were generated using Morpheus (from Broadinstitute.org).

We describe here a set of structurally diverse small molecule EN inhibitors. We have identified these inhibitors through various computational screening methods and quantified their respective efficacies with purified EN domain. Furthermore, we have demonstrated that these inhibitors also mitigate retrotransposition, L1-induced DNA damage, and inflammation in senescent cells, which are disease relevant impacts of L1 activity. These inhibitors could serve as key tools in better understanding L1 function from a basic science perspective and as initial candidates for the development of therapeutics for age associated diseases.

We found differential potency among the inhibitors when comparing results from the in vitro and downstream cellular assays. Several inhibitors showed clear activity in vitro but did not significantly impact retrotransposition in cells: AD2, AD5, AD17, AD18, AD34. This discrepancy could be due to several factors including low solubility, sequestration or degradation, or poor cell permeability. Among these inhibitors, AD18 could be a good starting point for further development of compounds with improved cellular properties, since it already has good in vitro potency and has unique functional groups relative to the other inhibitors. On the other hand, several inhibitors showed relatively low efficacy in vitro but high activity in the retrotransposition assay: AD7, AD9, AD12, AD32, AD36, and AD43. One possibility is that these compounds have higher cell permeability, allowing them to achieve higher intracellular concentrations. This is supported by the fact that AD12 is a therapeutic for diabetes mellitus type 2 (Gliquidone) and therefore has been optimized for bioavailability. In a biological context, even weak EN inhibition might significantly impact retrotransposition. First, TPRT only requires one or two nicks by the EN for productive insertion, a situation different from the multi-turnover kinetics we measured in vitro. Second, the EN is a relatively slow enzyme, similar to retroviral integrases that also only need to accomplish a few catalytic cycles for propagation. This might be an evolutionary advantage that allows for a balance between L1 integration and EN-dependent DNA damage that could harm the host. Therefore, even weak EN inhibitors are good candidates for cellular testing and future development.

The inhibitors also impacted L1 activity differently in the various cell-based assays used here. While the retrotransposition assay requires full length L1, the DNA damage assays were performed using both full length L1 and EN domain-only constructs. This allows for evaluation of DNA damage inhibition in the context of L1 retrotransposition-competent full-length sequences in comparison to the EN domain alone. L1 elements that are incapable of retrotransposition but retain potentially active EN coding sequences are abundant in the human genome and thus have the potential to create DNA damage if expressed. It is interesting to note that inhibitors with the best inhibition in the full length L1 DNA damage experiments were generally the ones with the best inhibition in the retrotransposition assay, for example AD3 and AD12. In a similar way, inhibitors with better efficacy in the EN domain-only DNA damage experiments were more likely to have lower in vitro IC50 and $K_d$ values, such as AD11, AD14, and AD16. In addition, the results in senescent cells show efficacy from inhibitors in both these groups: AD3, AD12, and AD14. Together, these results suggest that various inhibitors may interact differently with the EN in the context of the full-length ORF2 versus the isolated domain and result in different modulations of the downstream consequences of L1 activity. Some evidence suggests that EN activity is reduced in full length ORF255, potentially resulting in partial occlusion of the active site and therefore inhibitor binding surface. Conversely, the full length ORF2 could provide additional binding surfaces for inhibitor interactions that could reduce retrotransposition by impairing ORF2 function overall, including the RT domain directly or the coordination between the domains during TPRT. Finally, it has to be considered that cellular EN activity occurs within a complex L1 RNP that interacts with multiple host proteins. These interacting proteins vary depending on the localization of the RNP in the nucleus or cytoplasm, and so could have different impacts on the ability of the EN to bind to inhibitors. As a result, interactions between the EN and inhibitors may also be influenced by the step in the L1 life cycle.

Our results regarding the role of the EN in retrotransposition and DNA damage agree with previous research demonstrating that when overexpressing L1, EN active site mutations prevent retrotransposition and DNA damage. However, analogous experiments have not been performed to investigate the role of the EN in the production of inflammatory L1 cDNA found in the cytoplasm of senescent cells. This is mostly because of technical challenges inherent in creating active site mutations in endogenous L1s being expressed from multiple loci in the genome. RT inhibitors like 3TC have helped answer these questions with regard to RT function, but the absence of EN inhibitors has prevented similar experiments to investigate the role of the EN. We report here early data on testing the role of EN in the pathways that generate these sequences and the subsequent inflammatory signals. Our results suggest that the EN is at least partially involved in this process, as EN and RT inhibition resulted in similar decreases in expression of some inflammatory markers. Since our current understanding of the EN's function in TPRT is limited to nicking of nuclear DNA, the potential involvement of the domain in initiating the production of L1 cDNA found in the cytoplasm is less well understood. One possibility is that nuclear envelope damage that has been widely documented in senescent cells allows for intermediates of retrotransposition primed in the nucleus by canonical TPRT to enter the cytoplasm and trigger the IFN-I response through the cGAS-STING pathway. Another possible explanation is that the EN can function in the cytoplasm to improve RT priming by nicking chromatin fragments prevalent in senescent cells or other sequences such as mitochondrial DNA, with preference for AT-rich sequences that promote RT priming. Some evidence suggests that many of these extranuclear sequences are double-stranded and would therefore require nicking. Yet another indirect possibility is that nuclear EN activity promotes DNA fragmentation and creation of these chromatin fragments as part of the persistent DNA damage present in senescent cells. In other cellular models with decreased cytoplasmic DNase activity, a hallmark of senescence progression, accumulation of cytoplasmic DNA has been observed in response to pharmacological DNA damage induction63. Ultimately, L1 cDNA may be produced using some or none of these pathways in addition to EN-independent RT priming by ssDNA fragments in the cytoplasm.

In characterizing these EN inhibitors in multiple cellular assays, we have completed initial testing of the effects of pharmacological EN inhibition in cells. We believe the most promising current EN inhibitors for further exploration in cells to be AD3, AD9, AD12, AD14, AD16, and AD43. We have chosen these inhibitors due to their relative efficacies across assays, demonstration of direct binding by spectral shift, and variety of sizes and structures. This diversity of EN inhibitors described here, in combination with the relatively large DNA-binding surface of the EN, suggests that more classes of EN inhibitors are theoretically possible. This could mitigate concerns regarding cross-reactivity with other cellular enzymes and provide better management of any off-target effects. Broadly speaking, these inhibitors and future, higher affinity inhibitors could be used to study EN function in a wider range of cellular contexts than currently possible, much like our senescence experiments. As previously noted, most of what we know about L1 has been garnered using overexpression models. While useful, including for experiments in this study, this approach should be complemented with more biologically relevant ones that rely on endogenous L1 expression. These inhibitors could therefore be used to determine the effects of EN inhibition across cell lines, animal models, and diseases, such as in cancer and neurodegeneration where retrotransposition, DNA damage, and inflammation resulting in part from L1 activity may play roles in disease progression. Indeed, RT inhibitors have been used to test the contribution of RT activity to various L1-associated phenotypes present in disease. However, RT inhibitors, while available and numerous, mostly rely on the same chain-terminating chemistry and therefore have similar off-target effects. EN inhibitors specifically provide an orthogonal pharmacological approach to L1 inhibition to support that any positive impacts are in fact from L1 inhibition, and not off-target effects. Finally, EN inhibitors could be advantageous for reducing DNA damage specifically, as this domain is directly responsible for DNA damage by nicking DNA.

In summary, we have characterized the first small molecule inhibitors of the LINE-1 retrotransposon endonuclease domain. In the short term, these inhibitors can serve as tools to improve our understanding of L1 biology in a similar way to how compounds repurposed for RT inhibition have been used. Ultimately, these inhibitors represent a starting point for future development of potential therapeutics for diseases associated with L1 expression, many of which are age-associated diseases.

All patents, patent application, and publications cited herein are fully incorporated by reference herein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

REFERENCES

[i] Engel, P. (2014). These Staggering Maps Show How Much The World's Population Is Aging. Business Insider, May 16, 2014.

[ii] Chung H Y, et al., (2009). Molecular inflammation: underpinnings of aging and age-related diseases. Ageing Res. Rev. 8(1): 18-30

[iii] Pawelec G, et al., (2014). Inflammation, ageing and chronic disease. Current Opinion in Immunology. 29: 23-28.

[iv] Jurk, D. et al., (2014). Chronic inflammation induces telomere dysfunction and accelerates ageing in mice. Nature Communications, Vol 5, Article: 4172.

[v] Singh, T. & Newman, A. B. (2011). Inflammatory markers in population studies of aging. Ageing Res Rev. 10(3): 319-329.

[vi] Diagnostic and Statistical Manual of Mental Disorders, Fifth Edition, pp. 602-614, American Psychiatric Association Publishing, Washington, DC (2013).

[vii] Feng. Q., et al. (1996). Human L1 retrotransposon encodes a conserved endonuclease required for retrotransposition. Cell, 87(5), 905-916.

[viii] Weichenrieder, O., et al. (2004). Crystal structure of the targeting endonuclease of the human LINE-1 retrotransposon. Structure, 12(6), 975-986.

[ix] Srinivasan, A., et al. (2012). Identification and characterization of human apurinic/apyrimidinic endonuclease-1 inhibitors. Biochemistry 51(31): 6246-6259.

[x] See, e.g., Isselbacher et al. (1996) Harrison's Principles of Internal Medicine 13 ed., 1814-1882.

[xi] López-Otín, C., et al. (2013). The hallmarks of aging. Cell, 153(6), 1194-217.

[xii] De Cecco, M., et al. (2013) Genomes of replicatively senescent cells undergo global epigenetic changes leading to gene silencing and activation of transposable elements. Aging Cell, 12(2), 247-256.

[xiii] De Cecco, M., et al. (2013). Transposable elements become active and mobile in the genomes of aging mammalian somatic tissues. Aging, 5(12), 867-883.

[xiv] Ostertag, E. M., and Kazazian Jr, H. H. (2001). Biology of mammalian L1 retrotransposons. Annual Review of Genetics, 35(1), 501-538.

[xv] De Cecco, M. et al. (2019). L1 drives IFN in senescent cells and promotes age-associated inflammation. Nature, 566(7742), 73-78.

[xvi] Sedivy, J. M. and De Cecco, M., et al. (2020). International Application WO/2020/154656 entitled: Compositions and Methods for Treating, Preventing or Reversing Age-Associated Inflammation and Disorders.

[xvii] Franceschi, C. & Campisi, J. (2014). Chronic inflammation (inflammaging) and its potential contribution to age-associated diseases. J. Gerontol. A Biol. Sci. Med. Sci. 69 Suppl. 1, S4-9.

[xviii] Lopez-Otin, C. et al. (2013). The hallmarks of aging. Cell 153, 1194-217.

[xix] Lopez-Otin, C., et al. (2013). The hallmarks of aging. Cell 153, 1194-1217.

[xx] Bussian, T. J., et al. (2018). Clearance of senescent glial cells prevents tau-dependent pathology and cognitive decline. Nature 562, 578-582.

[xxi] Childs, B. G., et al. (2016). Senescent intimal foam cells are deleterious at all stages of atherosclerosis. Science 354, 472-477.

[xxii] Baker, D. J., et al. (2016). Naturally occurring p16 (Ink4a)-positive cells shorten healthy lifespan. Nature 530, 184-189.

[xxiii] Demaria, M., et al. (2017). Cellular Senescence Promotes Adverse Effects of Chemotherapy and Cancer Relapse. Cancer Discov 7, 165-176.

[xxiv] Chang, J., et al. (2016). Clearance of senescent cells by ABT263 rejuvenates aged hematopoietic stem cells in mice. Nat Med 22, 78-83.

[xxv] Schafer, M. J., et al. (2017). Cellular senescence mediates fibrotic pulmonary disease. Nat Commun 8, 14532.

[xxvi] Farr, J. N., et al. (2017). Targeting cellular senescence prevents age-related bone loss in mice. Nat Med 23, 1072-1079.

[xxvii] Chinta, S. J., et al. (2018). Cellular Senescence Is Induced by the Environmental Neurotoxin Paraquat and Contributes to Neuropathology Linked to Parkinson's Disease. Cell Rep 22, 930940.

[xxviii] Xu, M., et al. (2018). Senolytics improve physical function and increase lifespan in old age. Nat Med 24, 1246-1256.

[xxix] Schafer, M. J., et al. (2017). Cellular senescence mediates fibrotic pulmonary disease. Nat Commun 8, 14532.

[xxx] Demaria, M., et al. (2014). An essential role for senescent cells in optimal wound healing through secretion of PDGF-AA. Dev Cell 31, 722-733.

[xxxi] See, U.S. Published Patent Application 2018/0050000.
[xxxii] See, U.S. Published Patent Application 2018/0050000.
[xxxiii] Caira M., et al. (2004). Preparation and crystal characterization of a polymorph, a monohydrate, and an ethyl acetate solvate of the antifungal fluconazole. J. Pharmaceut. Sci., 93(3):601-611.
[xxxiv] Van Tonder E. C., et al. (2004). Preparation and Physicochemical Characterization of 5 Niclosamide Solvates and 1 Hemisolvate. AAPS Pharm. Sci. Tech., 5(1): Article 12.
[xxxv] Bingham A. L., et al. (2001). Over one hundred solvates of sulfathiazole: solvates and adducts of sulfathiazole. Chem. Commun. 7: 603-604.
[xxxvi] Remington's Pharmaceutical Sciences, Mack Publishing Co., Easton, PA, 19th ed. 1995.
[xxxvii] Feng, Q., et al. (1996). Human L1 retrotransposon encodes a conserved endonuclease required for retrotransposition. Cell 87, 905-916.
[xxxviii] Repanas, K. et al. (2007). Determinants for DNA target structure selectivity of the human LINE-1 retrotransposon endonuclease. Nucleic Acids Res. 35, 4914-4926.
[xxxix] Weichenrieder, O., et al. (2004). Crystal structure of the targeting endonuclease of the human LINE-1 retrotransposon. Structure 12, 975-986.
[xl] Mita P., et al. (2020). BRCA1 and S phase DNA repair pathways restrict LINE-1 retrotransposition in human cells. Nat. Struct. Mol. Biol. 27, 179-191.

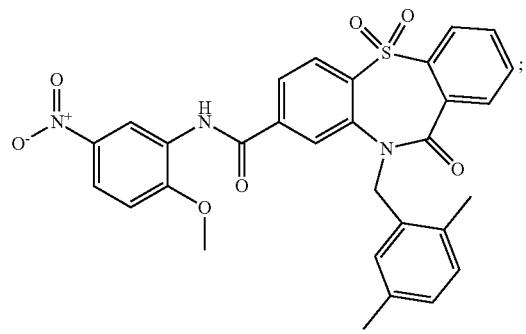

(AD34)

and wherein the age-associated inflammation is in a patient having Alzheimer's disease.

2. The method of claim 1, wherein the patient experiences a decrease in one or more symptoms of the Alzheimer's disease after the administration of the AD34 to the patient; and wherein the decrease in the one or more symptoms is evaluated according to the Diagnostic and Statistical Manual of Mental Disorders, 5th Edition (DSM-5).

What is claimed is:

1. A method for treating an age-associated inflammation in a patient in need thereof, the method comprising administering a therapeutically effective amount of a long interspersed nuclear element-1 (L1) endonuclease (EN) inhibitor to the patient; wherein the L1 EN inhibitor is AD34 of the chemical structure shown below:

3. The method of claim 1, wherein the patient experiences a decrease in one or more symptoms of the Alzheimer's disease after the administration of the AD34 to the patient; and wherein the decrease of one or more symptoms is determined using the cognitive subscale of the Alzheimer's Disease Assessment Scale (ADAS-cog), the Clinician's Interview-Based Impression of Change (CIBIC-plus), or the Activities of Daily Living Scale (ADL).

4. The method of claim 1, further comprising an administering of at least one second therapeutic agent to the patient.

\* \* \* \* \*